United States Patent
Jung et al.

(10) Patent No.: US 12,096,686 B2
(45) Date of Patent: Sep. 17, 2024

(54) COMPOUND AND ORGANIC LIGHT EMITTING DEVICE COMPRISING THE SAME

(71) Applicant: LG CHEM, LTD., Seoul (KR)

(72) Inventors: Min Woo Jung, Daejeon (KR); Dong Hoon Lee, Daejeon (KR); Boon Jae Jang, Daejeon (KR); Jungha Lee, Daejeon (KR); Su Jin Han, Daejeon (KR); Seulchan Park, Daejeon (KR); Sunghyun Hwang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 983 days.

(21) Appl. No.: 17/054,069

(22) PCT Filed: Aug. 22, 2019

(86) PCT No.: PCT/KR2019/010709
§ 371 (c)(1),
(2) Date: Nov. 9, 2020

(87) PCT Pub. No.: WO2020/040571
PCT Pub. Date: Feb. 27, 2020

(65) Prior Publication Data
US 2021/0280800 A1  Sep. 9, 2021

(30) Foreign Application Priority Data

Aug. 22, 2018 (KR) .......... 10-2018-0098141
Aug. 21, 2019 (KR) .......... 10-2019-0102578

(51) Int. Cl.
| H01L 51/54 | (2006.01) |
| C07D 405/04 | (2006.01) |
| C07D 405/10 | (2006.01) |
| C07D 405/14 | (2006.01) |
| C07D 409/14 | (2006.01) |
| C09K 11/06 | (2006.01) |
| H10K 85/60 | (2023.01) |
| H10K 50/11 | (2023.01) |
| H10K 101/00 | (2023.01) |
| H10K 101/10 | (2023.01) |

(52) U.S. Cl.
CPC ....... *H10K 85/6574* (2023.02); *C07D 405/04* (2013.01); *C07D 405/10* (2013.01); *C07D 405/14* (2013.01); *C07D 409/14* (2013.01); *C09K 11/06* (2013.01); *H10K 85/622* (2023.02); *H10K 85/654* (2023.02); *H10K 85/6576* (2023.02); *C09K 2211/1018* (2013.01); *H10K 50/11* (2023.02); *H10K 2101/10* (2023.02); *H10K 2101/90* (2023.02)

(58) Field of Classification Search
None
See application file for complete search history.

(56) References Cited

U.S. PATENT DOCUMENTS

| 2004/0251816 A1 | 12/2004 | Leo et al. |
| 2016/0141519 A1 | 5/2016 | Seo et al. |
| 2018/0337348 A1 | 11/2018 | Jung et al. |
| 2019/0047991 A1 | 2/2019 | Jung et al. |

FOREIGN PATENT DOCUMENTS

| JP | 2017-107992 A | 6/2017 |
| KR | 10-2000-0051826 A | 8/2000 |
| KR | 10-2015-0031396 A | 3/2015 |
| KR | 10-2017-0058579 A | 5/2017 |
| KR | 10-2018-0010165 A | 1/2018 |
| KR | 10-2018-0061074 A | 6/2018 |
| KR | 10-2018-0068869 A | 6/2018 |
| KR | 10-1885899 B1 | 8/2018 |
| TW | 2013-48202 A | 12/2013 |
| TW | 2018-11773 A | 4/2018 |
| WO | 2003-012890 A2 | 2/2003 |
| WO | 2013-146942 A1 | 10/2013 |
| WO | 2016-108596 A2 | 7/2016 |
| WO | 2018-016742 A1 | 1/2018 |
| WO | 2018-093015 A1 | 5/2018 |
| WO | 2019-017731 A1 | 1/2019 |
| WO | 2019-054833 A1 | 3/2019 |
| WO | 2019-164218 A1 | 8/2019 |

OTHER PUBLICATIONS

Machine translation of JP2017107992. (Year: 2017).*
Machine translation of WO2016108596. (Year: 2016).*

* cited by examiner

*Primary Examiner* — Andrew K Bohaty
(74) *Attorney, Agent, or Firm* — Bryan Cave Leighton Paisner LLP

(57) ABSTRACT

The present disclosure provides a novel compound represented by the following Chemical Formula 1, and an organic light emitting device including the same. The compound is used as a material of an organic material layer of the organic light emitting device.

[Chemical Formula 1]

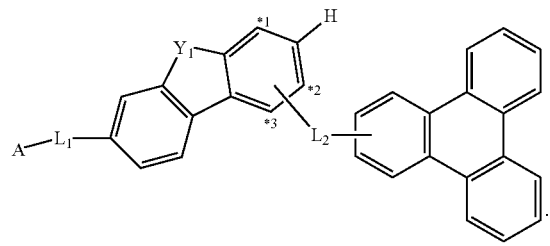

11 Claims, 1 Drawing Sheet

[FIG. 1]
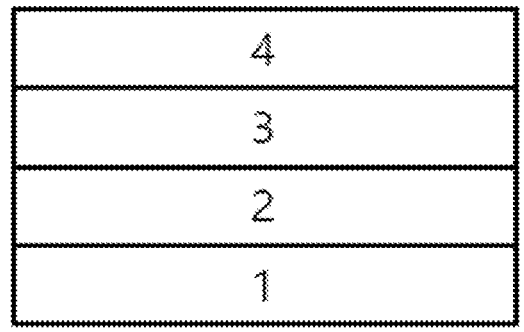
[FIG. 2]
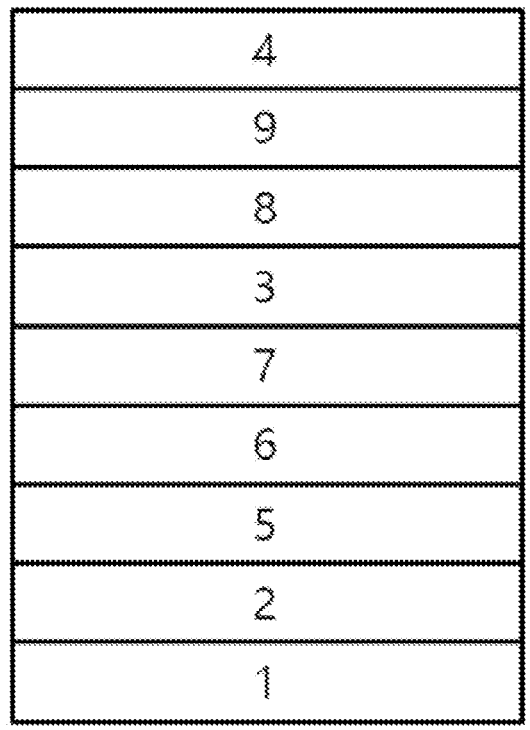

COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2019/010709 filed on Aug. 22, 2019, which claims the benefit of the filing dates of Korean Patent Application No. 10-2018-0098141 filed with the Korean Intellectual Property Office on Aug. 22, 2018, and Korean Patent Application No. 10-2019-0102578 filed with the Korean Intellectual Property Office on Aug. 21, 2019, the entire contents of which are incorporated herein by reference.

BACKGROUND OF THE INVENTION

(a) Field of the Invention

The present invention relates to a novel compound and to an organic light emitting device including the same.

(b) Description of the Related Art

In general, an organic light emitting phenomenon refers to a phenomenon where electrical energy is converted into light energy by using an organic material. The organic light emitting device using the organic light emitting phenomenon has characteristics such as a wide viewing angle, excellent contrast, a fast response time, and excellent luminance, driving voltage, and response speed, and thus many studies have proceeded thereon.

The organic light emitting device generally has a structure which includes an anode, a cathode, and an organic material layer interposed between the anode and the cathode. The organic material layer frequently has a multilayered structure that includes different materials in order to enhance efficiency and stability of the organic light emitting device, and for example, the organic material layer may be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

PRIOR ART LITERATURE

Patent Literature (Patent Literature 0001) Korean Patent Laid-open Publication No. 10-2000-0051826

SUMMARY OF THE INVENTION

Technical Problem

It is an object of the present invention to provide a novel compound and an organic light emitting device including the same.

Technical Solution

In one aspect of the invention, there is provided a compound represented by the following Chemical Formula 1:

[Chemical Formula 1]

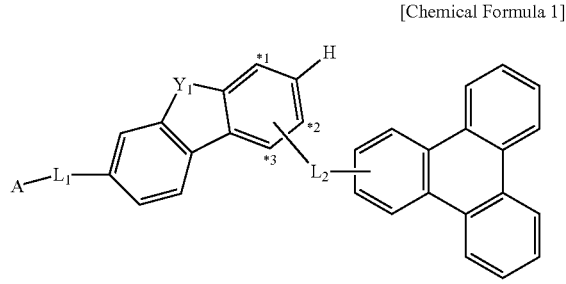

wherein in Chemical Formula 1,
$Y_1$ is O or S,
$L_1$ and $L_2$ are each independently a single bond, a substituted or unsubstituted $C_{6-60}$ arylene, or a substituted or unsubstituted $C_{2-60}$ heteroarylene containing one or more heteroatoms selected from the group consisting of O, N, and S,
with the proviso that $L_2$ is bonded to any one of positions *1, *2, and *3,
A is represented by any one of Chemical Formulas 2 to 4,

[Chemical Formula 2]

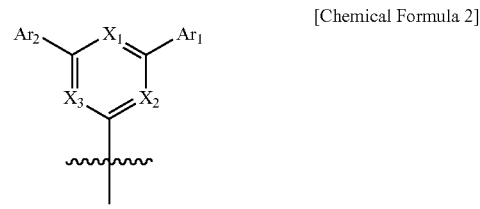

[Chemical Formula 3]

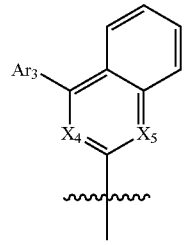

[Chemical Formula 4]

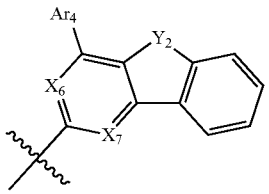

wherein in Chemical Formulas 2 to 4,
$X_1$ to $X_3$ are each independently N or CH, with the proviso that at least two of $X_1$ to $X_3$ are N,
$X_4$ and $X_5$ are each independently N or CH, with the proviso that at least one of $X_4$ and $X_5$ is N,
$X_6$ and $X_7$ are each independently N or CH, with the proviso that at least one of $X_6$ and $X_7$ is N,
$Y_2$ is O or S, and
$Ar_1$ to $Ar_4$ are each independently a substituted or unsubstituted $C_{6-60}$ aryl, or a substituted or unsubstituted $C_{2-60}$ heteroaryl containing one or more heteroatoms selected from the group consisting of N, O, and S, with the proviso that when $L_2$ is bonded to position *3 and A is represented by Chemical Formula 2, $Ar_2$ is a substituted or unsubstituted $C_{10-60}$ aryl, or a substituted or unsubstituted $C_{2-60}$ heteroaryl containing one or more heteroatoms selected from the group consisting of N, O, and S.

In another aspect of the invention, there is provided an organic light emitting device including: a first electrode; a second electrode provided to face the first electrode; and one or more organic material layers provided between the first electrode and the second electrode, wherein one or more layers of the organic material layers include the compound represented by Chemical Formula 1.

Advantageous Effects

The compound represented by Chemical Formula 1 described above can be used as a material of an organic material layer of an organic light emitting device, and may improve efficiency, and achieve a low driving voltage and/or improve lifetime characteristics in the organic light emitting device.

BRIEF DESCRIPTION OF THE DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, an electron blocking layer 7, a light emitting layer 3, an electron transport layer 8, an electron injection layer 9 and a cathode 4.

DETAILED DESCRIPTION OF THE EMBODIMENTS

Hereinafter, embodiments of the present invention will be described in more detail to facilitate understanding of the present invention.

As used herein, the notation  means a bond linked to another substituent group, and the single bond means that there is no separate atom at a part represented as $L_1$ and $L_2$.

As used herein, the term "substituted or unsubstituted" means being unsubstituted or substituted with one or more substituents selected from the group consisting of: deuterium; a halogen group; a cyano group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heteroaryl containing at least one of N, O, and S atoms, or being unsubstituted or substituted with a substituent to which two or more substituents are linked among the substituents exemplified above. For example, "the substituent to which two or more substituents are linked" may be a biphenyl group. That is, the biphenyl group may also be an aryl group and may be interpreted as a substituent to which two phenyl groups are linked.

In the present specification, the number of carbon atoms of a carbonyl group is not particularly limited, but is preferably 1 to 40. Specifically, the carbonyl group may be a compound having the following structural formulas, but is not limited thereto.

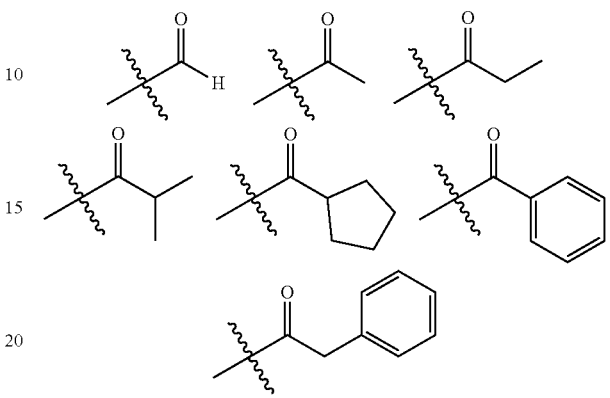

In the present specification, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a compound having the following structural formulas, but is not limited thereto.

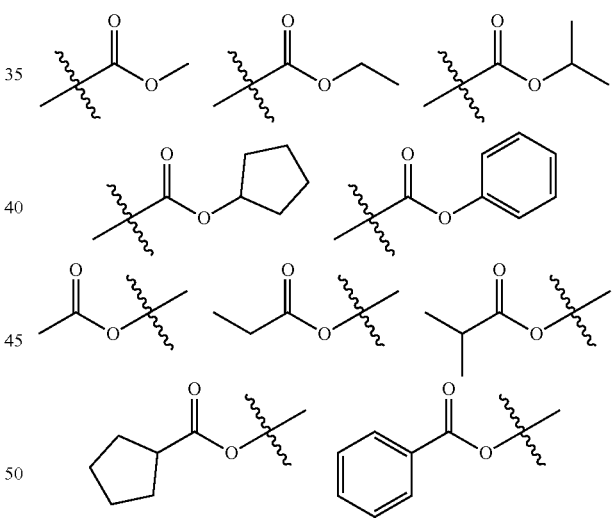

In the present specification, the number of carbon atoms of an imide group is not particularly limited, but is preferably 1 to 25. Specifically, the imide group may be a compound having the following structural formulas, but is not limited thereto.

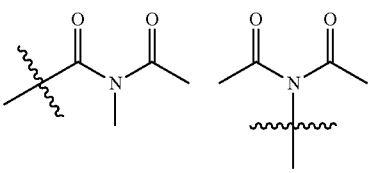

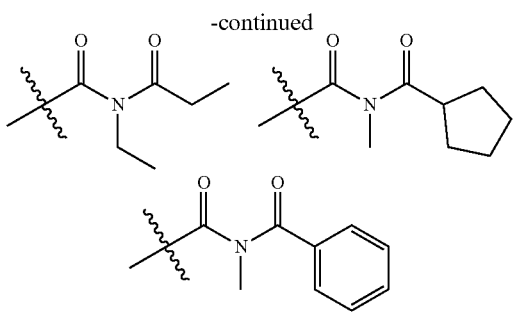

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, the alkyl group may be a straight-chain or branched-chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to a further embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group may be a straight-chain or branched-chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and it may be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group may be a phenyl group, a biphenyl group, a terphenyl group, or the like as the monocyclic aryl group, but is not limited thereto. The polycyclic aryl group includes a naphthyl group, an anthracenyl group, a phenanthryl group, a pyrenyl group, a perylenyl group, a chrysenyl group, a fluorenyl group, or the like, but is not limited thereto.

In the present specification, a fluorenyl group may be substituted, and two substituent groups may be bonded to each other to form a spiro structure. In the case where the fluorenyl group is substituted,

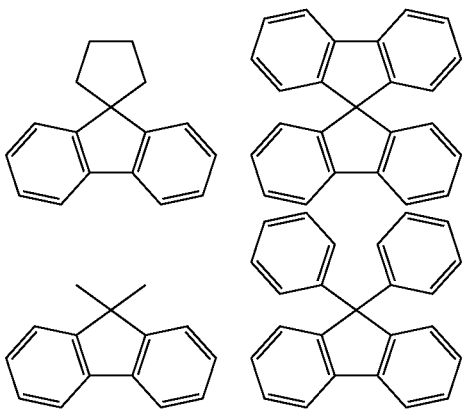

and the like can be formed. However, the structure is not limited thereto.

In the present specification, a heteroaryl is a heteroaryl including one or more of O, N, Si, and S as a heteroatom, and the number of carbon atoms thereof is not particularly limited, but is preferably 2 to 60. Examples of the heteroaryl include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present specification, the aryl group in the aralkyl group, the aralkenyl group, the alkylaryl group, and the arylamine group are the same as the aforementioned examples of the aryl group. In the present specification, the alkyl group in the aralkyl group, the alkylaryl group, and the alkylamine group is the same as the aforementioned examples of the alkyl group. In the present specification, the heteroaryl in the heteroarylamine can be applied to the aforementioned description of the heteroaryl group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heteroaryl can be applied except that the heteroarylene is a divalent group. In the present specification, the aforementioned description of the aryl group or cycloalkyl group can be applied except that the hydrocarbon ring is not a monovalent group but is formed by combining two substituent groups. In the present specification, the aforementioned description of the heteroaryl can be applied, except that the heterocyclic group is not a monovalent group but is formed by combining two substituent groups.

On the other hand, one embodiment of the present invention provides a compound represented by Chemical Formula 1. The compound represented by Chemical Formula 1 has a structure in which one side of the benzene ring of the dibenzofuran/dibenzothiophene core is substituted with a substituent A, and the other side of the benzene ring is substituted with a triphenylenyl group in the remaining part excluding a position symmetrical with respect to the position substituted with the substituent A.

In addition, in Chemical Formula 1, when $L_2$ is bonded to position *3 and A is represented by Chemical Formula 2, $Ar_2$ is a substituted or unsubstituted $C_{10-60}$ aryl; or a substituted or unsubstituted $C_{2-60}$ heteroaryl containing one or more heteroatoms selected from the group consisting of N, O, and S.

The compound represented by Chemical Formula 1 may be preferably used as a host of the light emitting layer of the organic light emitting device, for example, as an n-type host used with a p-type host material. When the compound represented by Chemical Formula 1 is used as an n-type host, it has an excellent capability of stabilizing electrons and thus can maintain the balance of holes and electrons in the light emitting layer, as compared with a compound substituted with a triphenylenyl group at a position symmetrical with respect to a position substituted with a substituent A, and a compound in which $L_2$ is bonded to position *3, A is represented by Chemical Formula 2, and both $Ar_1$ and $Ar_2$ are phenyl. Thus, the organic light emitting device employing the compound of the present invention can improve efficiency and lifetime characteristics at the same time.

In addition, $L_1$ and $L_2$ may each independently be a single bond or a $C_{6-20}$ arylene.

For example, $L_1$ and $L_2$ may be each independently a single bond, phenylene, or biphenylylene.

In this case, at least one of $L_1$ and $L_2$ may be a single bond.

Moreover, when A is represented by Chemical Formula 2, $L_2$ may be bonded to position *1 or *2.

Alternatively, $L_2$ may be bonded to position *1 or *2.

Further, in Chemical Formula 2, $X_1$ to $X_3$ are N; $X_1$ and $X_2$ are N and $X_3$ is CH; or $X_2$ and $X_3$ are N and $X_1$ is CH, in Chemical Formula 3, $X_4$ and $X_5$ are N, and in Chemical Formula 4, $X_6$ and $X_7$ may be N.

The compound represented by Chemical Formula 1 may be represented as follows according to the bonding position of $L_2$. Specifically, when $L_2$ is bonded to position *1, the Chemical Formula 1 is represented by the following Chemical Formula 1A, when $L_2$ is bonded to position *2, Chemical Formula 1 is represented by the following Chemical Formula 1B, and when $L_2$ is bonded to position *3, Chemical Formula 1 is represented by the following Chemical Formula 1C:

[Chemical Formula 1A]

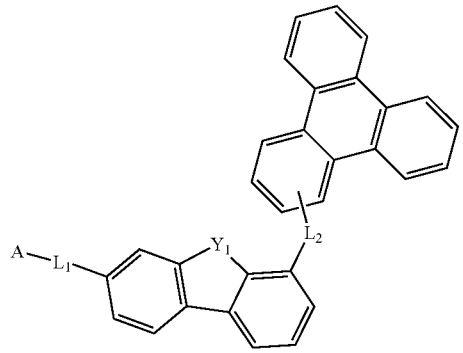

[Chemical Formula 1B]

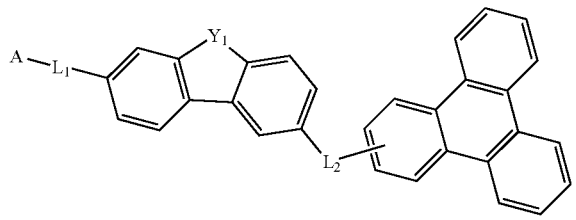

[Chemical Formula 1C]

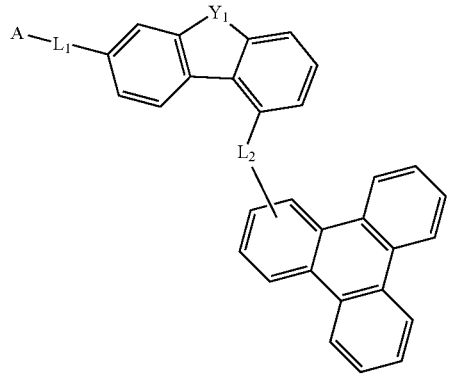

wherein in Chemical Formulas 1A to 1C,
the definitions of A, $Y_1$, $L_1$, and $L_2$ are the same as those defined in Chemical Formula 1.

In addition, in Chemical Formula 1A, A may be represented by any one of Chemical Formulas 2 to 4, in Chemical Formula 1B, A may be represented by any one of Chemical Formulas 2 to 4, and in Chemical Formula 1C, A may be represented by Chemical Formula 2 or 3.

In Chemical Formula 1A,
$Y_1$ is O or S,
$L_1$ and $L_2$ are each independently a single bond or a $C_{6-20}$ arylene, and
A is represented by any one of Chemical Formulas 2 to 4, in Chemical Formula 1B,
$Y_1$ is O or S,
$L_1$ and $L_2$ are each independently a single bond or a $C_{6-20}$ arylene, and A is represented by any one of Chemical Formulas 2 to 4, in Chemical Formula 1C, $Y_1$ is O or S, $L_1$ and $L_2$ are each independently a single bond or a $C_{6-20}$ arylene, and A is represented by any one of Chemical Formulas 2 to 4, and in Chemical Formula 2, $Ar_1$ may be a $C_{6-20}$ aryl; or a $C_{2-20}$ heteroaryl containing one atom of O or S, and $Ar_2$ may be a $C_{10-20}$ aryl; or a $C_{2-20}$ heteroaryl containing one atom of O or S.

In addition, $Ar_1$ to $Ar_4$ may each independently be a $C_{6-20}$ aryl; or a $C_{2-20}$ heteroaryl containing one atom of O or S. However, when $L_2$ is bonded to position *3 and A is represented by Chemical Formula 2, $Ar_1$, $Ar_3$, and $Ar_4$ are each independently a $C_{6-20}$ aryl; or a $C_{2-20}$ heteroaryl containing one atom of O or S, and $Ar_2$ may be a $C_{10-20}$ aryl; or a $C_{2-20}$ heteroaryl containing one atom of O or S.

For example, $Ar_1$ to $Ar_4$ may each independently be phenyl, biphenylyl, dibenzofuranyl, or dibenzothiophenyl. However, when $L_2$ is bonded to position *3 and A is represented by Chemical Formula 2, $Ar_1$, $Ar_3$, and $Ar_4$ may each independently be phenyl, biphenylyl, dibenzofuranyl, or dibenzothiophenyl, and $Ar_2$ may be biphenylyl, dibenzofuranyl, or dibenzothiophenyl.

Specifically, for example, in Chemical Formula 1A, $Ar_1$ to $Ar_4$ are each independently phenyl, biphenylyl, dibenzofuranyl, or dibenzothiophenyl, in Chemical Formula 1B, $Ar_1$ to $Ar_4$ are each independently phenyl, biphenylyl, dibenzofuranyl, or dibenzothiophenyl, and in Chemical Formula 1C, $Ar_1$, $Ar_3$, and Ara are each independently phenyl, biphenylyl, dibenzofuranyl, or dibenzothiophenyl, and $Ar_2$ is biphenylyl, dibenzofuranyl, or dibenzothiophenyl.

Further, the compound represented by Chemical Formula 1 may be represented as follows according to the structure of A. Specifically, when A is Chemical Formula 2, Chemical Formula 1 is represented by the following Chemical Formula 1D, when A is Chemical Formula 3, Chemical Formula 1 is represented by the following Chemical Formula 1E, and when A is Chemical Formula 4, Chemical Formula 1 is represented by the following Chemical Formula 1F:

[Chemical Formula 1D]

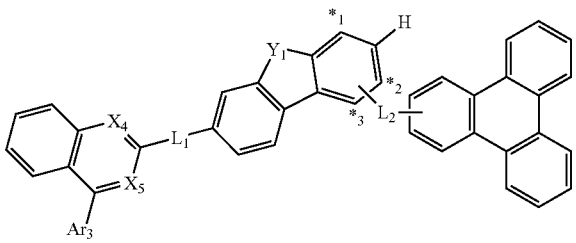

[Chemical Formula 1E]

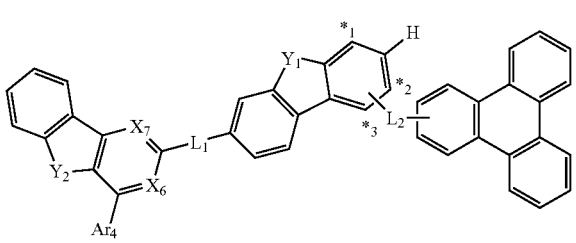

[Chemical Formula 1F]

wherein in Chemical Formulas 1D to 1F, the definitions of $Y_1$, $Y_2$, $L_1$, $L_2$, $X_1$ to $X_7$, and $Ar_1$ to $Ar_4$ are the same as those defined in Chemical Formula 1.

According to one embodiment, in Chemical Formula 1D, $L_2$ is bonded to position *1 or *2, and in Chemical Formula 1E, $L_2$ is bonded to position *1, *2, or *3, in Chemical Formula 1F, $L_2$ may be bonded to position *1, *2, or *3.

According to one embodiment, $Ar_1$, $Ar_3$, and $Ar_4$ are each independently a $C_{6-20}$ aryl; or a $C_{2-20}$ heteroaryl containing one atom of O or S, and $Ar_2$ may be a $C_{10-20}$ aryl; or a $C_{2-20}$ heteroaryl containing one atom of O or S.

For example, in Chemical Formulas 1D to 1F, $Ar_1$, $Ar_3$, and $Ar_4$ are each independently phenyl, biphenylyl, dibenzofuranyl, or dibenzothiophenyl, and $Ar_2$ may be biphenylyl, dibenzofuranyl, or dibenzothiophenyl, but are not limited thereto.

In addition, the aforementioned compound may be represented by any one of the following Chemical Formulas 1-1 to 1-6:

1-1

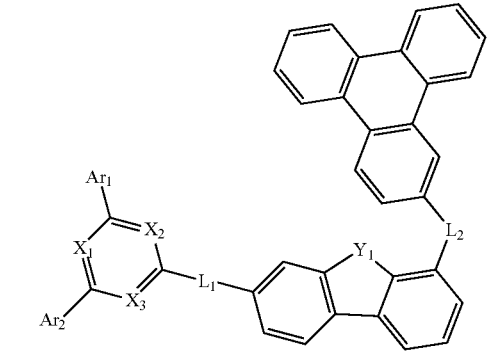

1-2

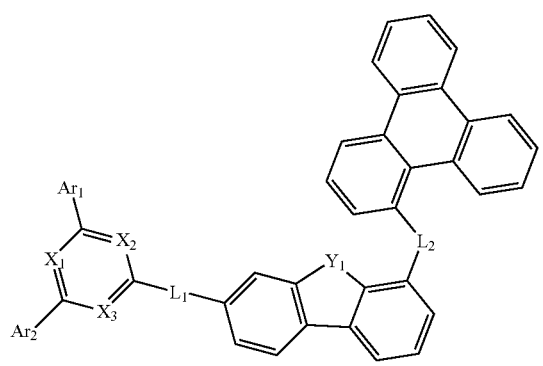

1-3

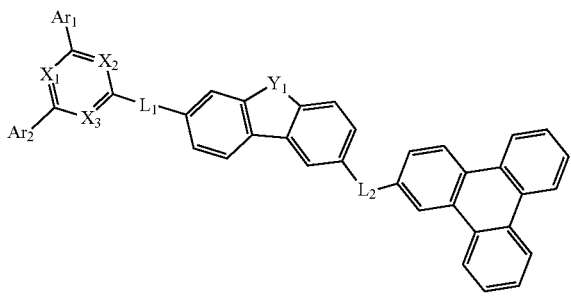

1-4

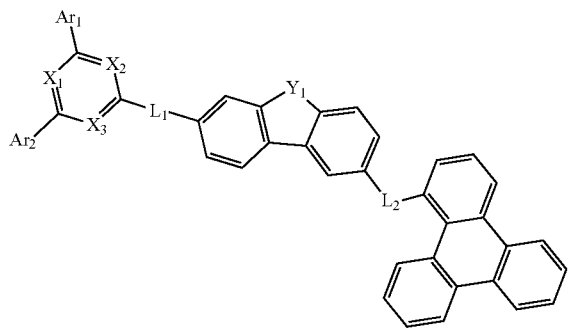

1-5

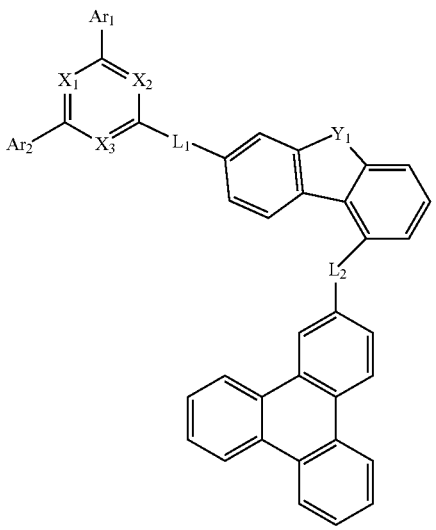

1-6

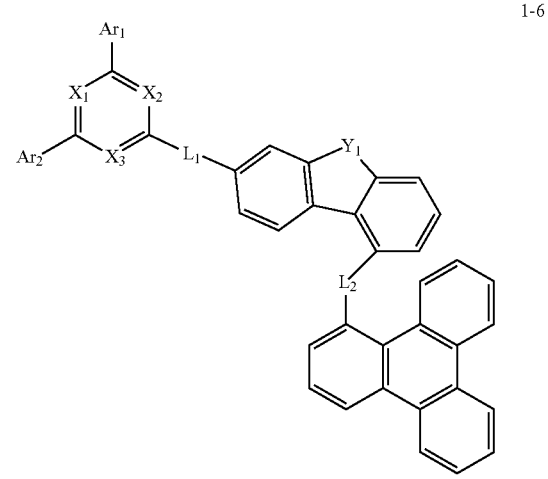

wherein in Chemical Formulas 1-1 to 1-6, $X_1$ to $X_3$ are N; or $X_1$ and $X_2$ are N, and $X_3$ is CH; or $X_2$ and $X_3$ are N, and $X_1$ is CH, the definitions of $Y_1$, $L_1$, $L_2$, $Ar_1$, and $Ar_2$ are the same as those defined in Chemical Formula 1.

Further, in Chemical Formulas 1-1 to 1-4, $Ar_1$ and $Ar_2$ are each independently phenyl, biphenylyl, dibenzofuranyl, or dibenzothiophenyl, in Chemical Formulas 1-5 and 1-6, $Ar_1$ is phenyl, biphenylyl, dibenzofuranyl, or dibenzothiophenyl, $Ar_2$ may be biphenylyl, dibenzofuranyl, or dibenzothiophenyl.

In addition, the aforementioned compound may be represented by any one of Chemical Formulas 1-1 to 1-4.

For example, the aforementioned compound may be any one selected from the group consisting of the following compounds:

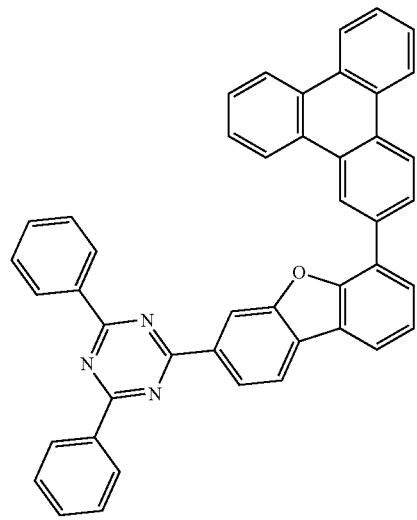
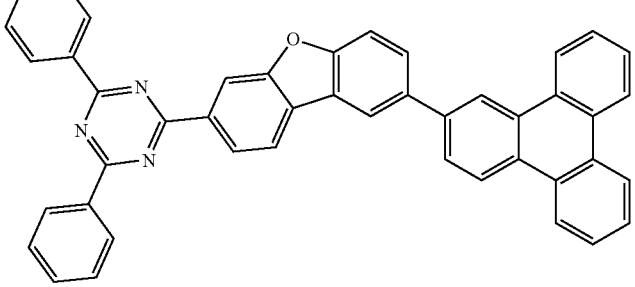
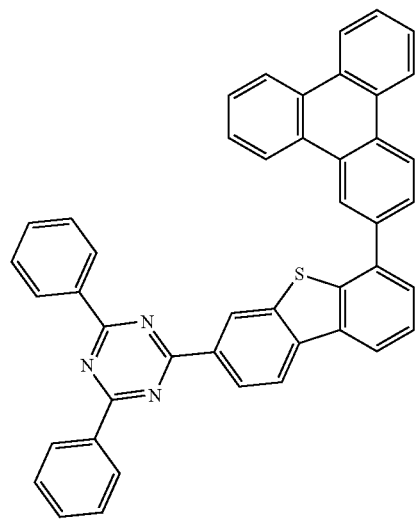
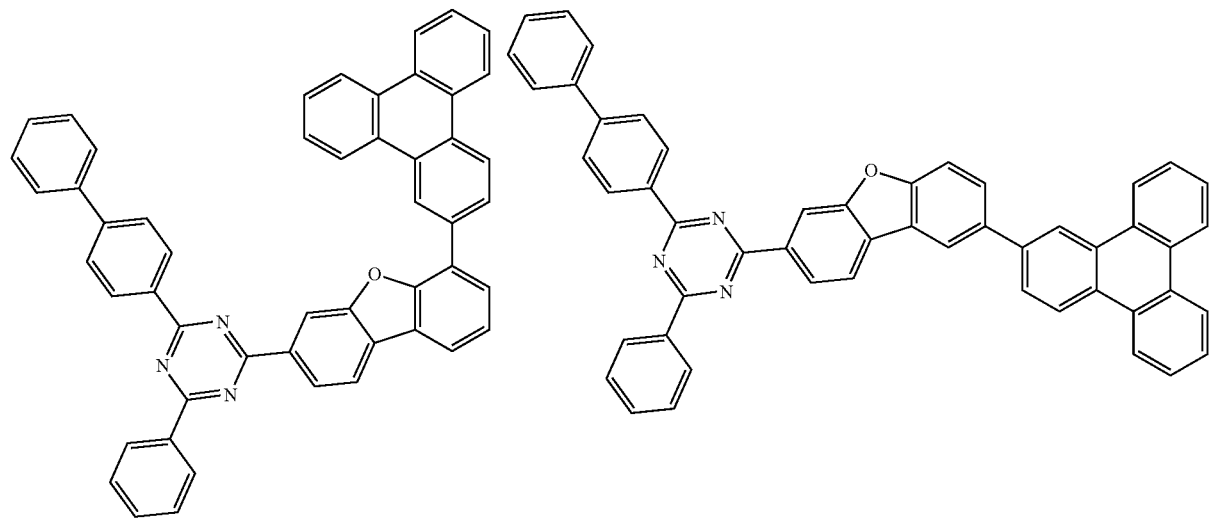

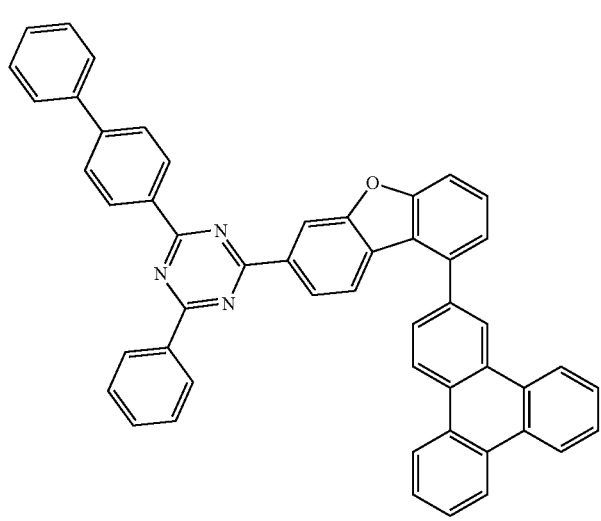
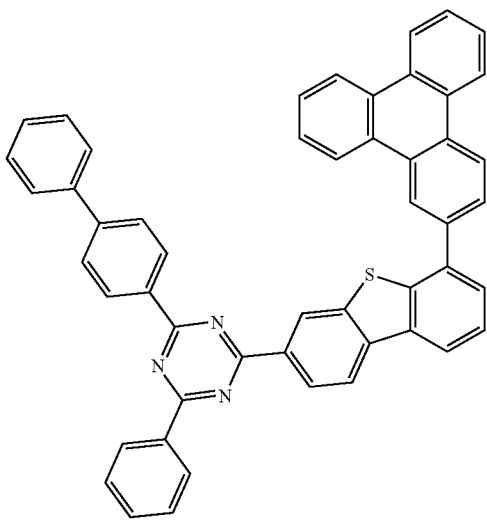
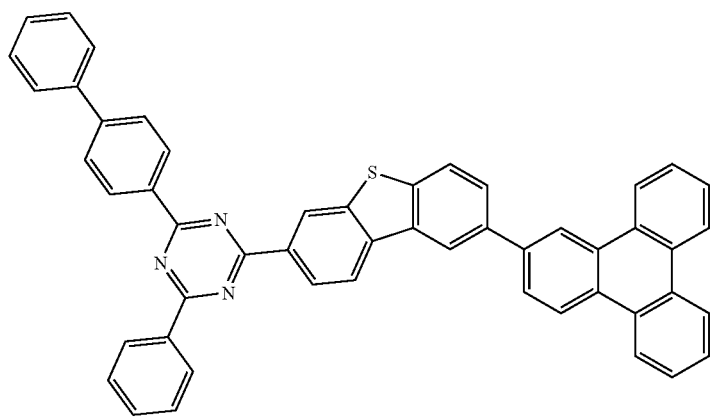
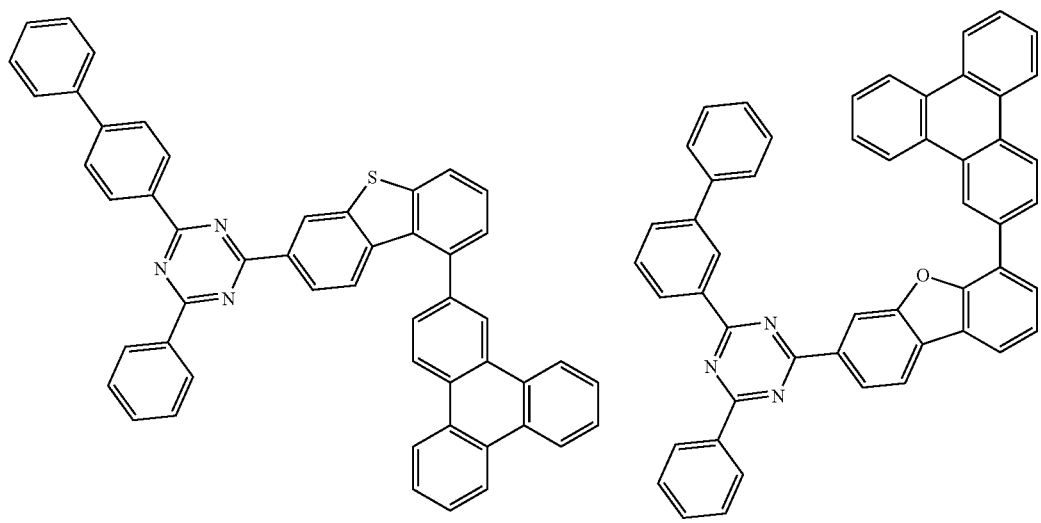

-continued
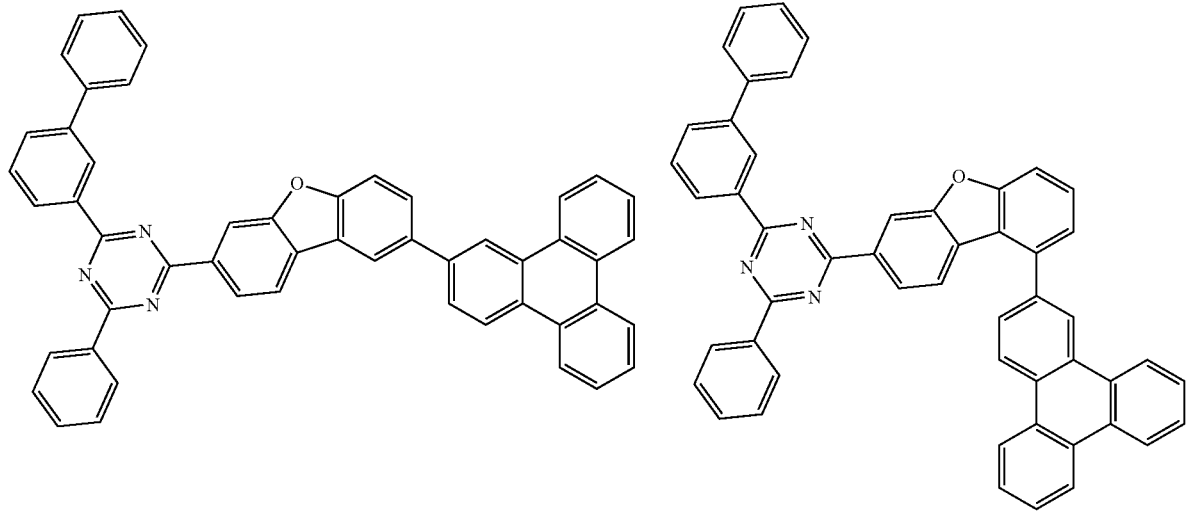
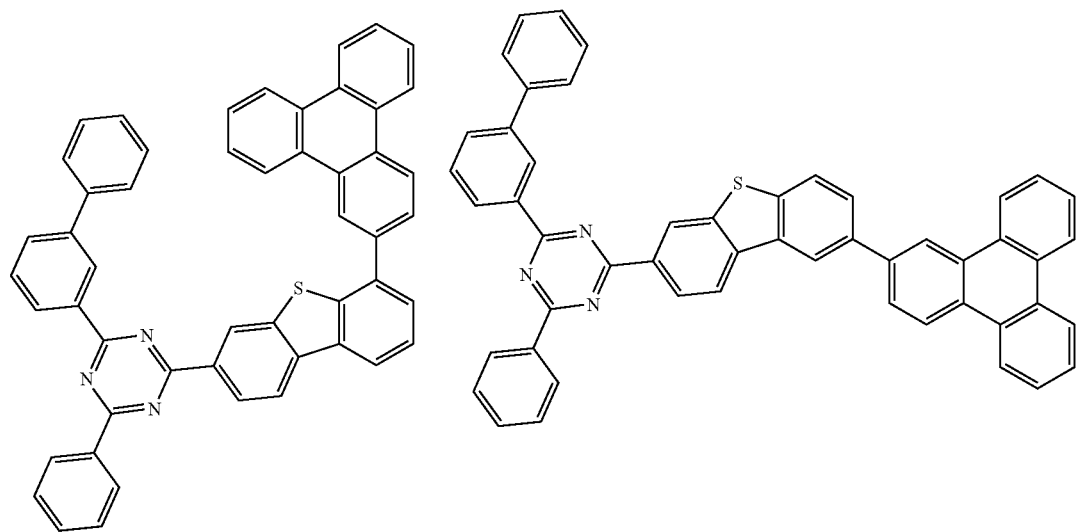
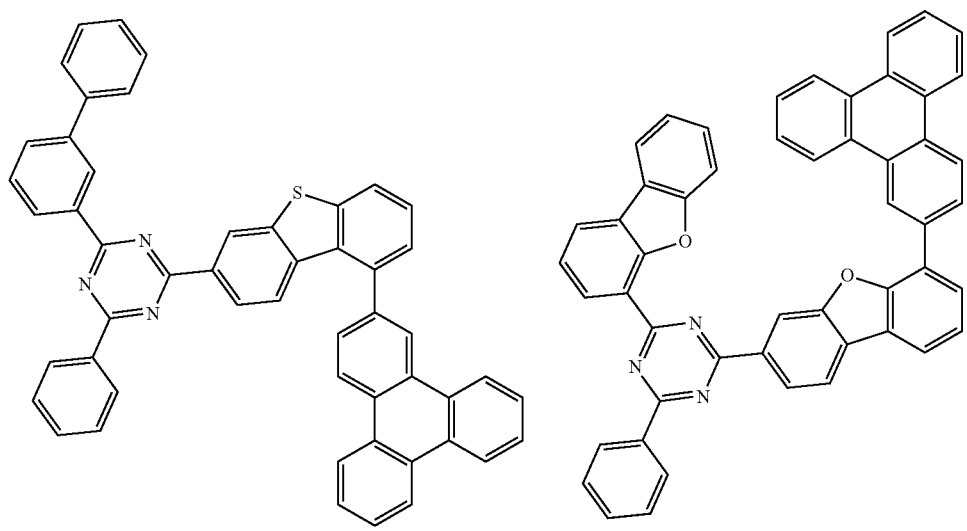

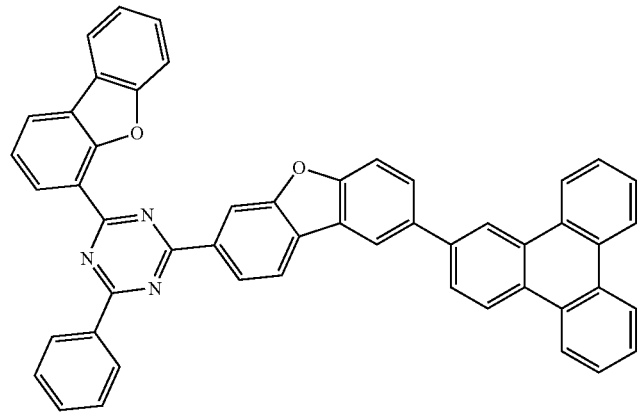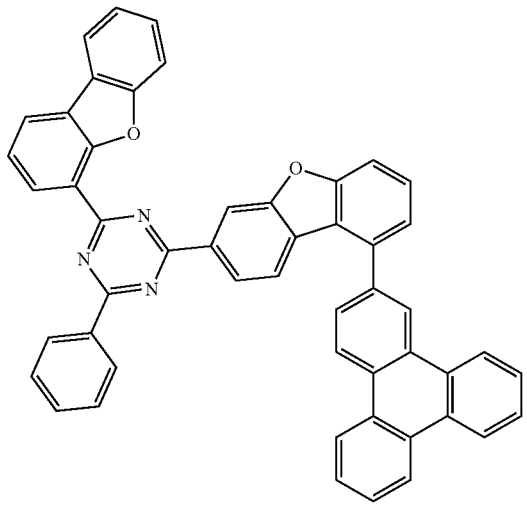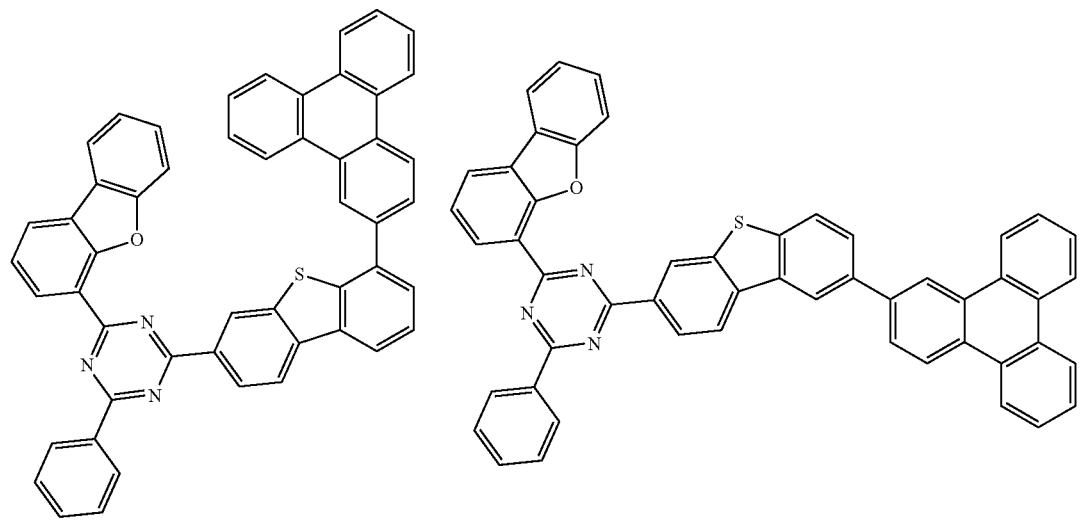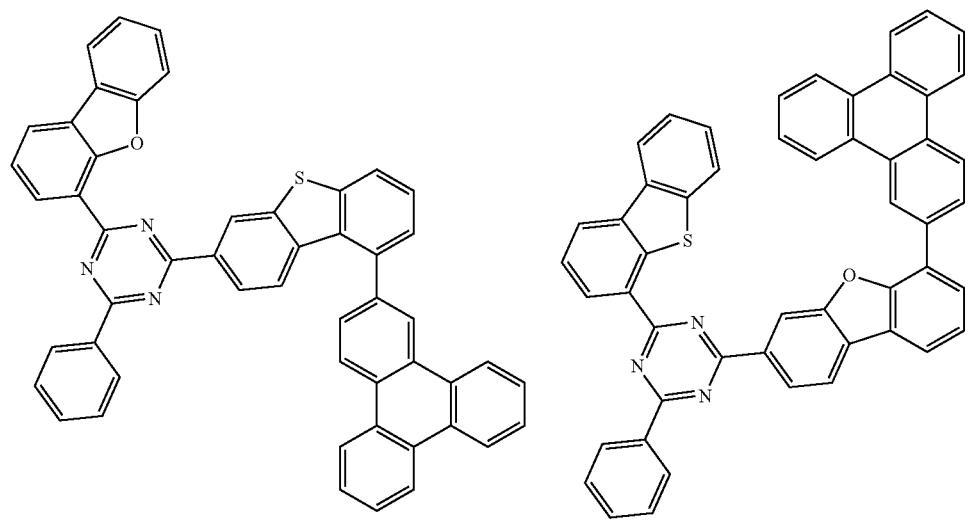

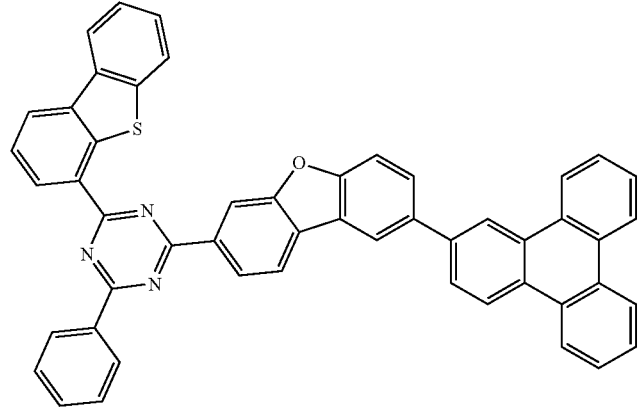
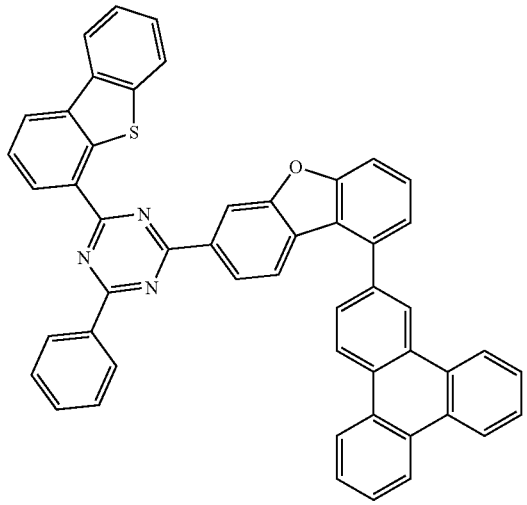
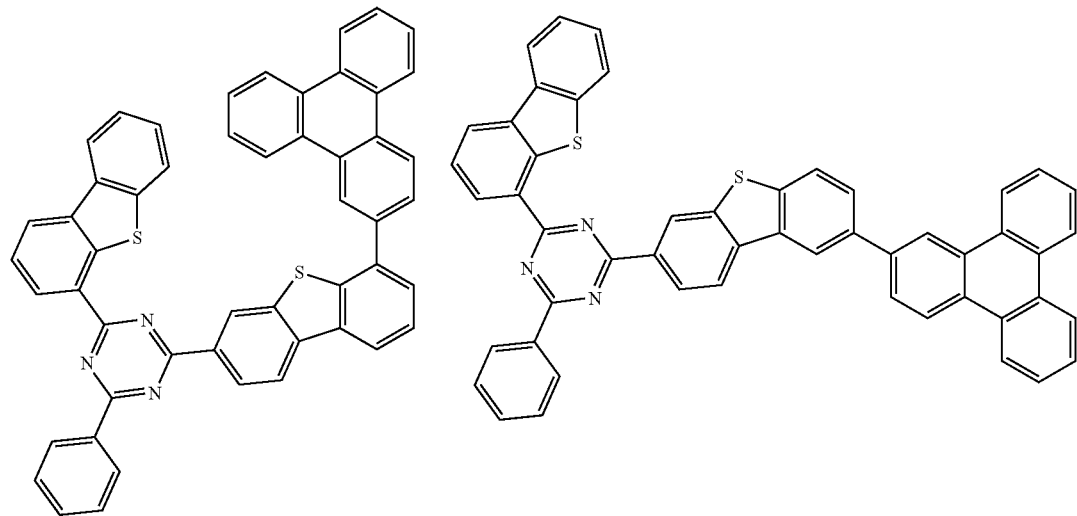
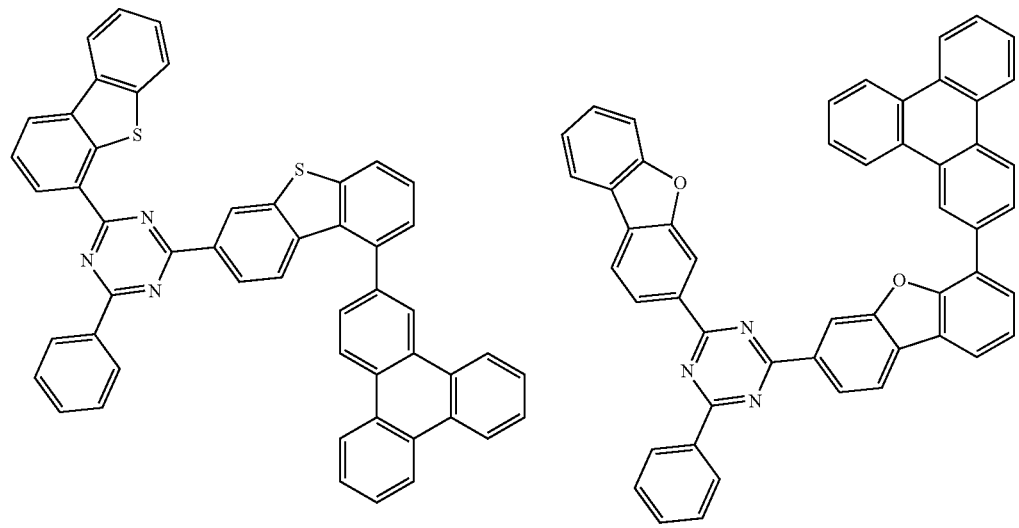

-continued
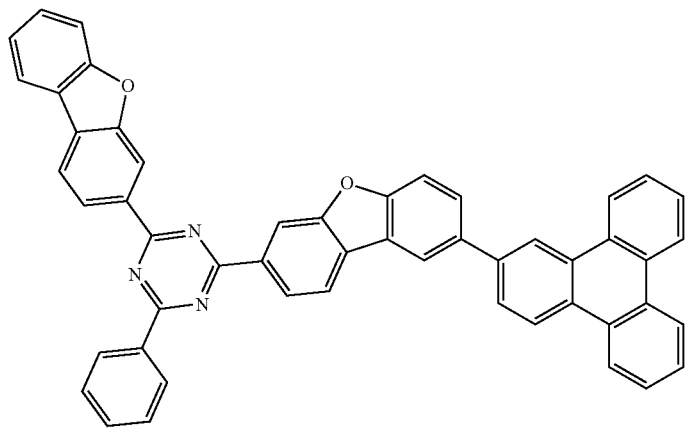
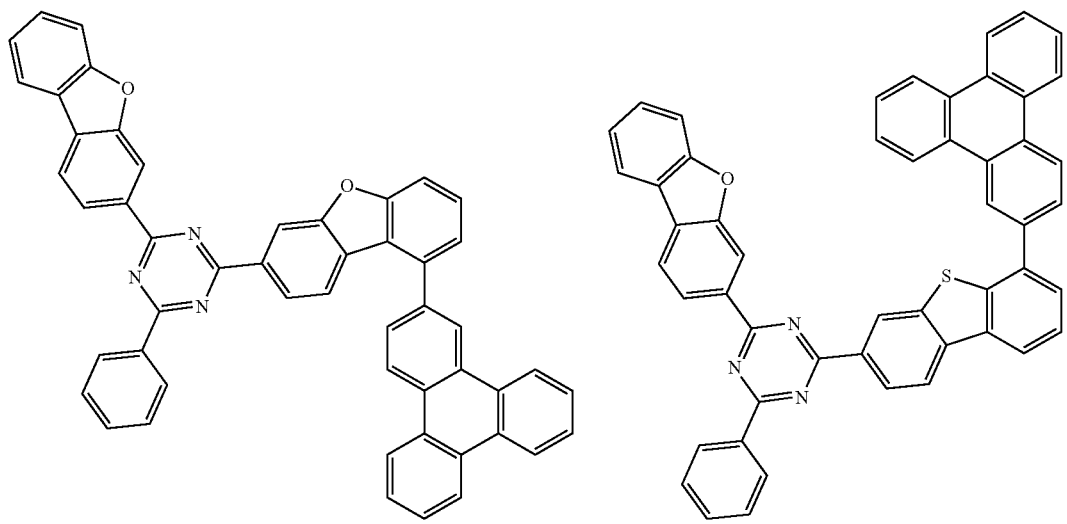
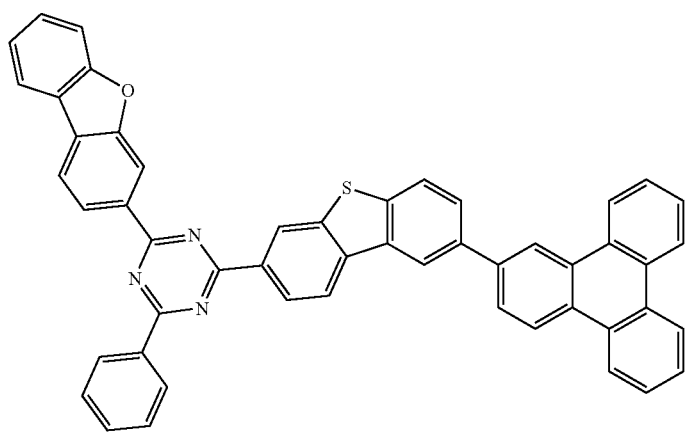

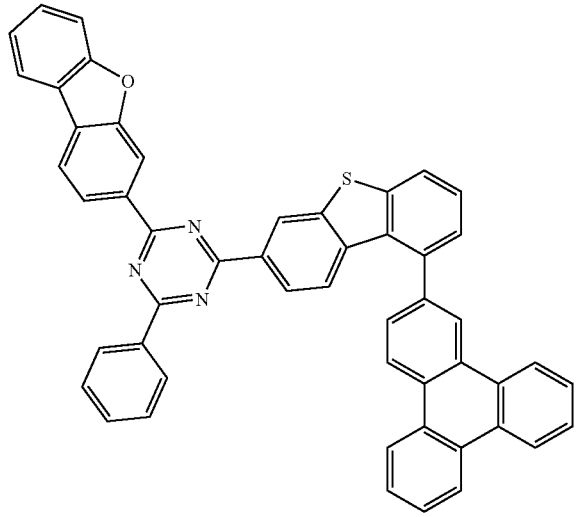
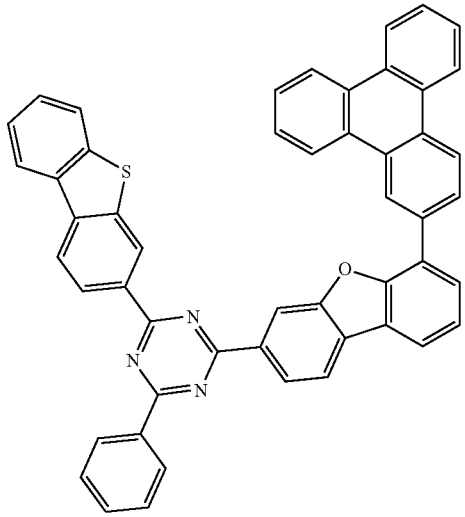
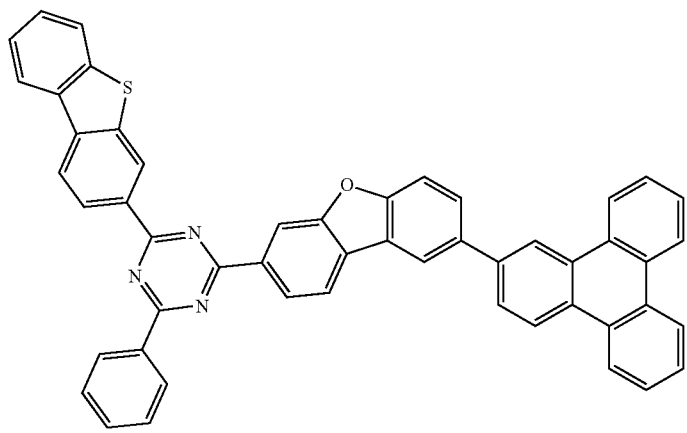
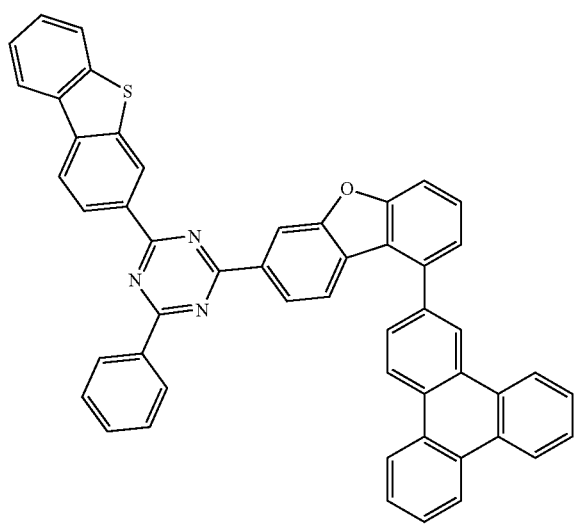
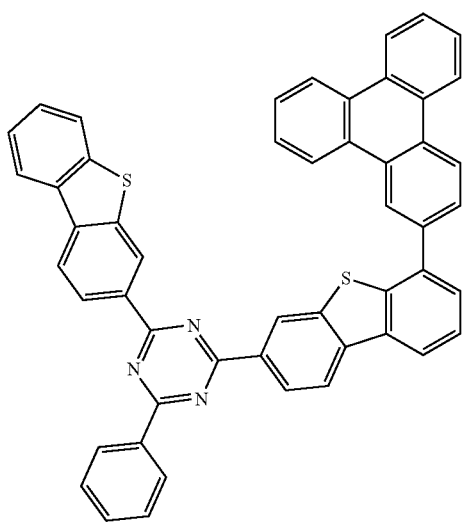

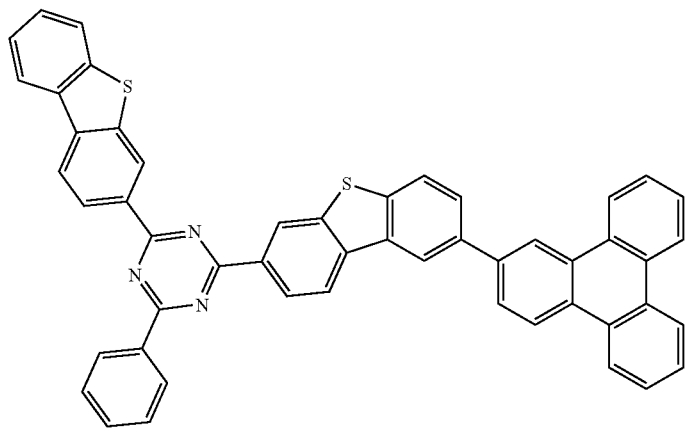
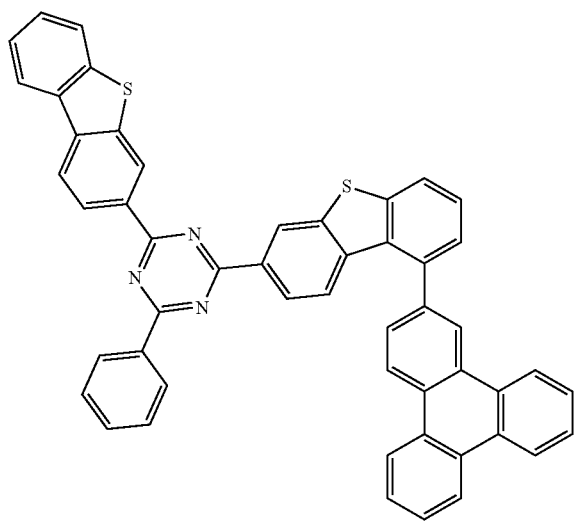
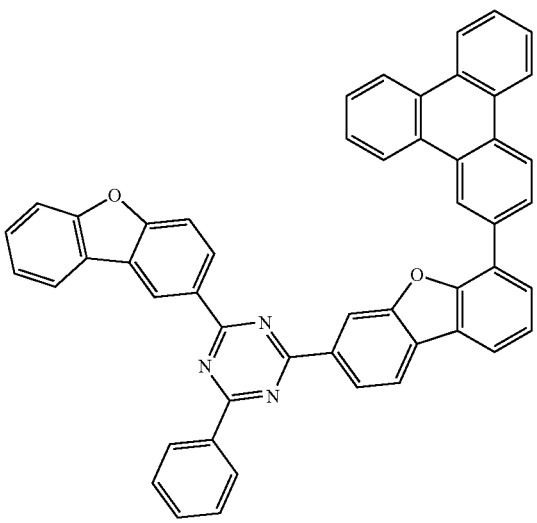
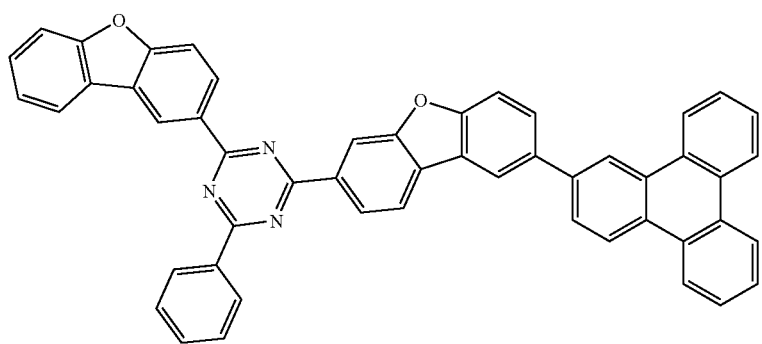

-continued
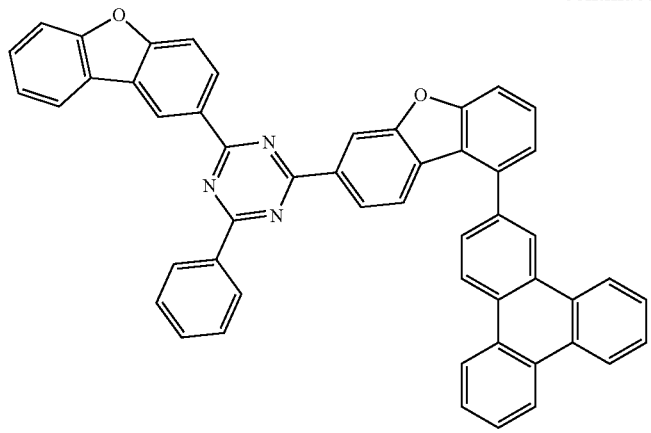
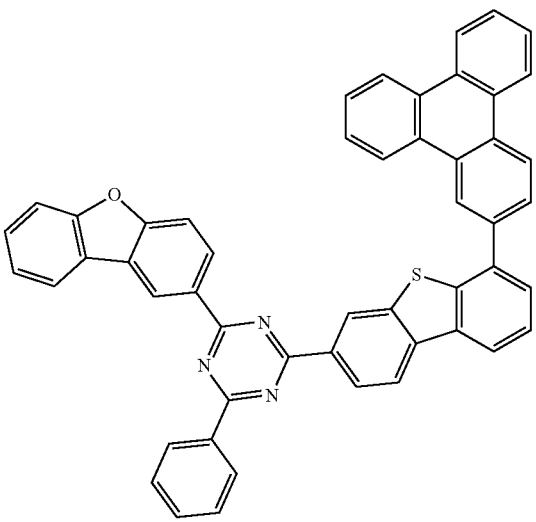
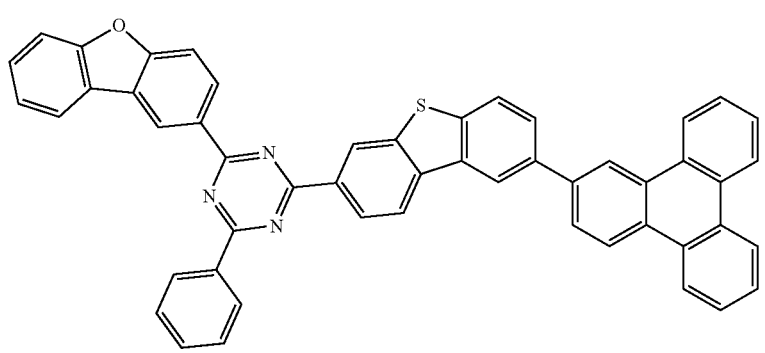
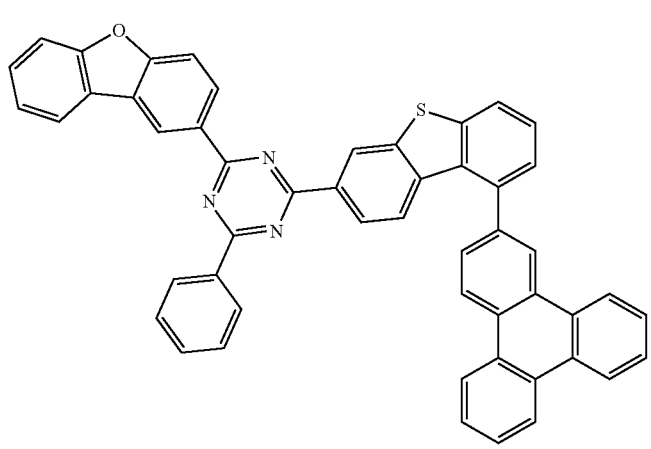
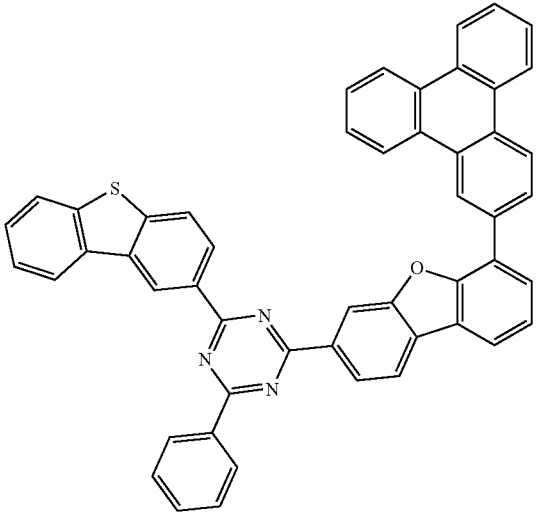
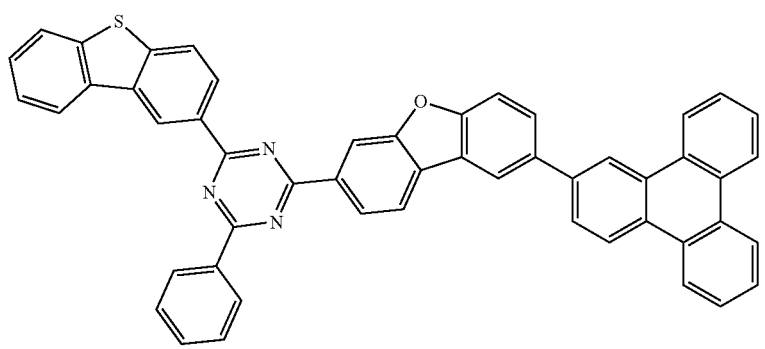

-continued
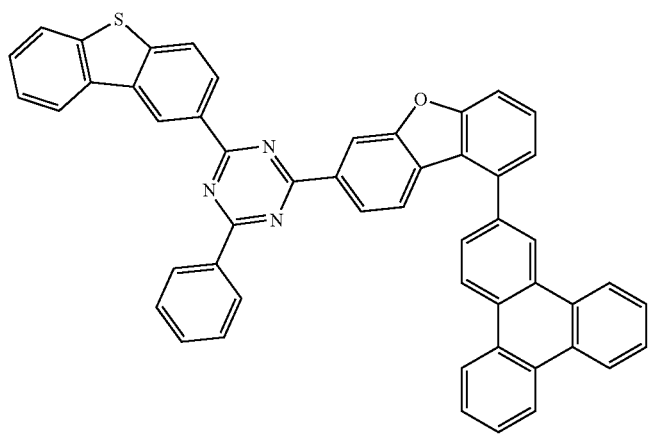
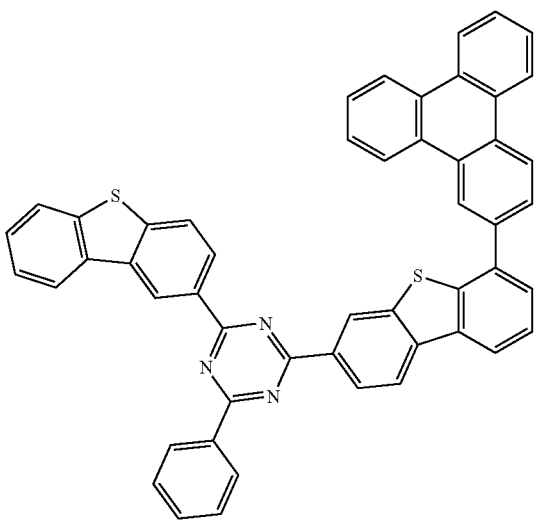
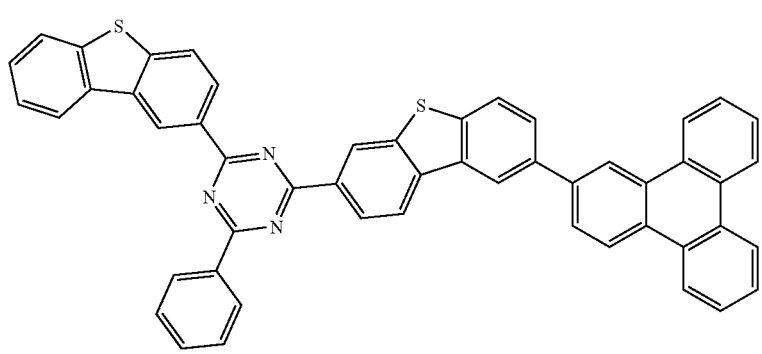
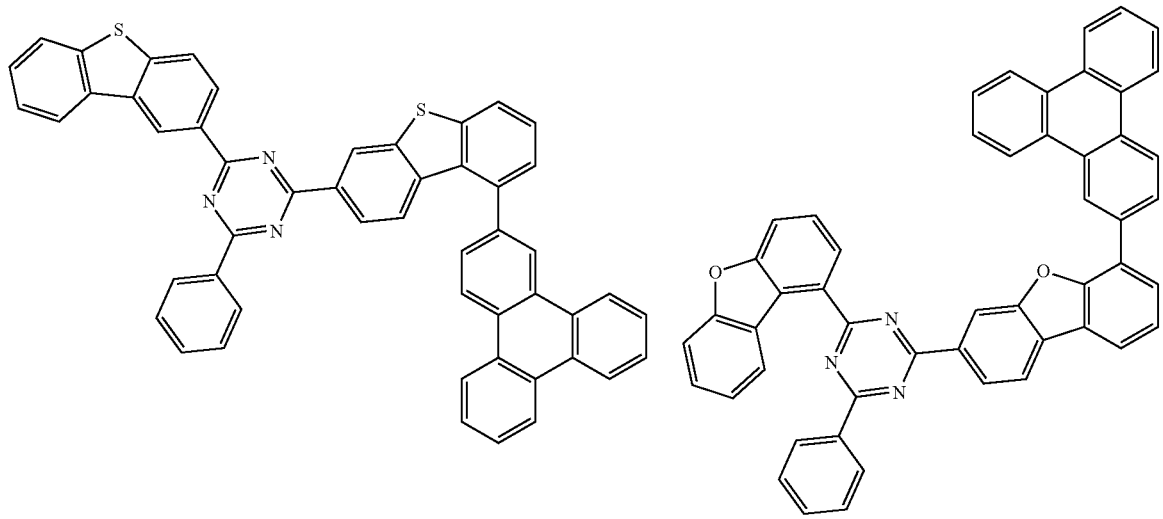
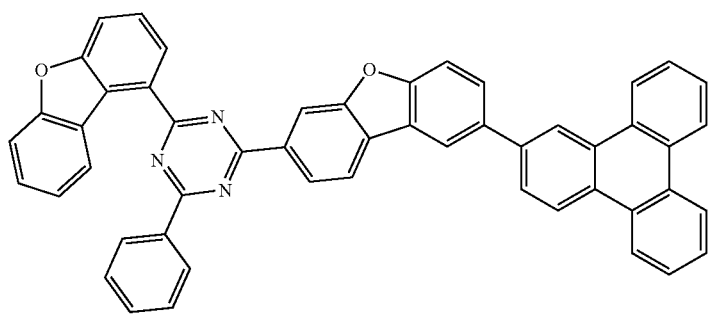

-continued
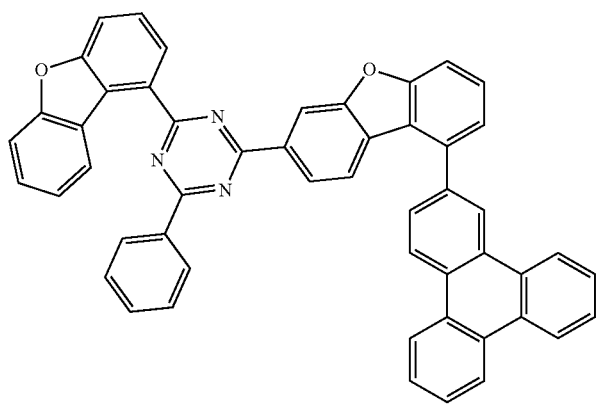
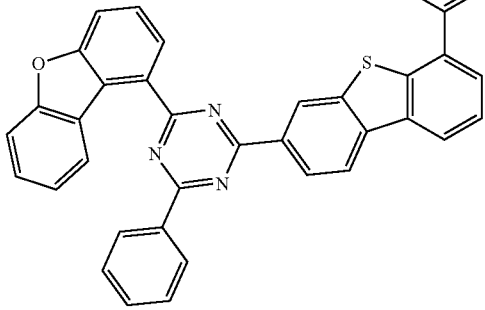
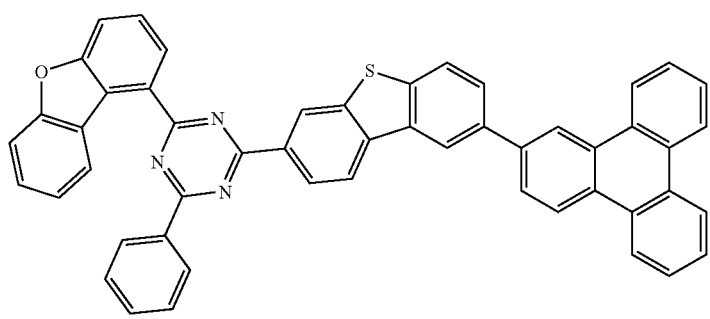
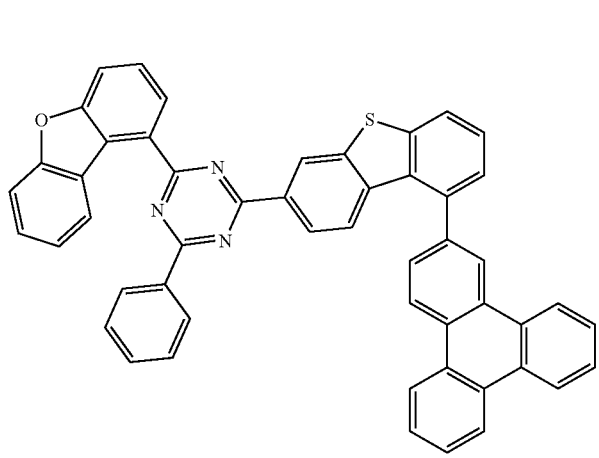
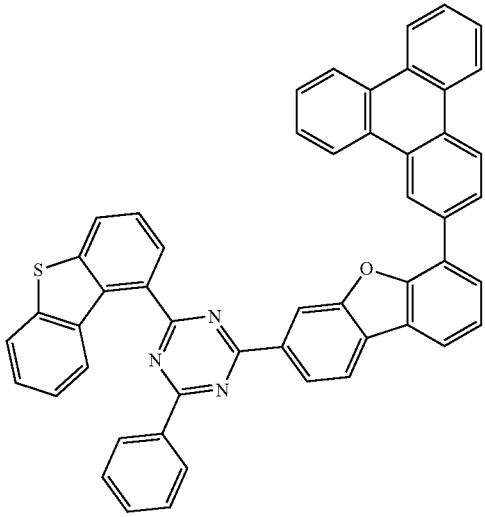
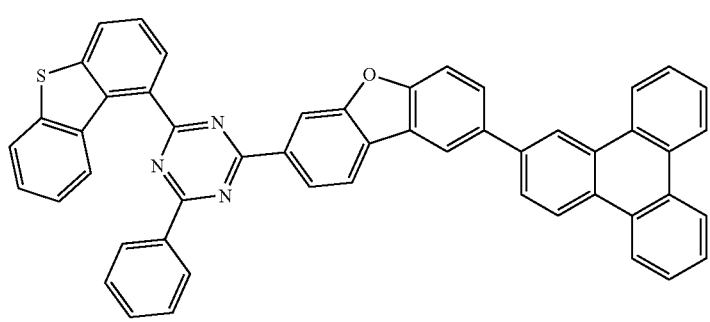

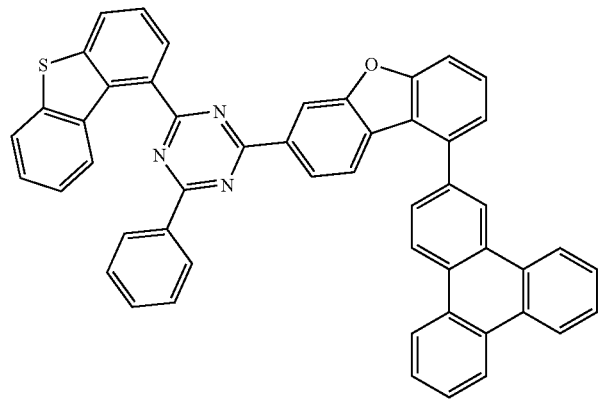
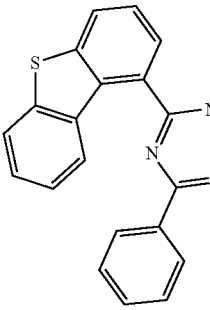
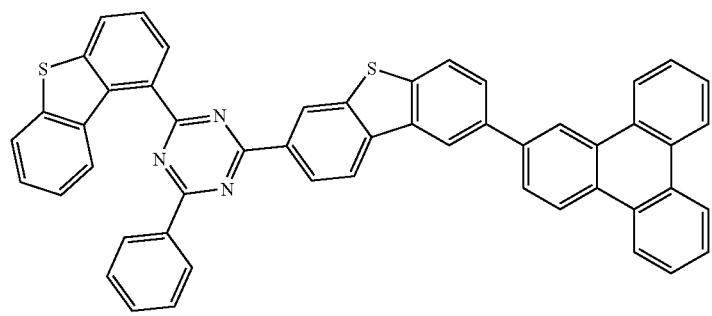
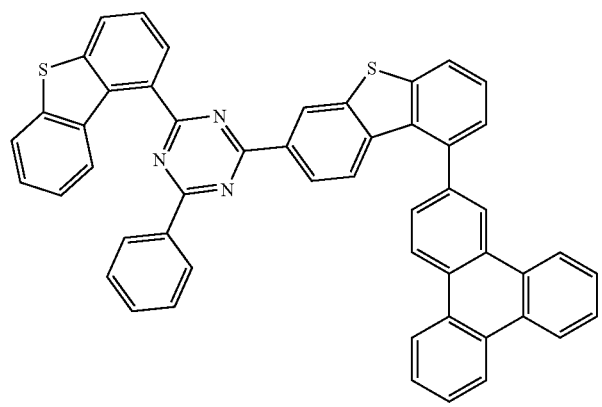
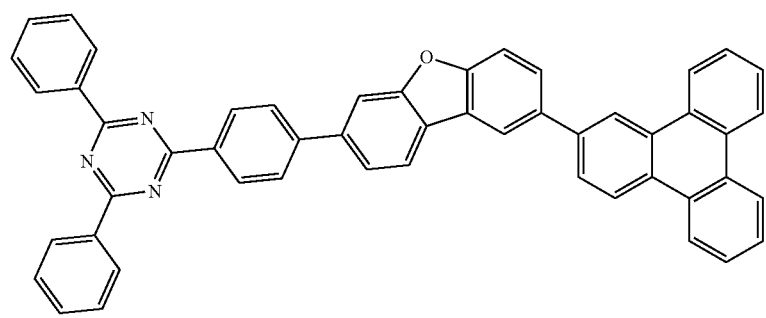

-continued
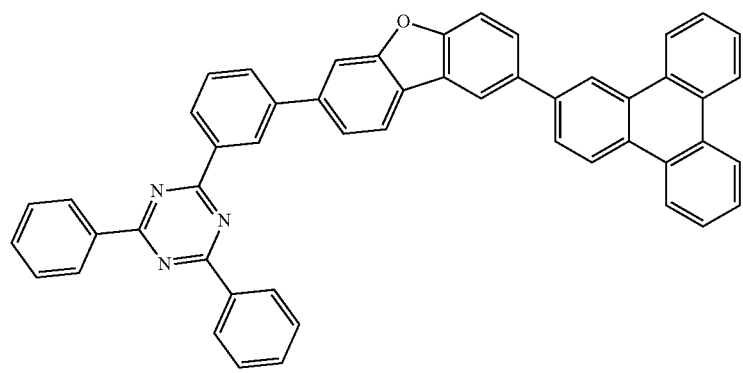
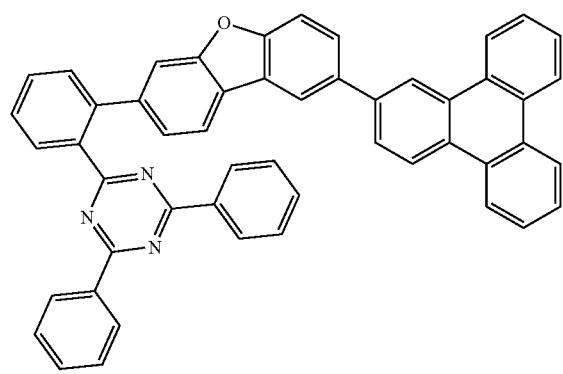
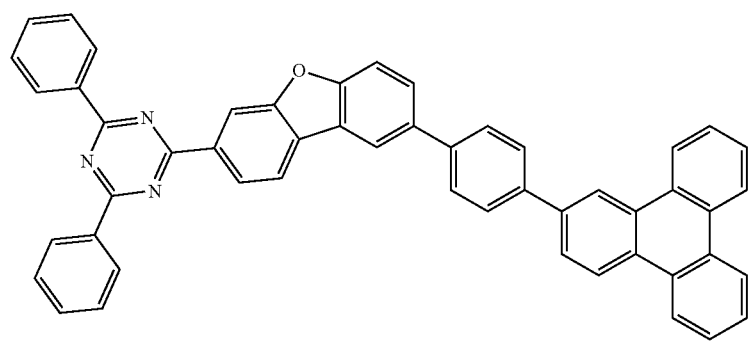
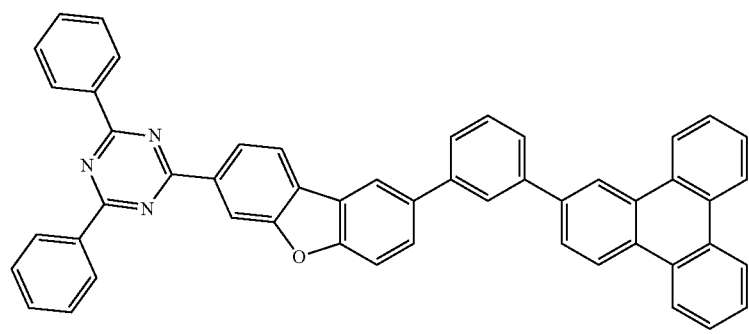

-continued
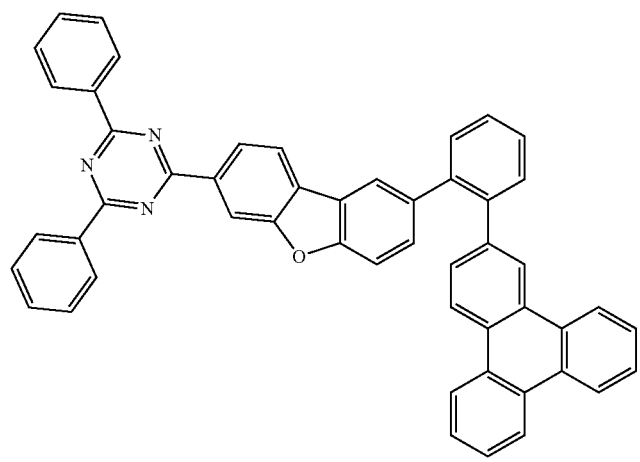
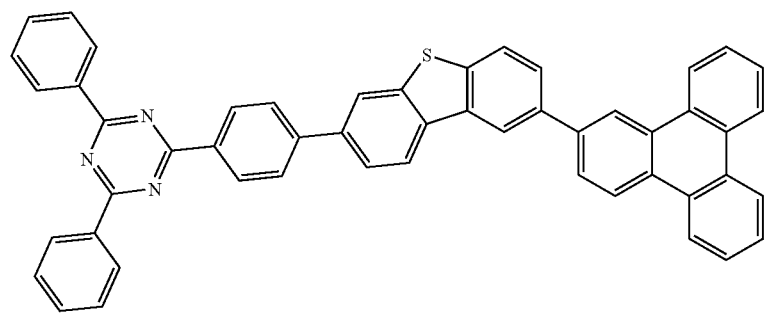
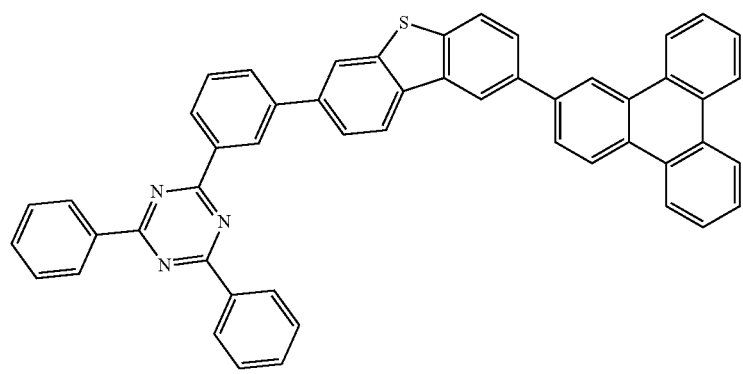
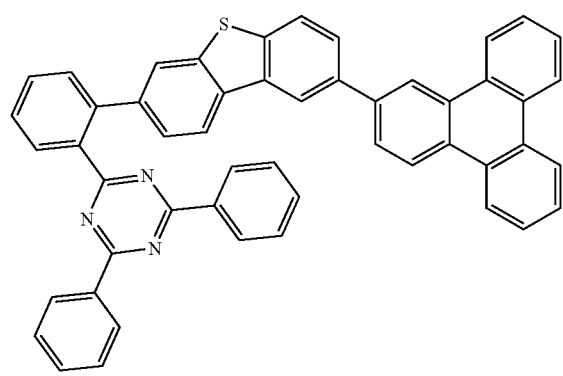

-continued
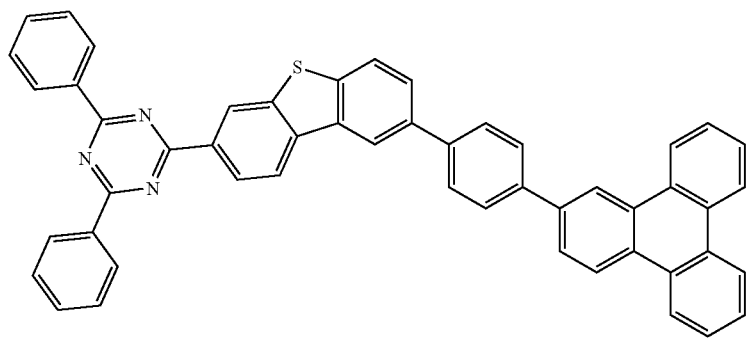
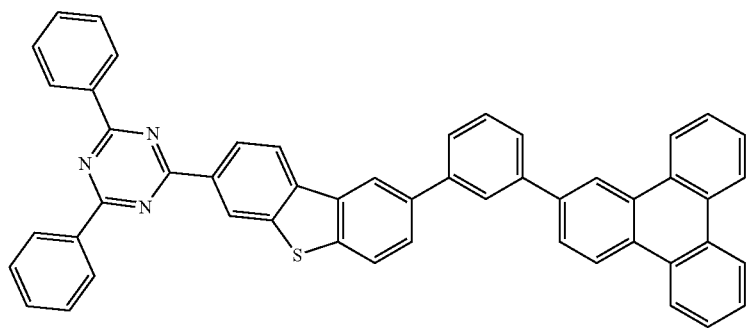
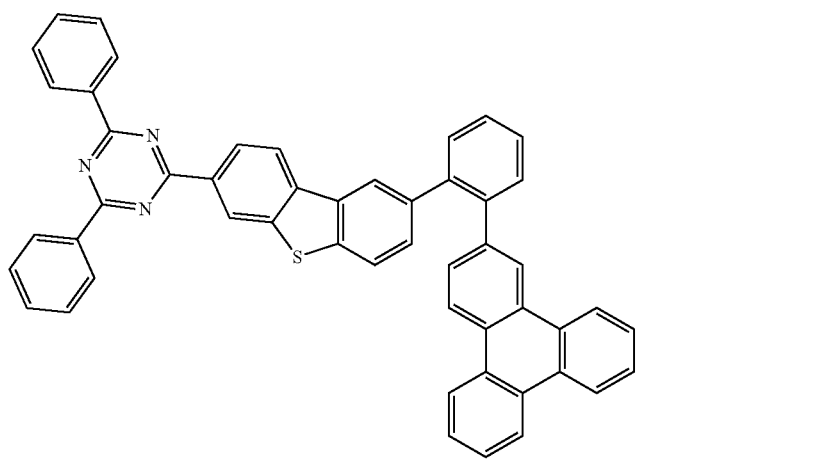
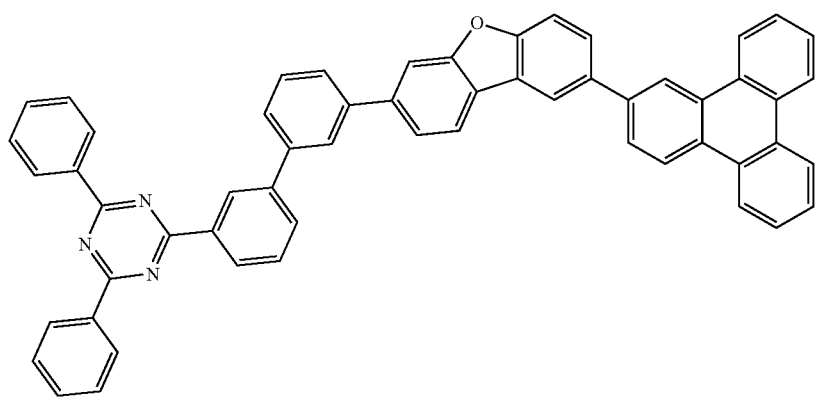

-continued
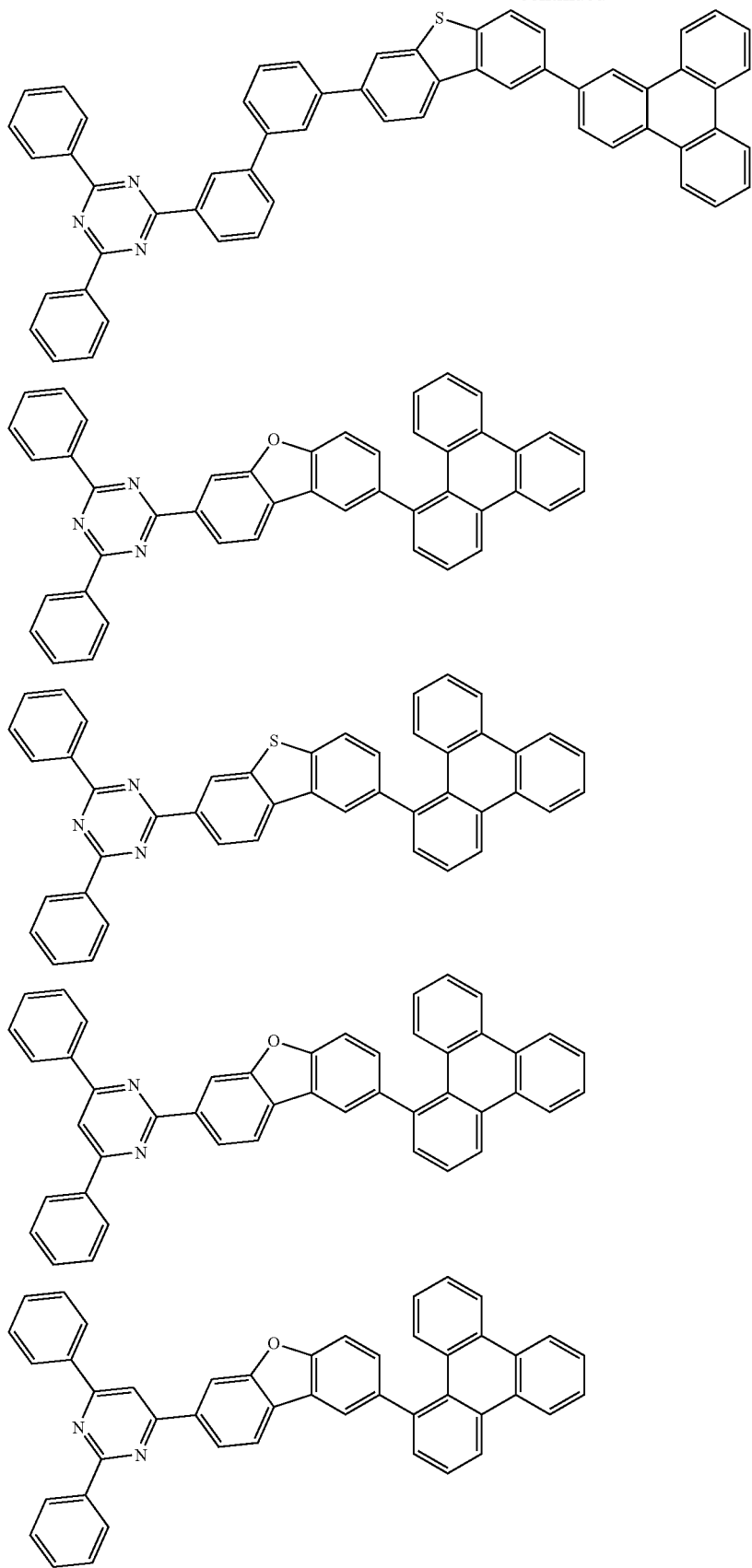

Meanwhile, the compound represented by Chemical Formula 1 can be prepared, for example, according to the preparation method as shown in the following Reaction Scheme 1. The preparation method can be further specified in the Preparation Examples described hereinafter.

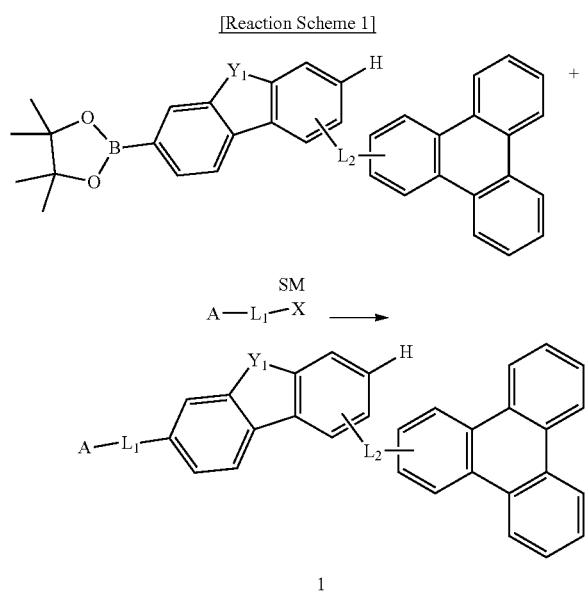

[Reaction Scheme 1]

wherein, in Reaction Scheme 1, each X is independently a halogen, preferably bromo or chloro, and the definitions of the remaining substituents are the same as those defined above.

The aforementioned reaction is a step of preparing a compound represented by Chemical Formula 1 by introducing a substituent A to the starting material by a Suzuki coupling reaction. At this time, the Suzuki coupling reaction is preferably carried out in the presence of a palladium catalyst and a base, and the reactive group for the reaction can be changed to a reactive group known in the art. The above preparation method may be further specified in the preparation examples described hereinafter.

In another embodiment of the invention, there is provided an organic light emitting device including a compound represented by Chemical Formula 1 described above. As an example, there is provided an organic light emitting device including: a first electrode; a second electrode provided to face the first electrode; and one or more organic material layers provided between the first electrode and the second electrode, wherein one or more layers of the organic material layers include the compound represented by Chemical Formula 1.

The organic material layer of the organic light emitting device of the present invention may have a single-layer structure, or it may have a multilayered structure in which two or more organic material layers are stacked. For example, the organic light emitting device of the present invention may have a structure including a hole injection layer, a hole transport layer, an electron blocking layer, a light emitting layer, an electron transport layer, an electron injection layer, and the like as the organic material layer. However, the structure of the organic light emitting device is not limited thereto, and it may include a smaller number of organic layers.

Further, the organic material layer may include a light emitting layer, wherein the light emitting layer includes the compound represented by Chemical Formula 1. In particular, the compound according to the present invention can be used as a host of the light emitting layer. Specifically, the compound according to the present invention can be used as a green phosphorescent host of the light emitting layer.

In addition, the organic material layer may include a light emitting layer and the light emitting layer may include two or more types of hosts, wherein one of the hosts may be a compound represented by Chemical Formula 1.

Further, the organic material layer may include an electron transport layer or an electron injection layer, wherein the electron transport layer or the electron injection layer may include the compound represented by Chemical Formula 1.

The organic material layer of the organic light emitting device according to the present invention may have a single-layer structure, or it may have a multilayered structure in which two or more organic material layers are stacked. For example, the organic light emitting device of the present invention may have a structure further including a hole injection layer and a hole transport layer provided between the first electrode and the light emitting layer, and an electron transport layer and an electron injection layer provided between the light emitting layer and the second electrode, in addition to the light emitting layer. However, the structure of the organic light emitting device is not limited thereto, and it may include a smaller number of organic layers or a larger number of organic layers.

The organic light emitting device according to the present invention may be a normal type of organic light emitting device in which an anode, one or more organic material layers, and a cathode are sequentially stacked on a substrate, wherein the first electrode is an anode and the second electrode is a cathode. Further, the organic light emitting device according to the present invention may be an inverted type of organic light emitting device in which a cathode, one or more organic material layers, and an anode are sequentially stacked on a substrate, wherein the first electrode is a cathode and the second electrode is an anode. For example, the structure of an organic light emitting device according to an embodiment of the present disclosure is illustrated in FIGS. 1 and 2.

FIG. 1 shows an example of an organic light emitting device including a substrate 1, an anode 2, a light emitting layer 3, and a cathode 4. In such a structure, the compound represented by Chemical Formula 1 may be included in the light emitting layer.

FIG. 2 shows an example of an organic light emitting device including a substrate 1, an anode 2, a hole injection layer 5, a hole transport layer 6, an electron blocking layer 7, a light emitting layer 3, an electron transport layer 8, an electron injection layer 9, and a cathode 4. In such a structure, the compound represented by Chemical Formula 1 may be included in one or more layers of the hole injection layer, the hole transport layer, the light emitting layer, and the electron transport layer. Preferably, the compound represented by Chemical Formula 1 may be included in the light emitting layer.

The organic light emitting device according to the present invention may be manufactured by materials and methods known in the art, except that one or more layers of the organic material layers include the compound represented by Chemical Formula 1. Moreover, when the organic light emitting device includes a plurality of organic material layers, the organic material layers may be formed of the same material or different materials.

For example, the organic light emitting device according to the present invention can be manufactured by sequentially stacking a first electrode, an organic material layer, and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, an organic material layer, and an anode material on a substrate.

Further, the compound represented by Chemical Formula 1 may be formed into an organic layer by a solution coating method as well as a vacuum deposition method at the time of manufacturing an organic light emitting device. Herein, the solution coating method means spin coating, dip coating, doctor blading, inkjet printing, screen printing, a spray method, roll coating, or the like, but is not limited thereto.

In addition to such a method, the organic light emitting device may be manufactured by sequentially depositing a cathode material, an organic material layer, and an anode material on a substrate (International Publication WO2003/012890). However, the manufacturing method is not limited thereto.

As an example, the first electrode is an anode and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chromium, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; and a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole-injecting effect to the light emitting layer or the light emitting material, prevents excitons produced in the light emitting layer from moving to an electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrin, oligothiophene, an arylamine-based organic material, a hexanitrilehexaazatriphenylene-based organic material, a quinacridone-based organic material, a perylene-based organic material, anthraquinone, a polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, and which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The electron blocking layer refers to a layer that is formed on the hole transport layer and is preferably disposed in contact with the light emitting layer to adjust hole mobility, prevent excessive movement of electrons, and increase the probability of hole-electron bonding, thereby serving to improve the efficiency of an organic light emitting element. The electron blocking layer includes an electron blocking material, and examples of such electron blocking materials include arylamine-based organic materials and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples thereof include an 8-hydroxy-quinoline aluminum complex ($Alq_3$); a carbazole-based compound; a dimerized styryl compound; BAlq; a 10-hydroxybenzoquinoline-metal compound; a benzoxazole, benzothiazole, and benzimidazole-based compound; a poly(p-phenylene vinylene)(PPV)-based polymer; a spiro compound; polyfluorene, rubrene, and the like, but are not limited thereto.

The light emitting layer may include a host material and a dopant material as described above. The host material may include the compound represented by Chemical Formula 1. Alternatively, the light emitting layer includes two or more kinds of hosts, wherein one of the hosts is a compound represented by Chemical Formula 1, and the other host material may be a fused aromatic ring derivative, a heterocyclic-containing compound, or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto. For example, the light emitting layer may include two kinds of hosts, wherein the two kinds of hosts may be a compound represented by Chemical Formula 1 and a biscarbazole derivative, respectively.

The dopant material may be an aromatic amine derivative, a styrylamine Compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene, and the like, which have an arylamino group. The styrylamine compound is a compound where at least one arylvinyl group is substituted in a substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which can receive electrons well from a cathode and transfer the electrons to a light emitting layer and has large mobility for electrons. Specific examples thereof include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato)gallium, bis(10-hydroxybenzo[h]quinolinato)beryllium, bis(10-hydroxybenzo[h]quinolinato) zinc, bis(2-methyl-8-quinolinato)chlorogallium, bis(2-methyl-8-quinolinato)(o-cresolato)gallium, bis(2-methyl-8-quinolinato) (1-naphtholato) aluminum, bis(2-methyl-8-quinolinato) (2-naphtholato)gallium, and the like, but are not limited thereto.

The organic light emitting device according to the present invention may be a front side emission type, a backside emission type, or a double-sided emission type according to the used material.

In addition, the compound represented by Chemical Formula 1 may be included in an organic solar cell or an organic transistor in addition to an organic light emitting device.

The preparation of the compound represented by Chemical Formula 1 and the organic light emitting device containing the same will be described in detail in the following examples. However, these examples are presented for illustrative purposes only and are not intended to limit the scope of the present invention.

Preparation Example A: Preparation of Intermediate Compound P-6

1) Preparation of Compound P-1

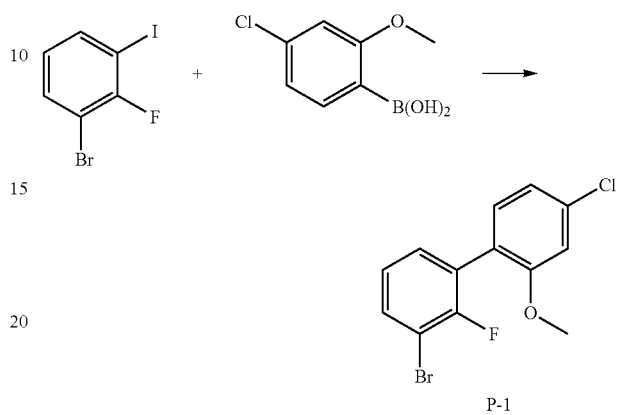

1-bromo-2-fluoro-3-iodobenzene (100 g, 333.5 mmol) and (4-chloro-2-methoxyphenyl)boronic acid (62.2 g, 333.5 mmol) were dissolved in 800 ml of tetrahydrofuran (THF). A 2 M sodium carbonate ($Na_2CO_3$) solution (500 mL), tetrakis(triphenyl-phosphino)palladium(0) [$Pd(PPh_3)_4$] (7.7 g, 6.7 mmol) were added thereto and refluxed for 12 hours. After completion of the reaction, the reaction mixture was cooled to room temperature and extracted three times with water and toluene. The toluene layer was separated, dried over magnesium sulfate, and filtered. The filtrate was distilled under reduced pressure, and the resulting mixture was recrystallized three times using chloroform and ethanol to give Compound P-1 (53.7 g, yield: 51%).

MS: $[M+H]^+$=314

2) Preparation of Compound P-2

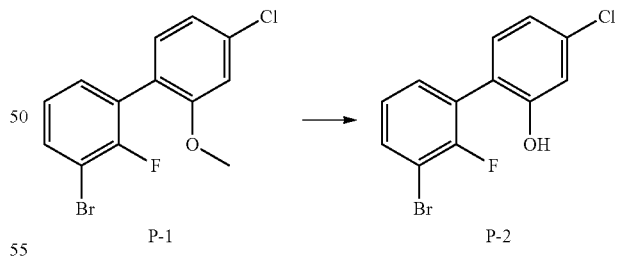

Compound P-1 (50.0 g, 158.5 mmol) was dissolved in dichloromethane (600 ml) and then cooled to 0° C. Boron tribromide (15.8 ml, 166.4 mmol) was slowly added dropwise and then stirred for 12 hours. After completion of the reaction, the reaction mixture was washed three times with water, dried over magnesium sulfate, and filtered. The filtrate was distilled under reduced pressure and purified by column chromatography to give Compound P-2 (47.4 g, yield: 99%).

MS: $[M+H]^+$=300

3) Preparation of Compound P-3

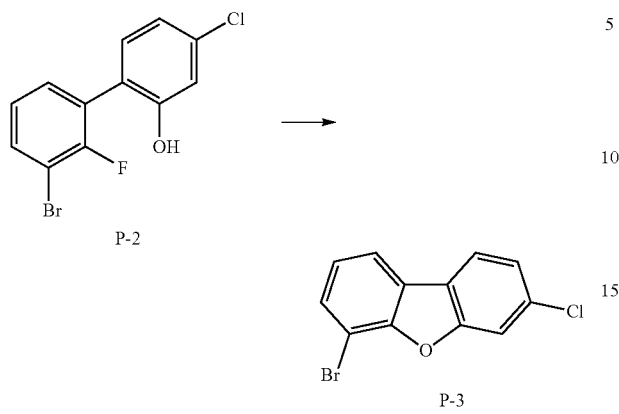

Compound P-2 (40.0 g, 132.7 mmol) was dissolved in distilled dimethylformamide (DMF) (400 ml). The resulting solution was cooled to 0° C. and sodium hydride (3.5 g, 145.9 mmol) was slowly added dropwise thereto. After stirring for 20 minutes, the reaction mixture was stirred at 100° C. for 1 hour. After completion of the reaction, the reaction product was cooled to room temperature and 100 ml of ethanol was slowly added thereto. The mixture was distilled under reduced pressure and then recrystallized with chloroform and ethyl acetate to give Compound P-3 (30.3 g, yield: 81%).

MS: $[M+H]^+$=280

4) Preparation of Compound P-4

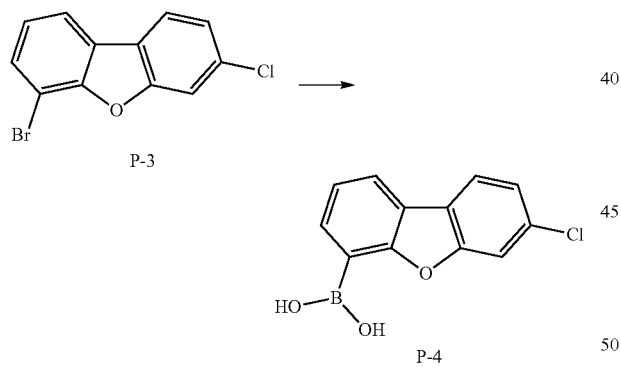

After Compound P-3 (30.0 g, 106.6 mmol) was dissolved in tetrahydrofuran (300 ml), the reaction temperature was lowered to −78° C. and 1.7 M tert-butyllithium (t-BuLi) (62.7 ml, 106.6 mmol) was slowly added thereto. After stirring at the same temperature for 1 hour, triisopropyl borate (B(OiPr)$_3$) (28.3 ml, 213.1 mmol) was added thereto. The mixture was stirred for 3 hours while gradually raising the temperature to room temperature. A 2N aqueous hydrochloric acid solution (200 ml) was added to the reaction mixture and then stirred at room temperature for 1.5 hours. The resulting precipitate was filtered, washed sequentially with water and ethyl ether, and then dried in vacuum. After drying, the result was dispersed in ethyl ether, stirred for 2 hours, then filtered and dried to prepare Compound P-4 (24.4 g, yield: 93%).

MS: $[M+H]^+$=247

5) Preparation of Compound P-5

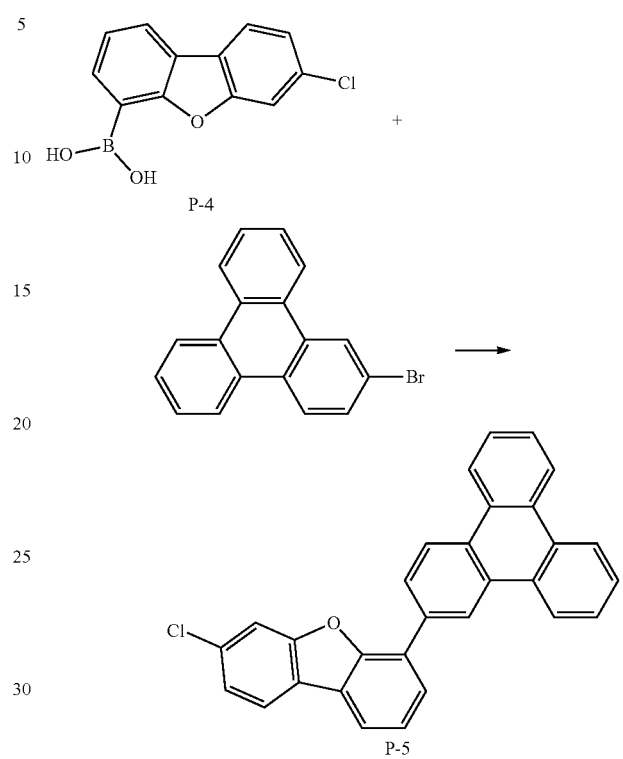

Compound P-4 (20.0 g, 81.3 mmol) and 2-bromotriphenylene (24.9 g, 81.3 mmol) were dispersed in tetrahydrofuran (200 ml) and then 2M aqueous potassium carbonate solution (aq. K$_2$CO$_3$) (122 ml, 243.9 mmol) was added and tetrakis(triphenyl-phosphino)palladium [Pd(PPh$_3$)$_4$] (2.8 g, 3 mol %) was added, and then the mixture was stirred and refluxed for 5 hours. The reaction temperature was lowered to room temperature and the resulting solid was filtered. The filtered solid was recrystallized with chloroform and ethyl acetate, and filtered and dried to give compound P-5 (23.0 g, yield 66%).

MS: $[M+H]^+$=429

6) Preparation of Compound P-6

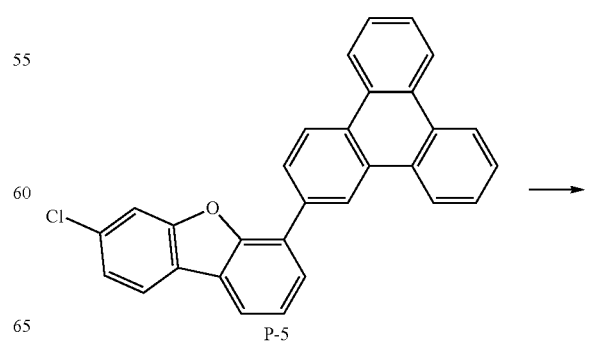

-continued

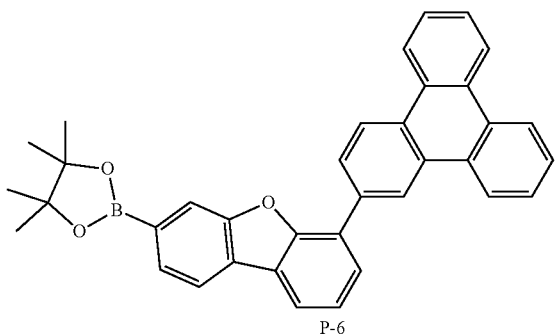

Compound P-5 (20.0 g, 46.7 mmol), bis(pinacolato)diboron (13.0 g, 51.4 mmol) and potassium acetate (9.2 g, 93.4 mmol) were mixed under a nitrogen atmosphere, and the mixture was added to 200 ml dioxane and heated while stirring. Bis(dibenzylideneacetone) palladium (0.8 g, 1.4 mmol) and tricyclohexylphosphine (0.8 g, 2.8 mmol) were added thereto under refluxing conditions, and the mixture was heated and stirred for 3 hours. After completion of the reaction, the reaction mixture was cooled to room temperature and then filtered. Water was poured into the filtrate and extracted with chloroform. The organic layer was dried over anhydrous magnesium sulfate. After distillation under reduced pressure, recrystallization from ethanol yielded Compound P-6 (18.2 g, 75%).

MS: [M+H]$^+$=521

Preparation Example B: Preparation of Intermediate Compound T-6

1) Preparation of Compound T-1

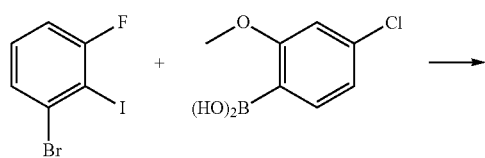

Compound T-1 (65.3 g, yield: 62%) was prepared in the same manner as in the preparation of Compound P-1 in Preparation Example A, except that (4-chloro-2-methoxyphenyl)boronic acid (62.2 g, 333.5 mmol) was used instead of (5-chloro-2-methoxyphenyl) boronic acid(62.2 g, 333.5 mmol).

MS: [M+H]$^+$=314

2) Preparation of Compound T-2

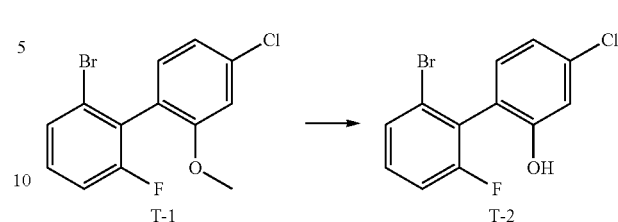

Compound T-2 (43.0 g, yield: 90%) was prepared in the same manner as the preparation of Compound P-2 in Preparation Example A, except that Compound T-1 (50.0 g, 158.5 mmol) was used instead of Compound P-1 (50.0 g, 158.5 mmol).

MS: [M+H]$^+$=300

3) Preparation of Compound T-3

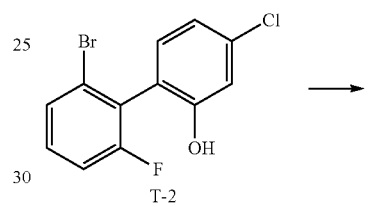

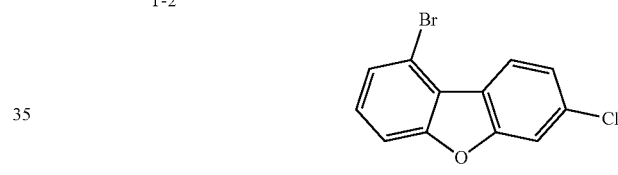

Compound T-3 (30.6 g, yield: 82%) was prepared in the same manner as in the preparation of Compound P-3 in Preparation Example A, except that Compound T-2 (40.0 g, 132.7 mmol) was used instead of Compound P-2 (40.0 g, 132.7 mmol).

MS: [M+H]$^+$=280

4) Preparation of Compound T-4

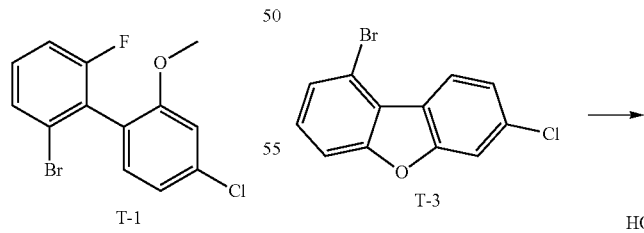

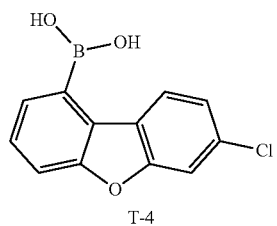

Compound T-4 (25.0 g, yield: 95%) was prepared in the same manner as in the preparation of Compound P-4 in Preparation Example A, except that Compound T-3 (30.0 g, 106.6 mmol) was used instead of Compound P-3 (30.0 g, 106.6 mmol).

MS: [M+H]$^+$=247

5) Preparation of Compound T-5

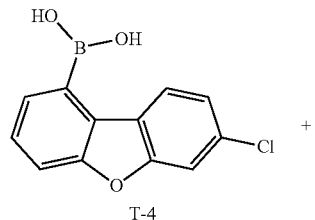

T-4

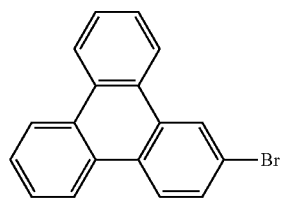

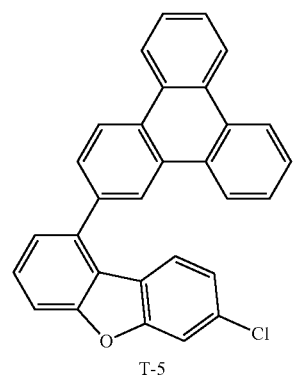

T-5

After Compound T-4 (20.0 g, 81.3 mmol) and 2-bromotriphenylene (24.9 g, 81.3 mmol) were dispersed in tetrahydrofuran (200 ml), 2M aqueous potassium carbonate solution (aq. K$_2$CO$_3$) (122 ml, 243.9 mmol) was added and tetrakis(triphenyl-phosphino)palladium [Pd(PPh$_3$)$_4$] (2.8 g, 3 mol %) was added, and then the mixture was stirred and refluxed for 5 hours. The reaction temperature was lowered to room temperature and the resulting solid was filtered. The filtered solid was recrystallized with chloroform and ethyl acetate, filtered, and then dried to prepare Compound T-5 (27.8 g, yield: 80%).

MS: [M+H]$^+$=429

6) Preparation of Compound T-6

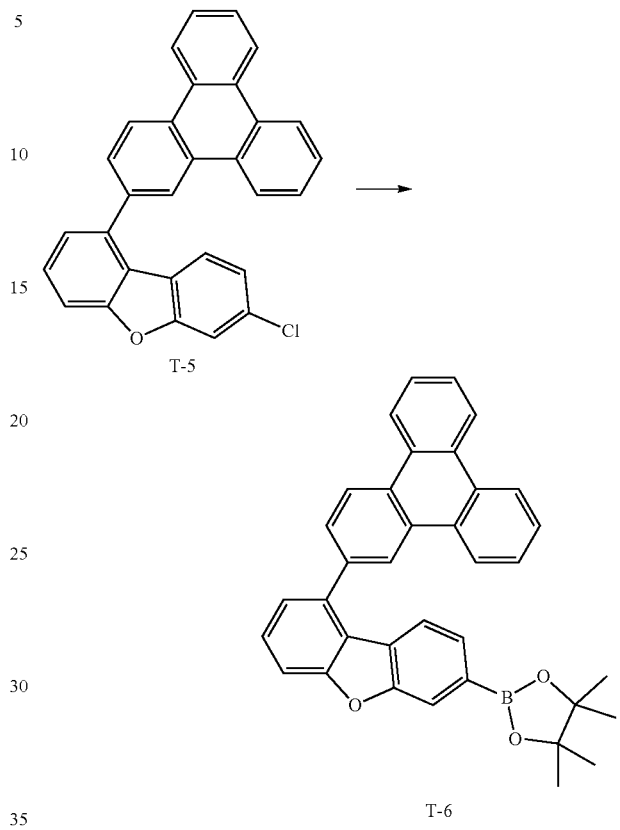

Compound T-5 (20.0 g, 46.7 mmol), bis(pinacolato)diboron (13.0 g, 51.4 mmol), and potassium acetate (9.2 g, 93.4 mmol) were mixed under a nitrogen atmosphere, and the mixture was added to 200 ml of dioxane and heated while stirring. Bis(dibenzylideneacetone)palladium (0.8 g, 1.4 mmol) and tricyclohexylphosphine (0.8 g, 2.8 mmol) were added thereto under refluxing conditions, and the mixture was heated and stirred for 3 hours. After completion of the reaction, the reaction mixture was cooled to room temperature and then filtered. Water was poured into the filtrate and extracted with chloroform, and the organic layer was dried over anhydrous magnesium sulfate. After distillation under reduced pressure, recrystallization with ethanol yielded Compound T-6 (16.8 g, 69%).

MS: [M+H]$^+$=521

Preparation Example C: Preparation of Intermediate Compound Q-6

1) Preparation of Compound Q-1

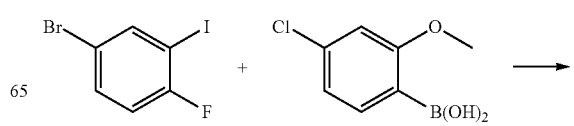

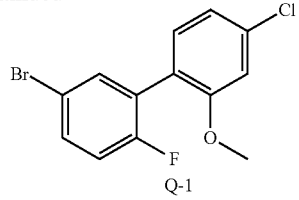

Q-1

1-bromo-4-fluoro-3-iodobenzene (50 g, 166.6 mmol) and (4-chloro-2-methoxyphenyl)boronic acid (31.1 g, 166.6 mmol) were dissolved in 800 ml of tetrahydrofuran (THF). A 2 M sodium carbonate ($Na_2CO_3$) solution (250 mL) and tetrakis(triphenyl-phosphino)palladium(0) [$Pd(PPh_3)_4$] (3.8 g, 3 mol %) were added thereto and refluxed for 12 hours. After completion of the reaction, the reaction mixture was cooled to room temperature and extracted three times with water and toluene. The toluene layer was separated, dried over magnesium sulfate, and filtered. The filtrate was distilled under reduced pressure, and the resulting mixture was recrystallized three times using chloroform and ethanol to give Compound Q-1 (27.5 g, yield: 51%).

MS: $[M+H]^+=314$

2) Preparation of Compound Q-2

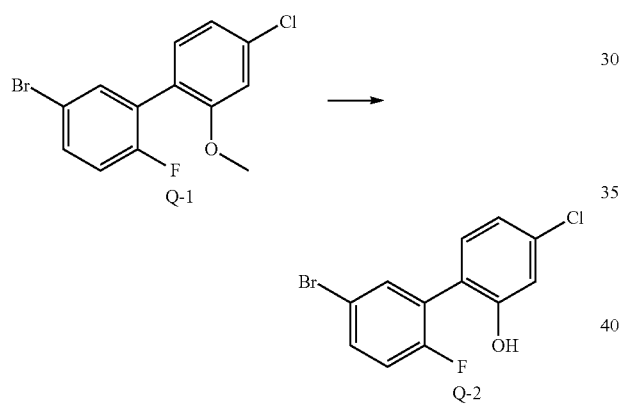

Compound Q-1 (25.0 g, 150 mmol) was dissolved in dichloromethane (300 ml) and then cooled to 0° C. Boron tribromide (7.9 ml, 83.2 mmol) was slowly added dropwise thereto and then stirred for 12 hours. After completion of the reaction, the reaction mixture was washed three times with water, dried over magnesium sulfate, and filtered. The filtrate was distilled under reduced pressure and purified by column chromatography to give Compound Q-2 (23.7 g, yield: 99%).

MS: $[M+H]^+=300$

3) Preparation of Compound Q-3

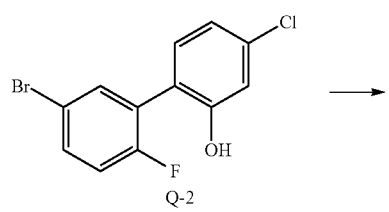

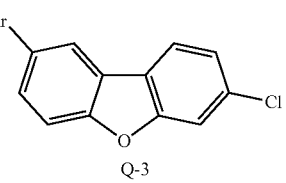

Q-3

Compound Q-2 (20.0 g, 66.4 mmol) was dissolved in distilled dimethylformamide (DMF) (200 ml). The resulting solution was cooled to 0° C. and sodium hydride (1.8 g, 72.9 mmol) was slowly added dropwise thereto. After stirring for 20 minutes, the resulting mixture was stirred at 100° C. for 1 hour. After completion of the reaction, the reaction mixture was cooled to room temperature and 100 ml of ethanol was slowly added thereto. The mixture was distilled under reduced pressure and recrystallized with chloroform and ethyl acetate to give Compound Q-3 (15.2 g, yield: 81%).

MS: $[M+H]^+=280$

4) Preparation of Compound Q-4

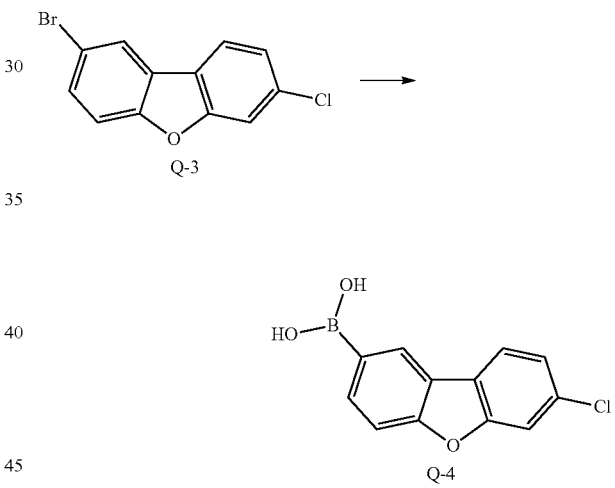

After Compound Q-3 (15.0 g, 53.3 mmol) was dissolved in tetrahydrofuran (150 ml), the temperature was lowered to −78° C., and 1.7 M tert-butyllithium (t-BuLi) (31.8 ml, 53.3 mmol) was slowly added thereto.

After stirring at the same temperature for one hour, triisopropyl borate ($B(OiPr)_3$) (14.2 ml, 107.0 mmol) was added thereto. The mixture was stirred for 3 hours while gradually raising the temperature to room temperature. A 2N aqueous hydrochloric acid solution (100 ml) was added to the reaction mixture and then stirred at room temperature for 1.5 hours. The resulting precipitate was filtered, washed sequentially with water and ethyl ether, and then dried in vacuum. After drying, the result was dispersed in ethyl ether, stirred for 2 hours, filtered, and dried to give Compound Q-4 (12.2 g, yield: 93%).

MS: $[M+H]^+=247$

5) Preparation of Compound Q-5

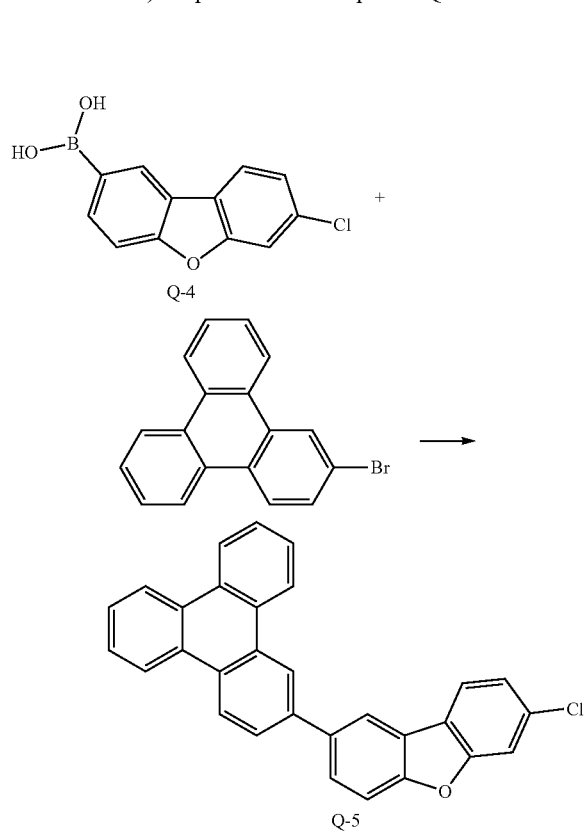

After Compound Q-4 (20.0 g, 81.3 mmol) and 2-bromotriphenylene (24.9 g, 81.3 mmol) were dispersed in tetrahydrofuran (200 ml), a 2 M aqueous potassium carbonate solution (aq. K$_2$CO$_3$) (122 ml, 243.9 mmol) was added and tetrakis(triphenyl-phosphino)palladium [Pd(PPh$_3$)$_4$] (2.8 g, 3 mol %) was added, and then the mixture was stirred and refluxed for 5 hours. The reaction temperature was lowered to room temperature, and the resulting solid was filtered. The filtered solid was recrystallized with chloroform and ethyl acetate, filtered, and dried to give Compound Q-5 (25.4 g, yield: 73%).

MS: [M+H]$^+$=429

6) Preparation of Compound Q-6

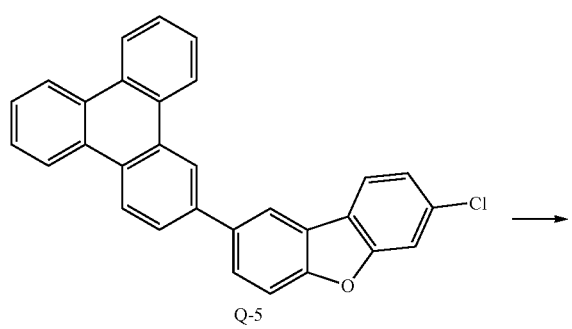

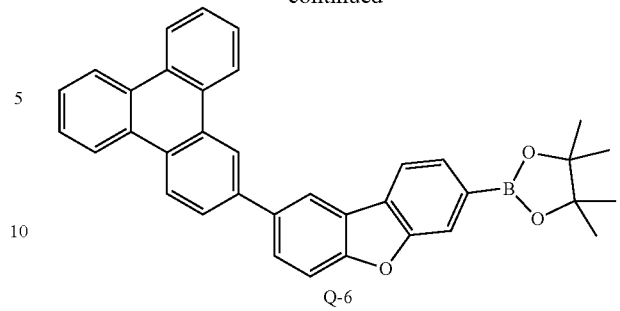

Compound Q-5 (20.0 g, 46.7 mmol), bis(pinacolato) diboron (13.0 g, 51.4 mmol), and potassium acetate (9.2 g, 93.4 mmol) were mixed under a nitrogen atmosphere, and the mixture was added to 200 ml of dioxane and heated while stirring. Bis(dibenzylideneacetone) palladium (0.8 g, 1.4 mmol) and tricyclohexylphosphine (0.8 g, 2.8 mmol) were added thereto under refluxing conditions, and the mixture was heated and stirred for 3 hours. After completion of the reaction, the reaction mixture was cooled to room temperature and filtered. Water was poured into the filtrate and extracted with chloroform, and the organic layer was dried over anhydrous magnesium sulfate. After distillation under reduced pressure, recrystallization with ethanol yielded Compound Q-6 (17.0 g, yield: 70%).

MS: [M+H]$^+$=521

Preparation Example D: Preparation of Intermediate Compound R-6

1) Preparation of Compound R-1

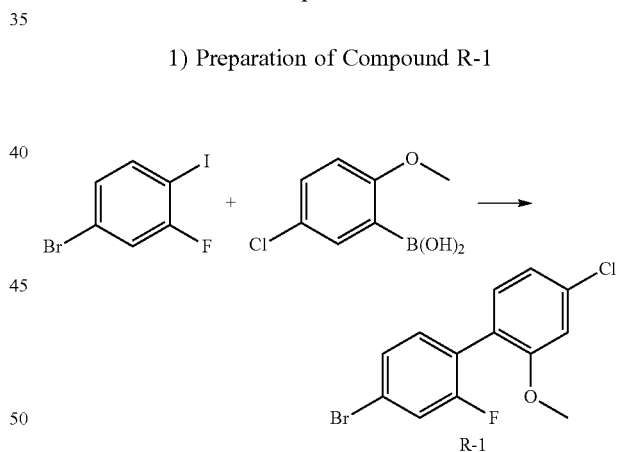

1-bromo-3-fluoro-4-iodobenzene (50 g, 166.6 mmol) and (5-chloro-2-methoxyphenyl)boronic acid (31.1 g, 166.6 mmol) were dissolved in 800 ml of tetrahydrofuran (THF). A 2 M sodium carbonate (Na$_2$CO$_3$) solution (250 mL) and tetrakis(triphenyl-phosphine)palladium(0) [Pd(PPh$_3$)$_4$] (3.8 g, 3 mol %) were added thereto and refluxed for 12 hours. After completion of the reaction, the reaction mixture was cooled to room temperature and extracted three times with water and toluene. The toluene layer was separated, dried over magnesium sulfate, and filtered. The filtrate was distilled under reduced pressure, and the resulting mixture was recrystallized three times using chloroform and ethanol to give Compound R-1 (27.5 g, yield: 51%).

MS: [M+H]$^+$=314

2) Preparation of Compound R-2

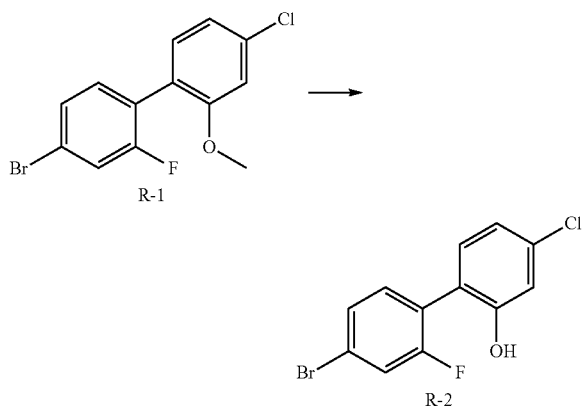

Compound R-1 (25.0 g, 150 mmol) was dissolved in dichloromethane (300 ml) and then cooled to 0° C. Boron tribromide (7.9 ml, 83.2 mmol) was slowly added dropwise thereto and then stirred for 12 hours. After completion of the reaction, the reaction mixture was washed three times with water, dried over magnesium sulfate, and filtered. The filtrate was distilled under reduced pressure and purified by column chromatography to give Compound R-2 (23.7 g, yield: 99%).

MS: [M+H]$^+$=300

3) Preparation of Compound R-3

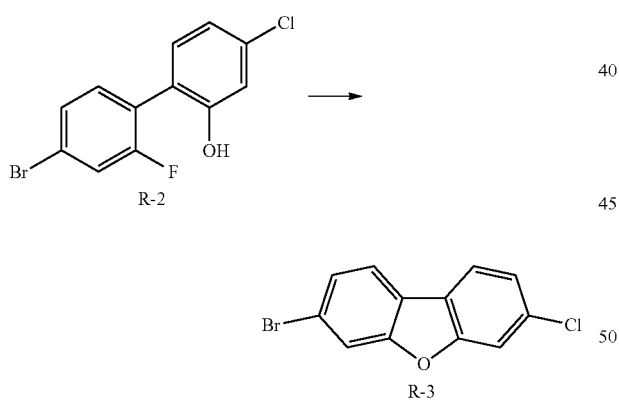

Compound R-2 (20.0 g, 66.4 mmol) was dissolved in distilled dimethylformamide (DMF) (200 ml). The resulting solution was cooled to 0° C. and sodium hydride (1.8 g, 72.9 mmol) was slowly added dropwise thereto.

After stirring for 20 minutes, the mixture was stirred at 100° C. for 1 hour. After completion of the reaction, the reaction mixture was cooled to room temperature, and 100 ml of ethanol was slowly added thereto. The resulting mixture was distilled under reduced pressure and then recrystallized with chloroform and ethyl acetate to give Compound R-3 (15.2 g, yield: 81%).

MS: [M+H]$^+$=280

4) Preparation of Compound R-4

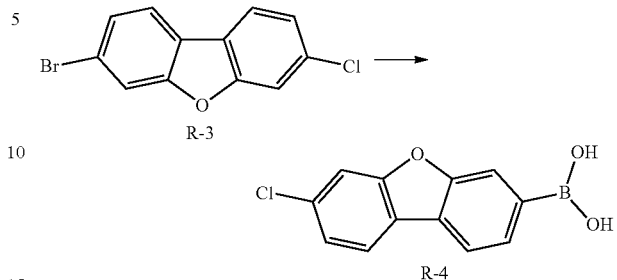

After Compound R-3 (15.0 g, 53.3 mmol) was dissolved in tetrahydrofuran (150 ml), the reaction temperature was lowered to −78° C. and 1.7 M tert-butyllithium (t-BuLi) (31.8 ml, 53.3 mmol) was slowly added thereto. After stirring at the same temperature for one hour, triisopropyl borate (B(OiPr)$_3$) (14.2 ml, 107.0 mmol) was added and stirred for 3 hours while gradually raising the temperature to room temperature. A 2N aqueous hydrochloric acid solution (100 ml) was added to the reaction mixture and then stirred for 1.5 hours at room temperature. The resulting precipitate was filtered, washed sequentially with water and ethyl ether, and dried in vacuum. After drying, the result was dispersed in ethyl ether, stirred for 2 hours, filtered, and dried to prepare Compound R-4 (12.2 g, yield: 93%).

MS: [M+H]$^+$=247

5) Preparation of Compound R-5

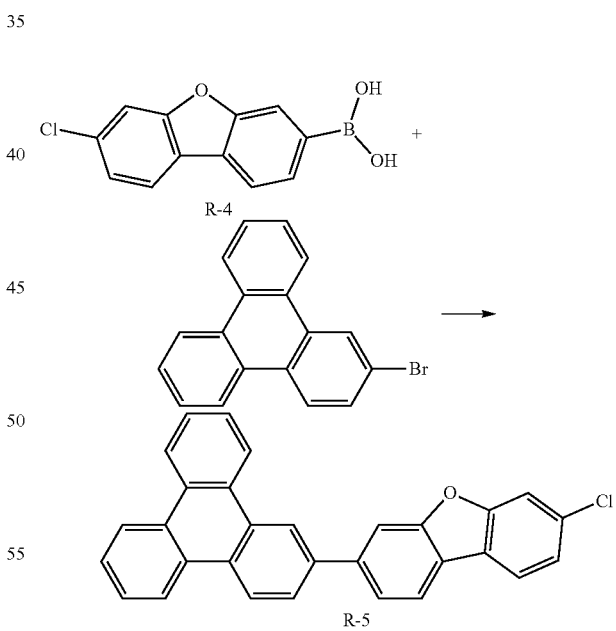

After Compound R-4 (20.0 g, 81.3 mmol) and 2-bromotriphenylene (24.9 g, 81.3 mmol) were dispersed in tetrahydrofuran (200 ml), a 2 M aqueous potassium carbonate solution (aq. K$_2$CO$_3$) (122 ml, 243.9 mmol) was added and tetrakis(triphenyl-phosphino)palladium [Pd(PPh$_3$)$_4$] (2.8 g, 3 mol %) was added, and the mixture was stirred and refluxed for 5 hours. The reaction temperature was cooled to room temperature and the resulting solid was filtered. The filtered solid was recrystallized with chloroform and ethyl acetate, and filtered and dried to give Compound R-5 (21.6 g, yield: 62%).

MS: [M+H]⁺=429

6) Preparation of Compound R-6

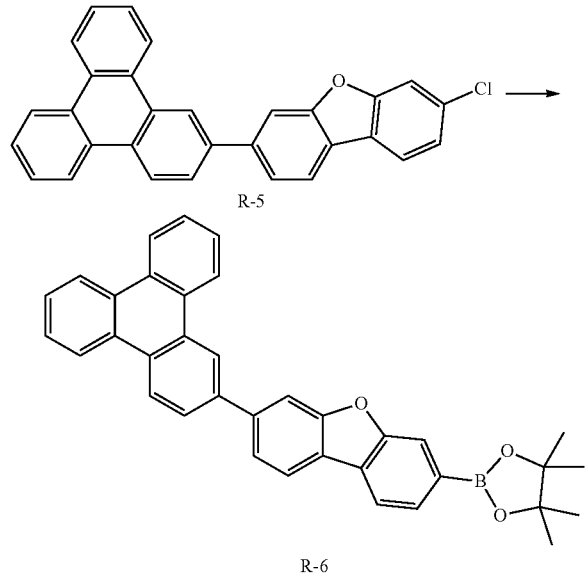

Compound R-5 (20.0 g, 46.7 mmol), bis(pinacolato)diboron (13.0 g, 51.4 mmol), and potassium acetate (9.2 g, 93.4 mmol) were mixed under a nitrogen atmosphere, and the mixture was added to 200 ml of dioxane and heated while stirring. Bis(dibenzylideneacetone)palladium (0.8 g, 1.4 mmol) and tricyclohexylphosphine (0.8 g, 2.8 mmol) were added thereto under refluxing conditions, and the mixture was heated and stirred for 3 hours. After completion of the reaction, the reaction mixture was cooled to room temperature and then filtered. Water was poured into the filtrate and extracted with chloroform, and the organic layer was dried over anhydrous magnesium sulfate. After distillation under reduced pressure, recrystallization with ethanol yielded Compound R-6 (19.9 g, yield: 82%).

MS: [M+H]⁺=521

Preparation Example 1: Preparation of Compound 1

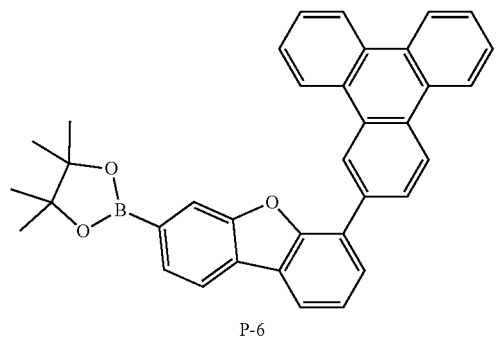

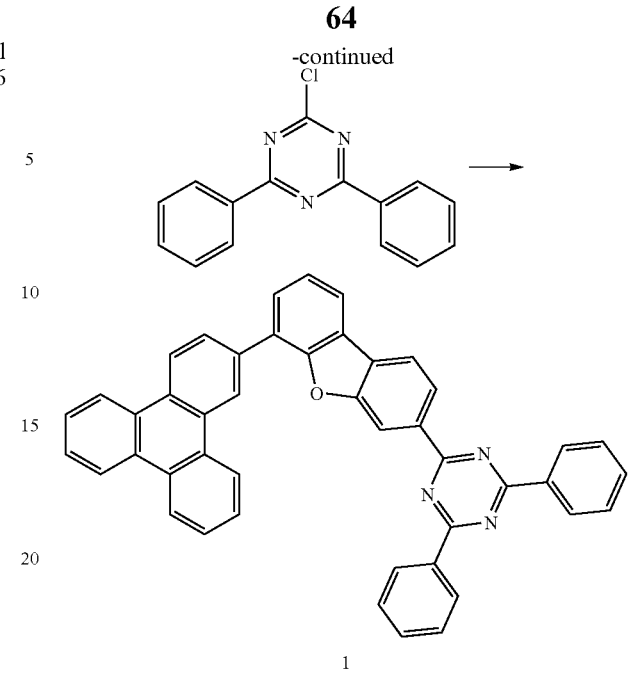

Compound P-6 (15.0 g, 28.8 mmol) and 2-chloro-4,6-diphenyl-1,3,5-triazine (7.7 g, 28.8 mmol) were added to 200 ml of tetrahydrofuran under a nitrogen atmosphere, and the mixture was stirred and refluxed. Then, potassium carbonate (12.0 g, 86.5 mmol) was dissolved in 30 ml of water, the solution was added and stirred thoroughly, and tetrakis(triphenyl-phosphino) palladium (1.0 g, 3 mol %) was added. After reaction for 4 hours, the reaction mixture was cooled to room temperature and filtered. The filtrate was dissolved in chloroform and extracted with water, and then the organic layer was dried over magnesium sulfate. The organic layer was dried and then recrystallized with ethyl acetate to give Compound 1 (7.0 g, yield: 39%).

MS: [M+H]⁺=626

Preparation Example 2: Preparation of Compound 2

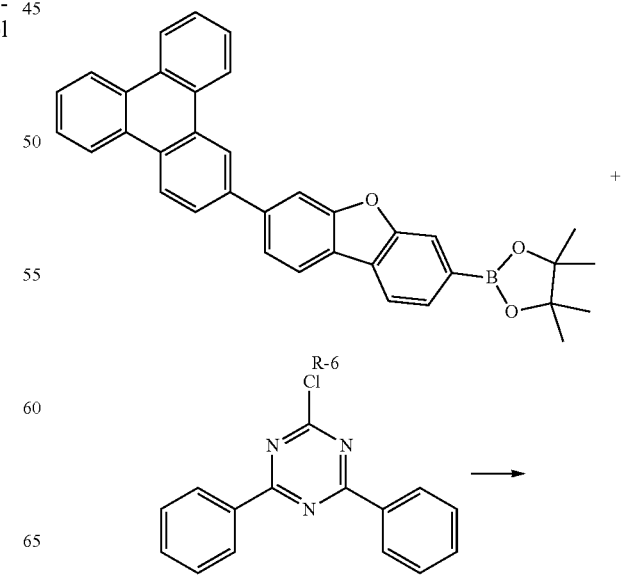

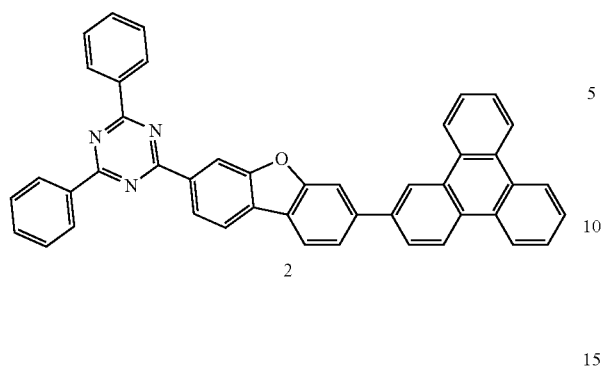

2

Compound R-6 (15.0 g, 28.8 mmol) and 2-chloro-4,6-diphenyl-1,3,5-triazine (7.7 g, 28.8 mmol) were added to 200 ml of tetrahydrofuran under a nitrogen atmosphere, and the mixture was stirred and refluxed. Then, potassium carbonate (12.0 g, 86.5 mmol) was dissolved in 30 ml of water, the solution was added and stirred thoroughly, and tetrakis (triphenyl-phosphino)palladium (1.0 g, 3 mol %) was added. After reaction for 4 hours, the reaction mixture was cooled to room temperature and filtered. The filtrate was dissolved in chloroform and extracted with water, and then the organic layer was dried over magnesium sulfate. The organic layer was dried and then recrystallized with ethyl acetate to give Compound 2 (10.5 g, yield: 58%).

MS: [M+H]$^+$=626

Preparation Example 3: Preparation of Compound 3

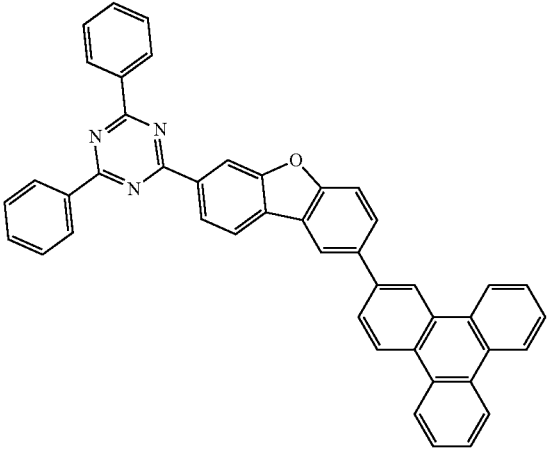

3

Compound Q-6 (15.0 g, 28.8 mmol) and 2-chloro-4,6-diphenyl-1,3,5-triazine (7.7 g, 28.8 mmol) were added to 200 ml of tetrahydrofuran under a nitrogen atmosphere, and the mixture was stirred and refluxed. Then, potassium carbonate (12.0 g, 86.5 mmol) was dissolved in 30 ml of water, the solution was added and stirred thoroughly, and tetrakis (triphenyl-phosphino)palladium (1.0 g, 3 mol %) was added. After reaction for 4 hours, the reaction mixture was cooled to room temperature and then filtered. The filtrate was dissolved in chloroform and extracted with water, and then the organic layer was dried over magnesium sulfate. Then, the organic layer was dried and recrystallized with ethyl acetate to give Compound 3 (9.4 g, yield: 52%).

MS: [M+H]$^+$=626

Preparation Example 4: Preparation of Compound 4

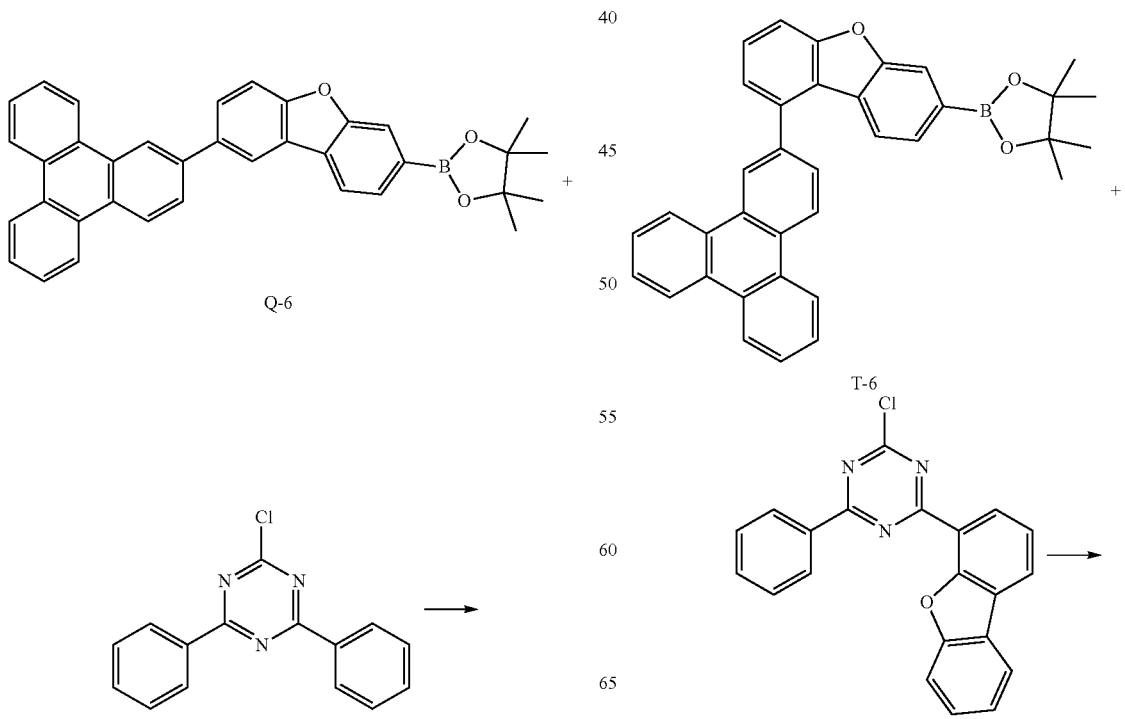

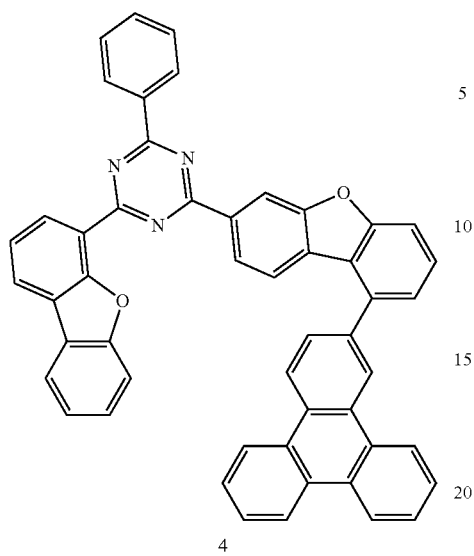

4

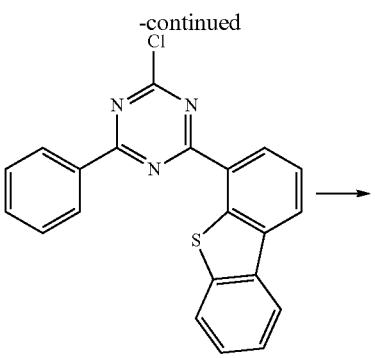

Compound T-6 (15.0 g, 28.8 mmol) and 2-chloro-4-(dibenzo[b,d]furan-4-yl)-6-phenyl-1,3,5-triazine (10.3 g, 28.8 mmol) were added to 200 ml of tetrahydrofuran under a nitrogen atmosphere, and the mixture was stirred and refluxed. Then, potassium carbonate (12.0 g, 86.5 mmol) was dissolved in 30 ml of water, the solution was added and stirred thoroughly, and tetrakis(triphenyl-phosphino)palladium (1.0 g, 3 mol %) was added. After reaction for 4 hours, the reaction mixture was cooled to room temperature and then filtered. The filtrate was dissolved in chloroform and extracted with water, and then the organic layer was dried over magnesium sulfate. Then, the organic layer was dried and recrystallized with ethyl acetate to give Compound 4 (13.2 g, 64%)

MS: [M+H]$^+$=626

Preparation Example 5: Preparation of Compound 5

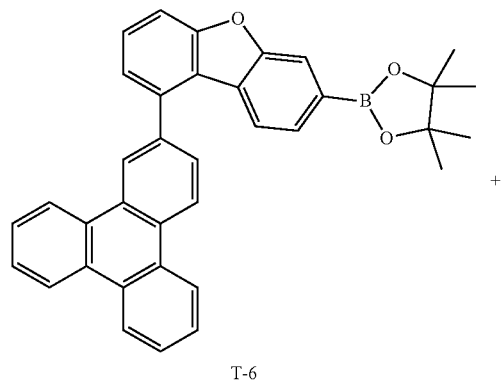

T-6

+

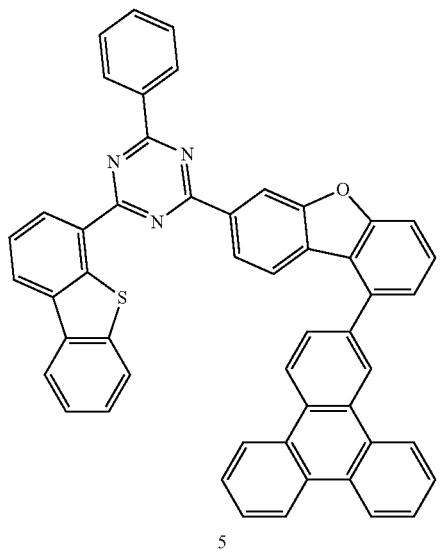

5

Compound T-6 (15.0 g, 28.8 mmol) and 2-chloro-4-(dibenzo[b,d]thiophen-4-yl)-6-phenyl-1,3,5-triazine (10.8 g, 28.8 mmol) were added to 200 ml of tetrahydrofuran under a nitrogen atmosphere, and the mixture was stirred and refluxed. Then, potassium carbonate (12.0 g, 86.5 mmol) was dissolved in 30 ml of water, the solution was added and stirred thoroughly, and tetrakis(triphenyl-phosphino)palladium (1.0 g, 3 mol %) was added. After reaction for 4 hours, the reaction mixture was cooled to room temperature and then filtered. The filtrate was dissolved in chloroform and extracted with water, and then the organic layer was dried over magnesium sulfate. Then, the organic layer was dried and recrystallized with ethyl acetate to give Compound 5 (10.5 g, 50%).

MS: [M+H]$^+$=626

Preparation Example 6: Preparation of Compound 6

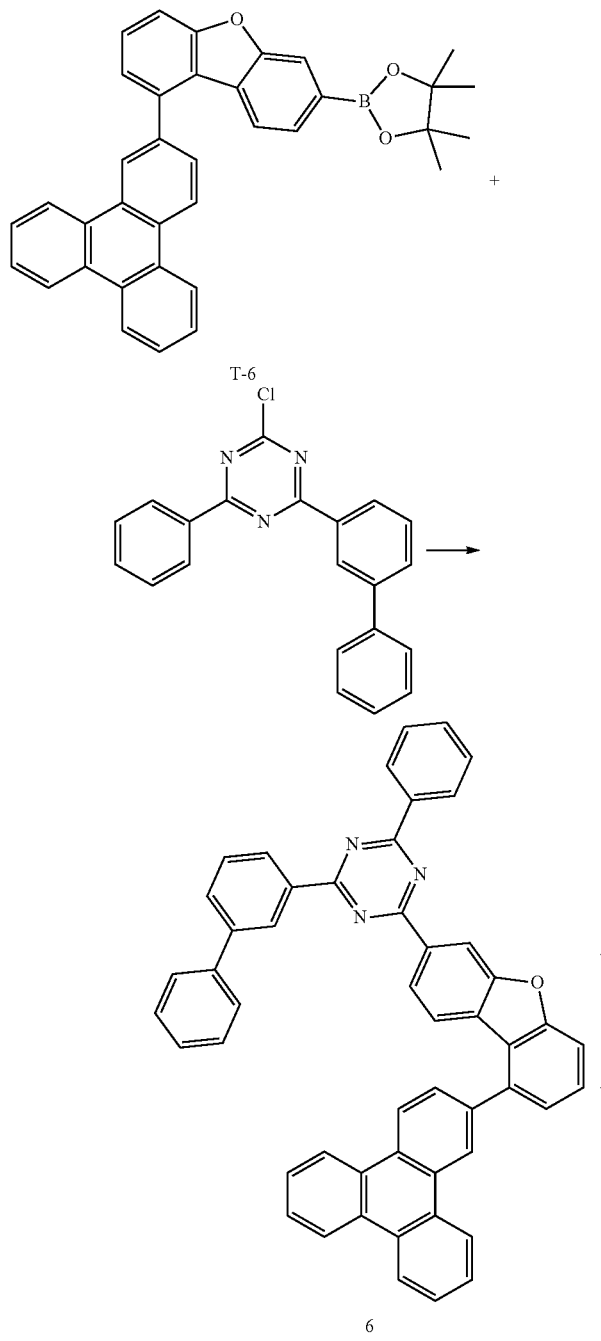

Compound T-6 (15.0 g, 28.8 mmol) and 2-([1,1'-biphenyl]-3-yl)-4-chloro-6-phenyl-1,3,5-triazine (9.9 g, 28.8 mmol) were added to 200 ml of tetrahydrofuran under a nitrogen atmosphere, and the mixture was stirred and refluxed. Then, potassium carbonate (12.0 g, 86.5 mmol) was dissolved in 30 ml of water, the solution was added and thoroughly, stirred and tetrakis(triphenyl-phosphino) palladium (1.0 g, 3 mol %) was added. After reaction for 4 hours, the reaction mixture was cooled to room temperature and then filtered. The filtrate was dissolved in chloroform and extracted with water, and then the organic layer was dried over magnesium sulfate. Then, the organic layer was dried and recrystallized with ethyl acetate to give Compound 6 (9.1 g, 45%).

MS: [M+H]$^+$=702

Preparation Example 7: Preparation of Compound 7

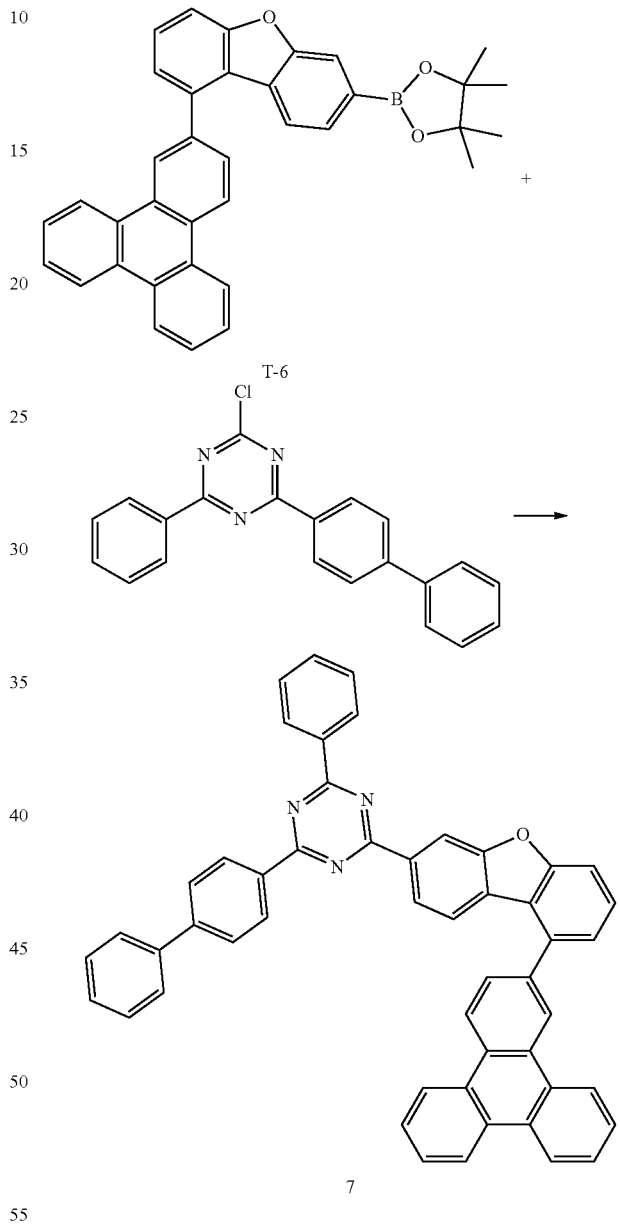

Compound T-6 (15.0 g, 28.8 mmol) and 2-([1,1'-biphenyl]-4-yl)-4-chloro-6-phenyl-1,3,5-triazine (9.9 g, 28.8 mmol) were added to 200 ml of tetrahydrofuran under a nitrogen atmosphere, and the mixture was stirred and refluxed. Then, potassium carbonate (12.0 g, 86.5 mmol) was dissolved in 30 ml of water, the solution was added and stirred thoroughly, and tetrakis(triphenyl-phosphino)palladium (1.0 g, 3 mol %) was added. After reaction for 4 hours, the reaction mixture was cooled to room temperature and then filtered. The filtrate was dissolved in chloroform and extracted with water, and then the organic layer was dried over magnesium sulfate. Then, the organic layer was dried and recrystallized with ethyl acetate to give Compound 7 (14.4 g, 71%).

MS: [M+H]⁺=702

Preparation Example 8: Preparation of Compound 8

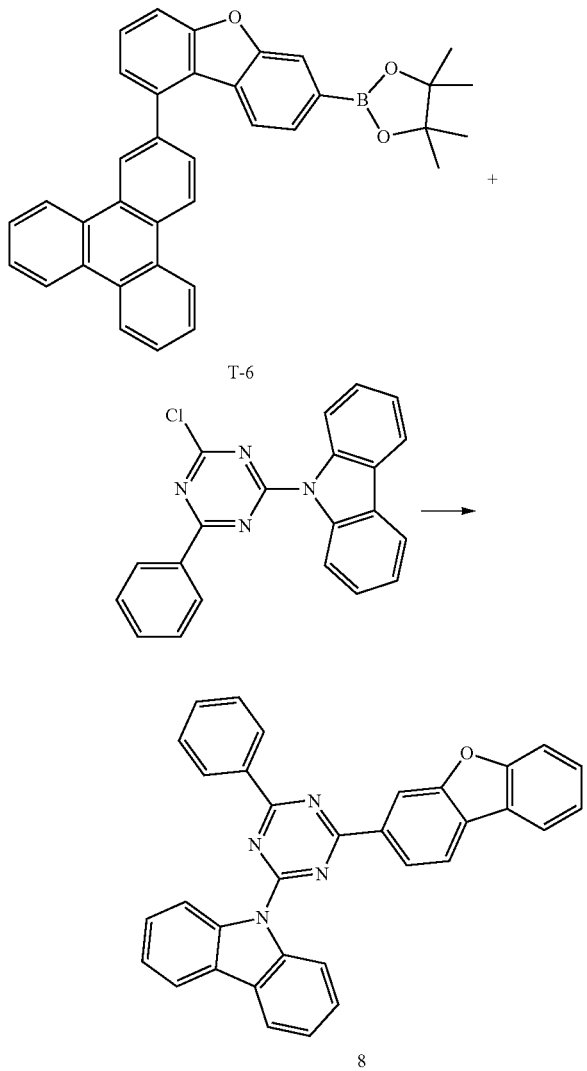

8

Compound T-6 (15.0 g, 28.8 mmol) and 9-(4-chloro-6-phenyl-1,3,5-triazin-2-yl)-9H-carbazole (9.9 g, 28.8 mmol) were added to 200 ml of tetrahydrofuran under a nitrogen atmosphere, and the mixture was stirred and refluxed. Then, potassium carbonate (12.0 g, 86.5 mmol) was dissolved in 30 ml of water, the solution was added and thoroughly, stirred and tetrakis(triphenyl-phosphino)palladium (1.0 g, 3 mol %) was added. After reaction for 4 hours, the reaction mixture was cooled to room temperature and then filtered. The filtrate was dissolved in chloroform and extracted with water, and then the organic layer was dried over magnesium sulfate. Then, the organic layer was dried and recrystallized with ethyl acetate to give Compound 8 (12.2 g, 59%).

MS: [M+H]⁺=715

Preparation Example 9: Preparation of Compound 9

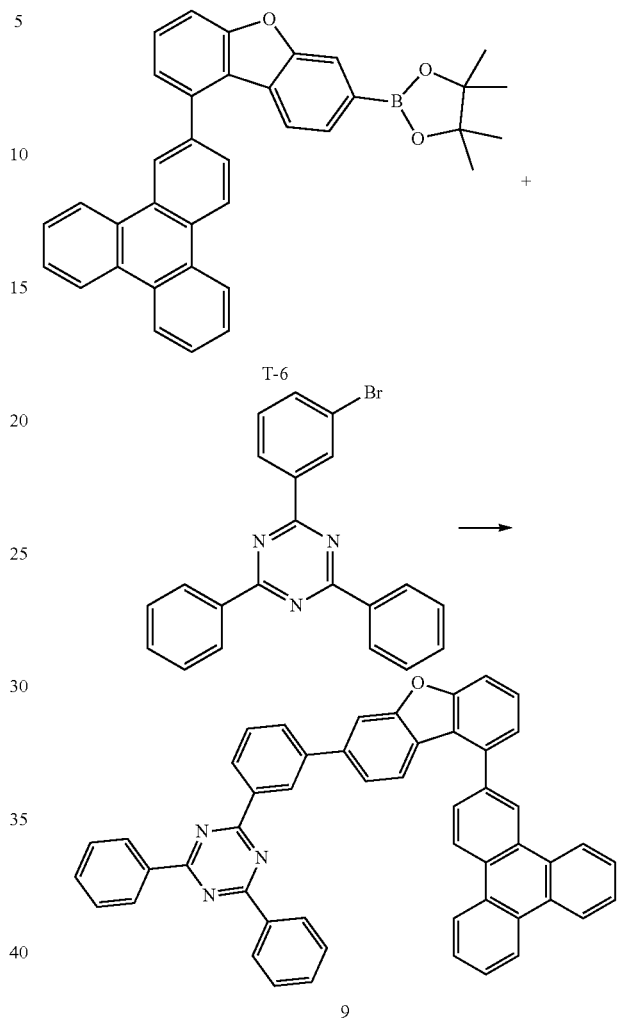

9

Compound T-6 (15.0 g, 28.8 mmol) and 2-(3-bromophenyl)-4,6-diphenyl-1,3,5-triazine (11.2 g, 28.8 mmol) were added to 200 ml of tetrahydrofuran under a nitrogen atmosphere, and the mixture was stirred and refluxed. Then, potassium carbonate (12.0 g, 86.5 mmol) was dissolved in 30 ml of water, the solution was added and stirred thoroughly, and tetrakis(triphenyl-phosphino)palladium (1.0 g, 3 mol %) was added. After reaction for 4 hours, the reaction mixture was cooled to room temperature and then filtered. The filtrate was dissolved in chloroform and extracted with water, and then the organic layer was dried over magnesium sulfate. Then, the organic layer was dried and recrystallized with ethyl acetate to give Compound 9 (8.9 g, 44%).

MS: [M+H]⁺=702

Example 1: Manufacture of Organic Light Emitting Device

A glass substrate thinly coated with ITO (indium tin oxide) to a thickness of 1300 Å was put into distilled water in which a detergent was dissolved, and ultrasonically cleaned. In this case, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. In addition, the substrate was cleaned for 5 minutes using oxygen plasma, and then transferred to a vacuum depositor.

On the ITO transparent electrode thus prepared, the following compound HI-1 was thermally vacuum deposited to a thickness of 50 Å to form a hole injection layer. The following compound HT-1 was thermally vacuum deposited on the hole injection layer to a thickness of 250 Å to form a hole transport layer, and the following compound HT-2 was vacuum deposited on the hole transport layer to a thickness of 50 Å to form an electron blocking layer.

The compound 1 prepared in the previous Preparation Example 1, the following compound YGH-1 and phosphorescent dopant YGD-1 were co-deposited at a weight ratio of 44:44:12 on the electron blocking layer to form a light emitting layer with a thickness of 400 Å.

The following compound ET-1 was vacuum deposited on the light emitting layer to a thickness of 250 Å to form an electron transport layer, and the following compound ET-2 and Li were vacuum deposited at a weight ratio of 98:2 on the electron transport layer to form an electron injection layer with a thickness of 100 Å. Aluminum was deposited on the electron injection layer to a thickness of 1000 Å to form a cathode.

HI-1

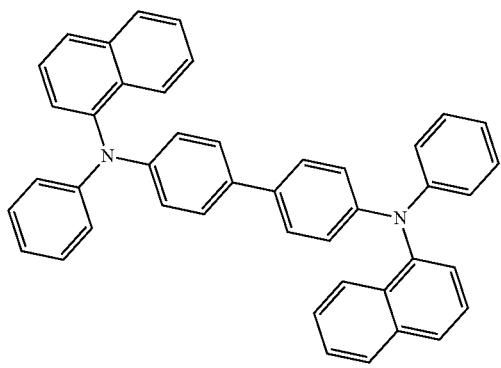

HT-1

HT-2

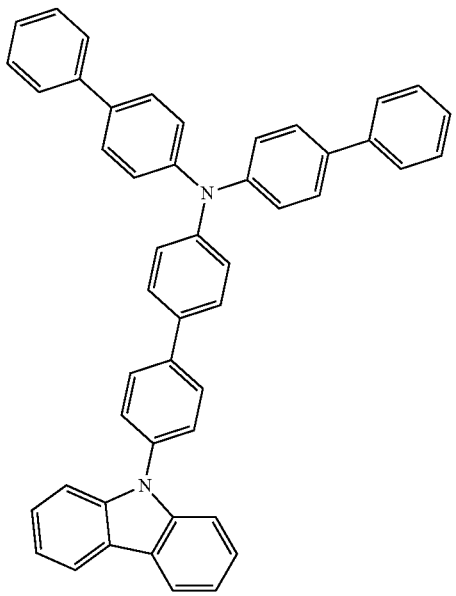

YGH-1

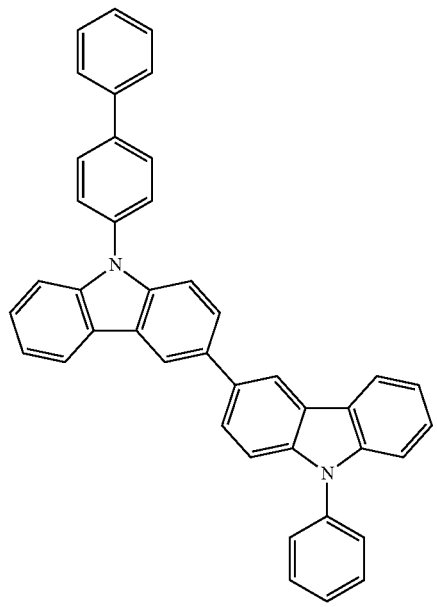

YGD-1

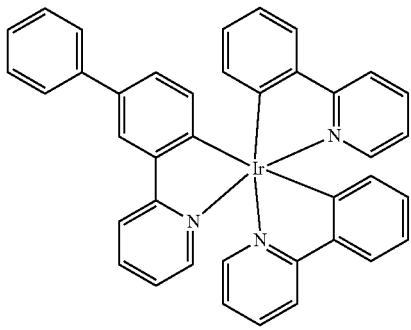

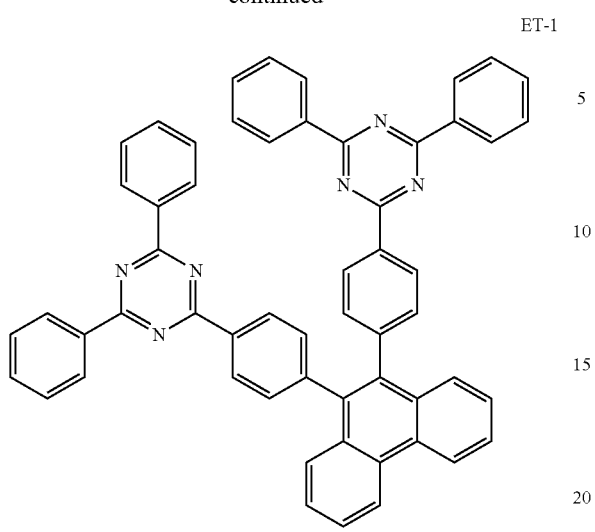

ET-1

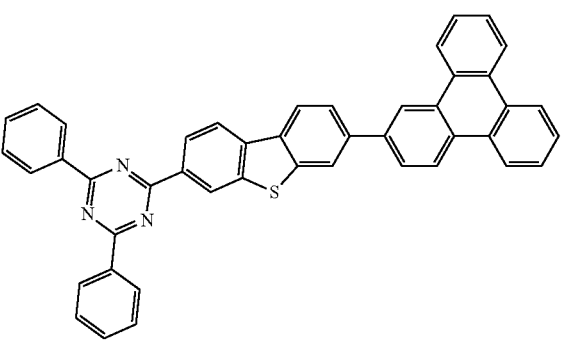

ET-2

In the above-mentioned process, the vapor deposition rate of the organic material was maintained at 0.4 to 0.7 Å/s, the deposition rate of aluminum was maintained at 2 Å/s, and the degree of vacuum during the deposition was maintained at $1\times10^{-7}$ to $5\times10^{-8}$ Torr.

Examples 2 to 9

The organic light emitting devices were manufactured in the same manner as in Example 1, except that the compounds shown in Table 1 below were used instead of compound 1 of Preparation Example 1.

Comparative Examples 1 to 5

The organic light emitting devices were manufactured in the same manner as in Example 1, except that the compounds shown in Table 1 below were used instead of compound 1 of Preparation Example 1. The structures of the compounds of CE1, CE2, CE3, CE4, and CE5 used in Table 1 are as follows.

CE1

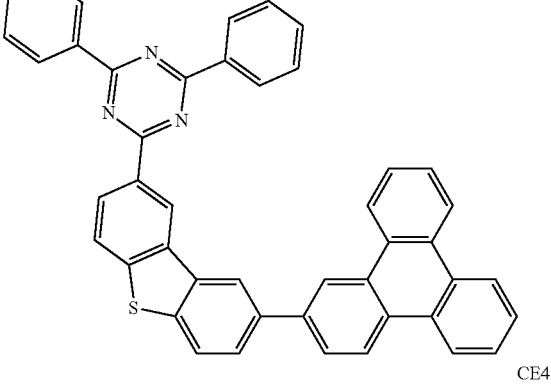

CE2

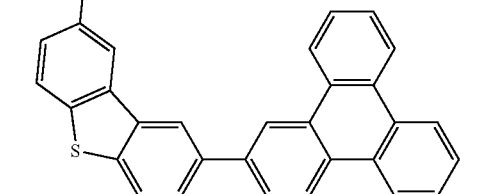

CE3

CE4

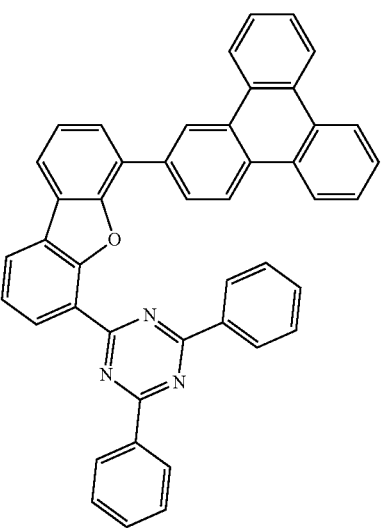

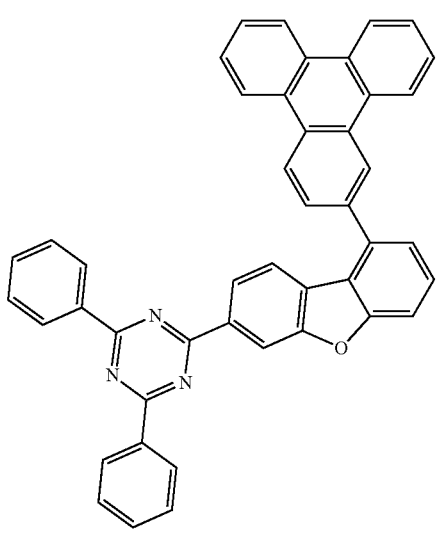

CE5

Experimental Example 1

The voltage and efficiency at the current density of 10 mA/cm², color coordinates, and lifetime ($LT_{95}$) at the current density of 50 mA/cm² were measured by applying a current to the organic light emitting devices manufactured in the examples and comparative examples, and the results are shown in Table 1 below. At this time, the lifetime ($LT_{95}$) means the time required for the luminance to be reduced to 95% of the initial luminance.

TABLE 1

| | Compound (Light emitting layer host) | Voltage (V) (@10 mA/cm²) | Efficiency (Cd/A) (@10 mA/cm²) | Color coordinates (x, y) | Lifetime (h) ($LT_{95}$ @50 mA/cm²) |
|---|---|---|---|---|---|
| Example 1 | Compound 1 | 3.8 | 82 | 0.44, 0.53 | 180 |
| Example 2 | Compound 2 | 3.7 | 83 | 0.46, 0.54 | 178 |
| Example 3 | Compound 3 | 3.9 | 81 | 0.46, 0.53 | 181 |
| Example 4 | Compound 4 | 3.8 | 82 | 0.46, 0.55 | 225 |
| Example 5 | Compound 5 | 3.8 | 81 | 0.46, 0.53 | 240 |
| Example 6 | Compound 6 | 3.7 | 83 | 0.46, 0.54 | 230 |
| Example 7 | Compound 7 | 3.7 | 83 | 0.46, 0.54 | 210 |
| Example 8 | Compound 8 | 4.0 | 79 | 0.46, 0.53 | 235 |
| Example 9 | Compound 9 | 3.6 | 85 | 0.46, 0.54 | 170 |
| Comparative Example 1 | CE1 | 4.5 | 71 | 0.46, 0.54 | 90 |
| Comparative Example 2 | CE2 | 4.0 | 79 | 0.46, 0.55 | 130 |
| Comparative Example 3 | CE3 | 4.2 | 79 | 0.46, 0.55 | 15 |
| Comparative Example 4 | CE4 | 4.3 | 78 | 0.46, 0.55 | 110 |
| Comparative Example 5 | CE5 | 3.9 | 79 | 0.46, 0.54 | 145 |

As shown in Table 1, the organic light emitting device using the compound of the present invention as a host material in the light emitting layer exhibited significantly improved lifetime characteristics while exhibiting higher efficiency, as compared with an organic light emitting device using a material of the comparative examples as a host material in the light emitting layer.

Specifically, it can be seen that the substitution positions of the two substituents bonded to dibenzofuran/dibenzothiophene affect the characteristics of the organic light emitting device. This is considered to be because the compound represented by Chemical Formula 1 has increased electronic stability as compared with Compound CE2 substituted with a triphenylenyl group at a position symmetric with respect to a triazinyl group, Compounds CE3 and CE4 having a triphenylenyl group at a position different from the present invention, and Compound CE5 in which the triphenylenyl group is bonded at position *3 and all of the substituents of the triazinyl group are phenyl.

Therefore, in general, considering that the luminous efficiency and lifetime characteristics of the organic light emitting devices have a trade-off relationship with each other, it can be seen that the organic light emitting devices employing the compound represented by Chemical Formula 1 exhibit significantly improved device characteristics as compared with the devices of the comparative examples.

DESCRIPTION OF SYMBOLS

1: substrate
2: anode
3: light emitting layer
4: cathode
5: hole injection layer
6: hole transport layer
7: electron blocking layer
8: electron transport layer
9: electron injection layer

What is claimed is:

1. A compound of Chemical Formula 1:

[Chemical Formula 1]

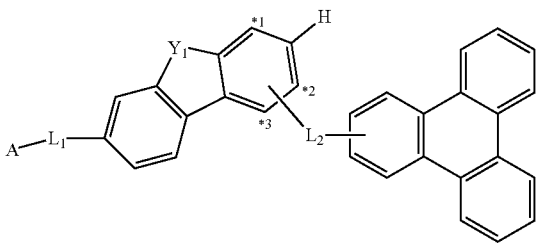

wherein in Chemical Formula 1:

$Y_1$ is O or S;

$L_1$ and $L_2$ are each independently a single bond, a substituted or unsubstituted $C_{6-60}$ arylene, or a substituted or unsubstituted $C_{2-60}$ heteroarylene containing one or more heteroatoms selected from the group consisting of O, N, and S, with the proviso that $L_2$ is bonded to any one of positions *1, *2, and *3;

A is any one of Chemical Formulas 2 to 4:

[Chemical Formula 2]

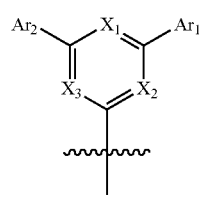

[Chemical Formula 3]

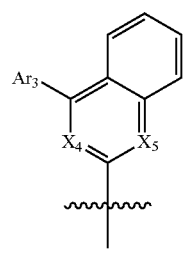

[Chemical Formula 4]

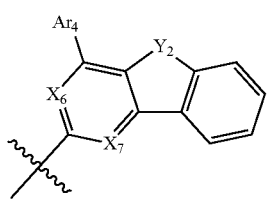

wherein in Chemical Formulas 2 to 4:

$X_1$ to $X_3$ are each independently N or CH, with the proviso that at least two of $X_1$ to $X_3$ are N;

$X_4$ and $X_5$ are each independently N or CH, with the proviso that at least one of $X_4$ and $X_5$ is N;

$X_6$ and $X_7$ are each independently N or CH, with the proviso that at least one of $X_6$ and $X_7$ is N;

$Y_2$ is O or S;

$Ar_1$ is a substituted or unsubstituted $C_{6-60}$ aryl, or a substituted or unsubstituted $C_{2-60}$ heteroaryl containing one or more heteroatoms selected from the group consisting of N, O, and S;

$Ar_2$ is a substituted or unsubstituted $C_{10-20}$ aryl, or a substituted or unsubstituted $C_{2-20}$ heteroaryl containing one heteroatom selected from the group consisting of N, O or S; and $Ar_3$ and $Ar_4$ are each independently a substituted or unsubstituted Coco aryl, or a substituted or unsubstituted $C_{2-60}$ heteroaryl containing one or more heteroatoms selected from the group consisting of N, O, and S.

2. The compound according to claim 1,
wherein $L_1$ and $L_2$ are each independently a single bond, phenylene, or biphenylylene.

3. The compound according to claim 1,
wherein in Chemical Formula 2, $X_1$ to $X_3$ are N, $X_1$ and $X_2$ are N and $X_3$ is CH, or $X_2$ and $X_3$ are N and $X_1$ is CH, wherein in Chemical Formula 3, $X_4$ and $X_5$ are N, and wherein in Chemical Formula 4, $X_6$ and $X_7$ are N.

4. The compound according to claim 1,
wherein the compound of Chemical Formula 1 is any one of the following Chemical Formulas 1A to 1C:

[Chemical Formula 1A]

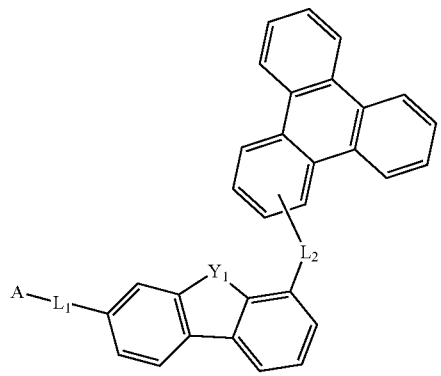

wherein in Chemical Formula 1A:
$Y_1$ is O or S;
$L_1$ and $L_2$ are each independently a single bond or a $C_{6-20}$ arylene; and
A is any one of Chemical Formulas 2 to 4 as defined in Chemical Formula 1;

[Chemical Formula 1B]

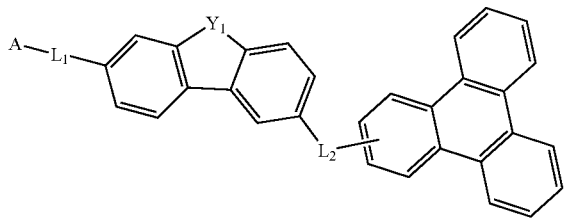

wherein in Chemical Formula 1B:
$Y_1$ is O or S;
$L_1$ and $L_2$ are each independently a single bond or a $C_{6-20}$ arylene; and
A is any one of Chemical Formulas 2 to 4 as defined in Chemical Formula 1;

[Chemical Formula 1C]

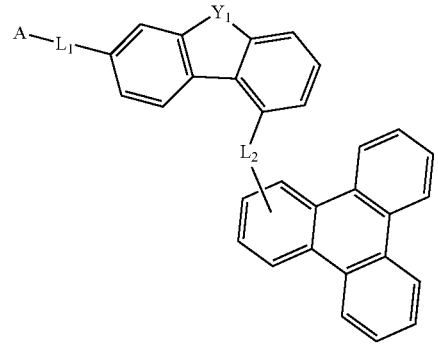

wherein in Chemical Formula 1C:
$Y_1$ is O or S;

$L_1$ and $L_2$ are each independently a single bond or a $C_{6-20}$ arylene;

A is any one of Chemical Formulas 2 to 4 as defined in Chemical Formula 1, provided that in Chemical Formula 2:

$Ar_1$ is a $C_{6-20}$ aryl or a $C_{2-20}$ heteroaryl containing one atom of O or S, and $Ar_2$ is a $C_{10-20}$ aryl or a $C_{2-20}$ heteroaryl containing one atom of O or S.

5. The compound according to claim 4, wherein in Chemical Formula 1A, 1B, and 1C:

$Ar_1$, $Ar_3$, and $Ar_4$ are each independently phenyl, biphenylyl, dibenzofuranyl, or dibenzothiophenyl, and $Ar_2$ is biphenylyl, dibenzofuranyl, or dibenzothiophenyl.

6. The compound according to claim 1, wherein the compound is any one of the following Chemical Formulas 1D to 1F:

[Chemical Formula 1D]

[Chemical Formula 1E]

[Chemical Formula 1F]

wherein in Chemical Formulas 1D to 1F, $Y_1$, $Y_2$, $L_1$, $L_2$, $X_1$ to $X_7$, and $Ar_1$ to $Ar_4$ are the same as defined in claim 1.

7. The compound according to claim 6, wherein in Chemical Formula 1D, $L_2$ is bonded to position *1 or *2.

8. The compound according to claim 1, wherein the compound is represented by any one of the following Chemical Formulas 1-1 to 1-6:

1-1

1-2

1-3

1-4

-continued 1-5

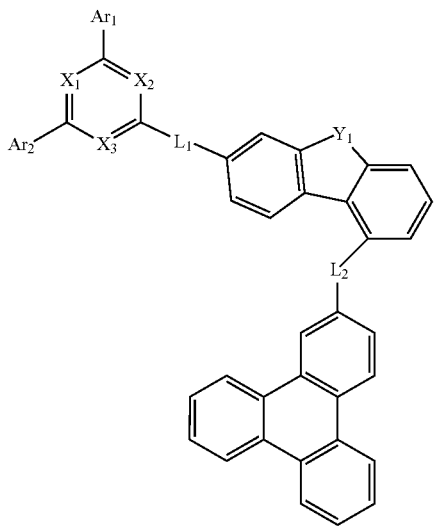

1-6

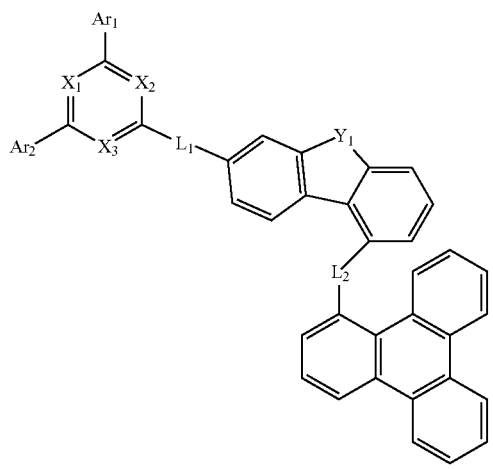

wherein in Chemical Formulas 1-1 to 1-4,
  $X_1$ to $X_3$ are N; or $X_1$ and $X_2$ are N, and $X_3$ is CH; or $X_2$ and $X_3$ are N, and $X_1$ is CH;
  $Ar_1$ is phenyl, biphenylyl, dibenzofuranyl, or dibenzothiophenyl,
  $Ar_2$ is biphenyl, dibenzofuranyl, or dibenzothiophenyl, and
  $Y_1$, $L_1$, and $L_2$ are as defined in claim 1,
wherein in Chemical Formulas 1-5 and 1-6,
  $X_1$ to $X_3$ are N; or $X_1$ and $X_2$ are N, and $X_3$ is CH; or $X_2$ and $X_3$ are N, and $X_1$ is CH;
  $Ar_1$ is phenyl, biphenylyl, dibenzofuranyl, or dibenzothiophenyl,
  $Ar_2$ is biphenylyl, dibenzofuranyl, or dibenzothiophenyl, and
  $Y_1$, $L_1$, and $L_2$ are the same as defined in claim 1.

9. The compound according to claim 1,
wherein the compound is any one compound selected from the group consisting of the following compounds:

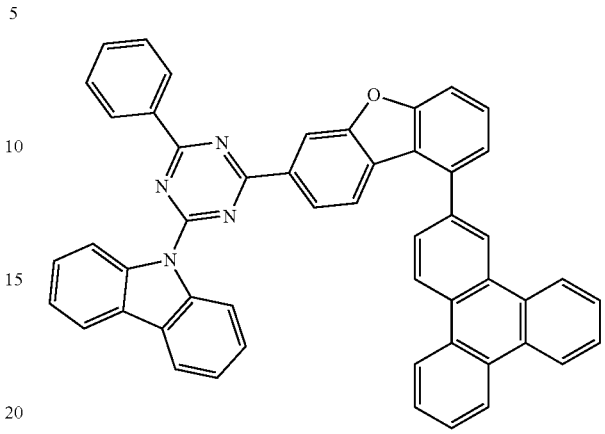

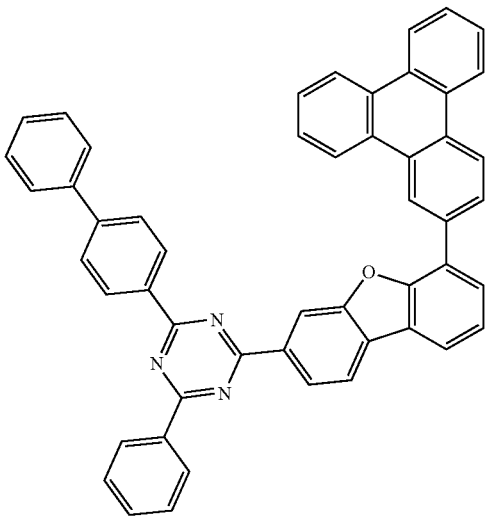

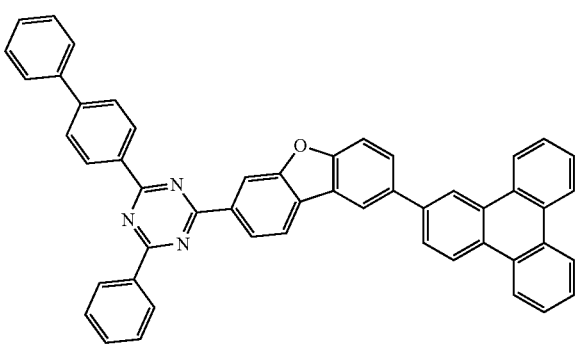

85
-continued
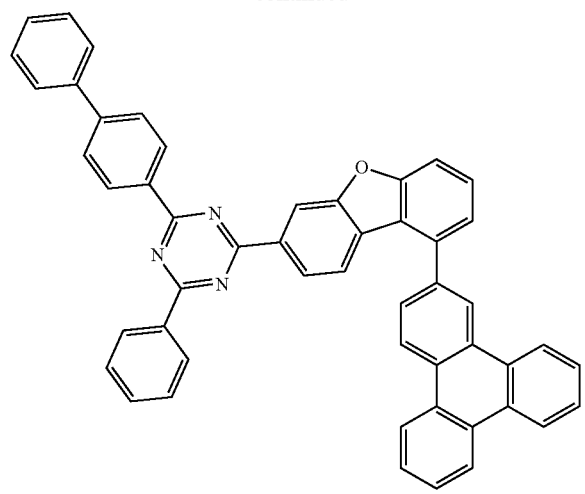
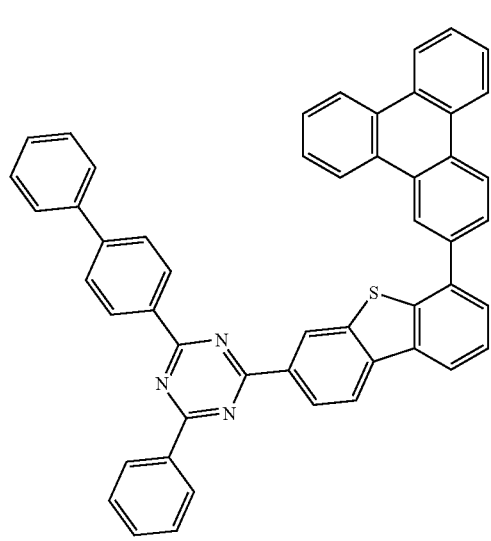
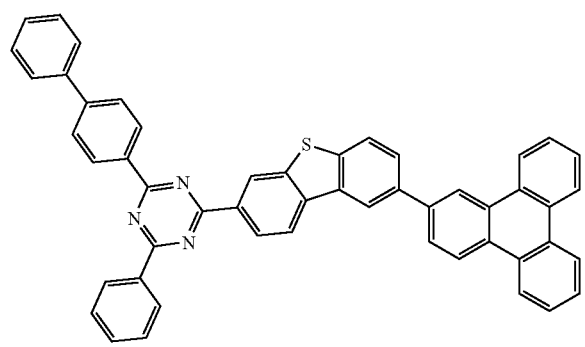
86
-continued
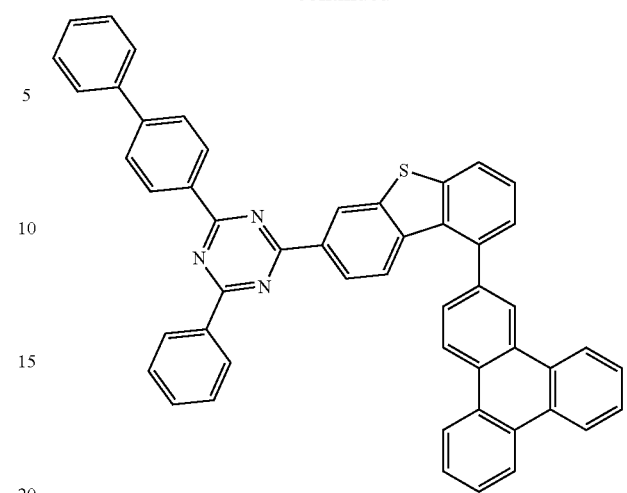
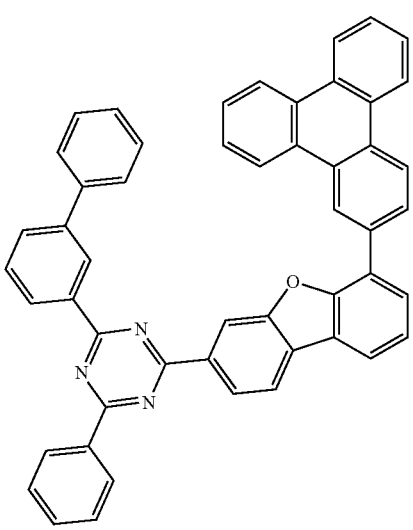
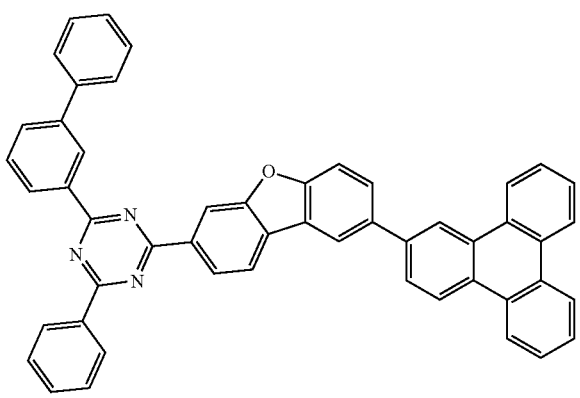

87
-continued
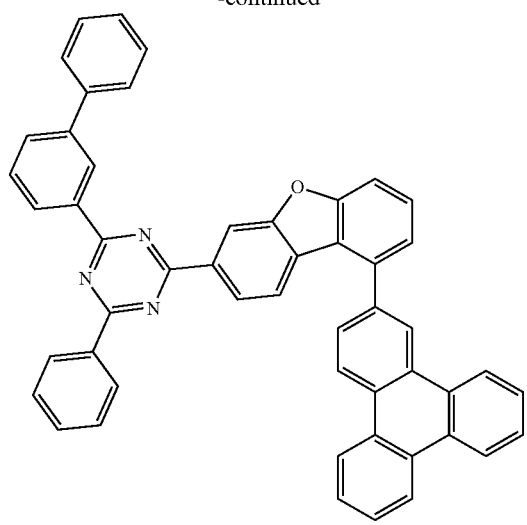
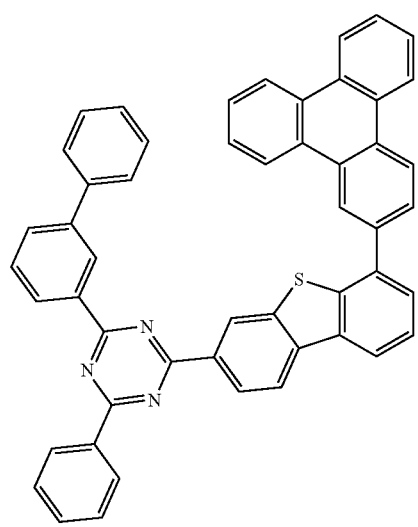
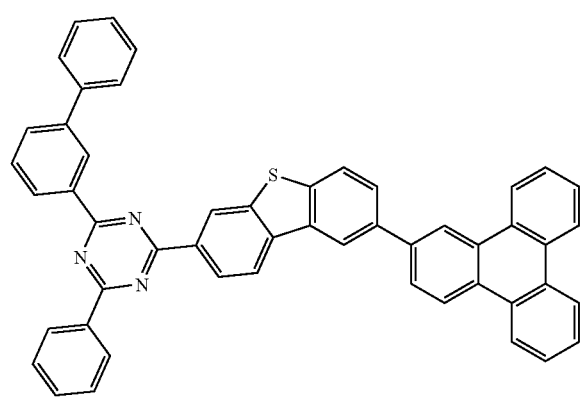
88
-continued
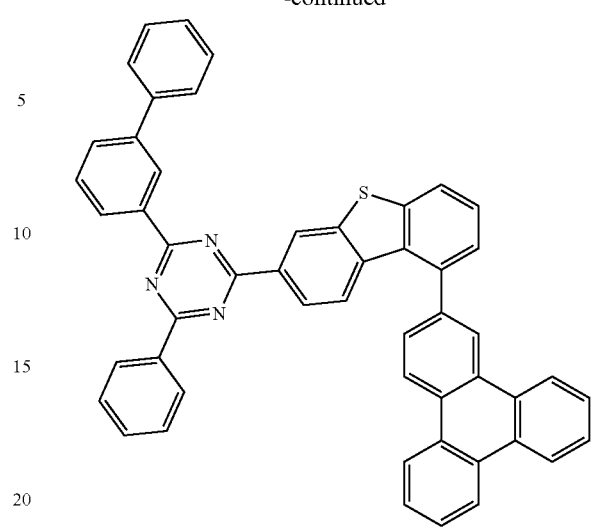
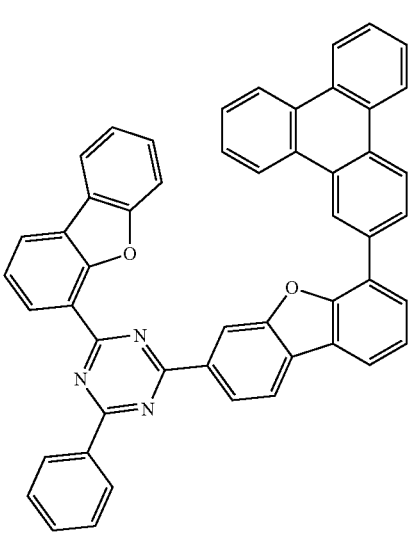
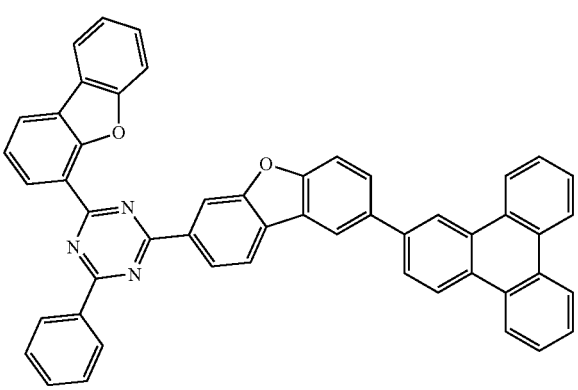

89
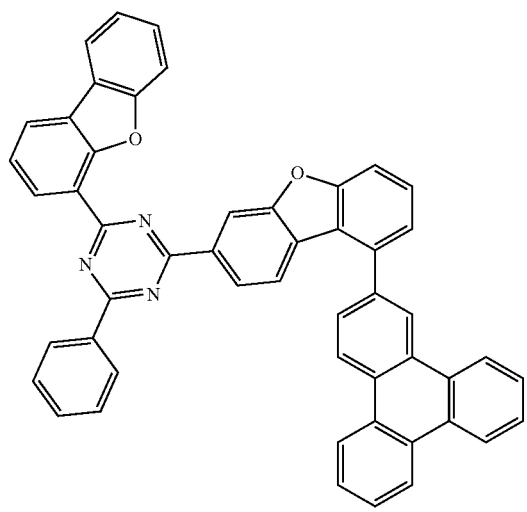
90
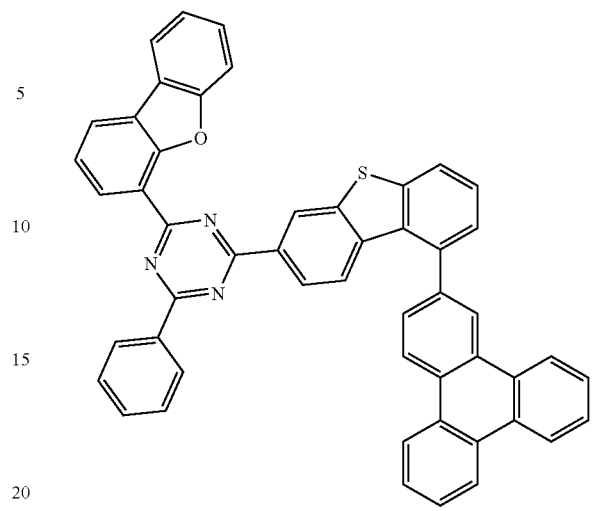
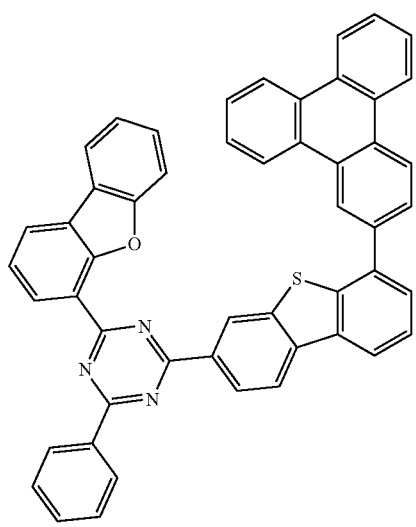
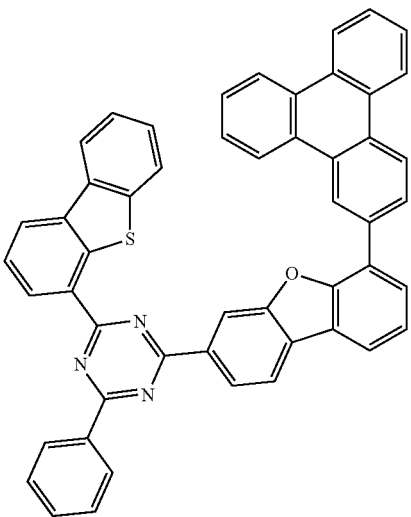
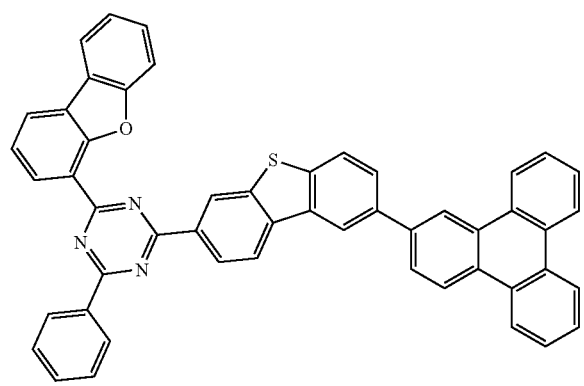
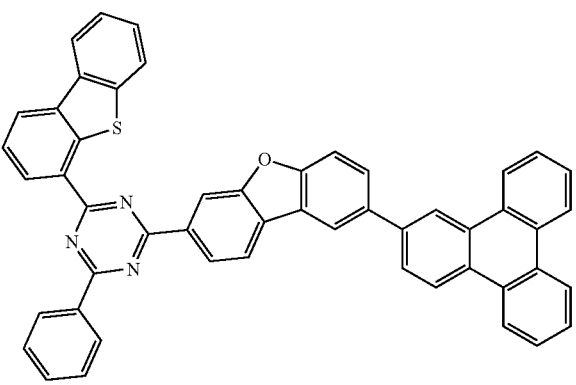

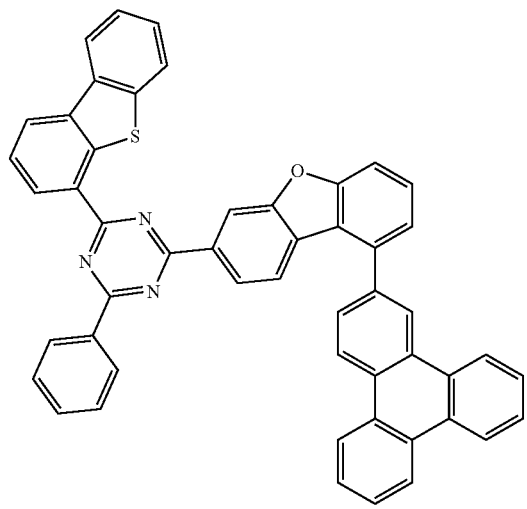
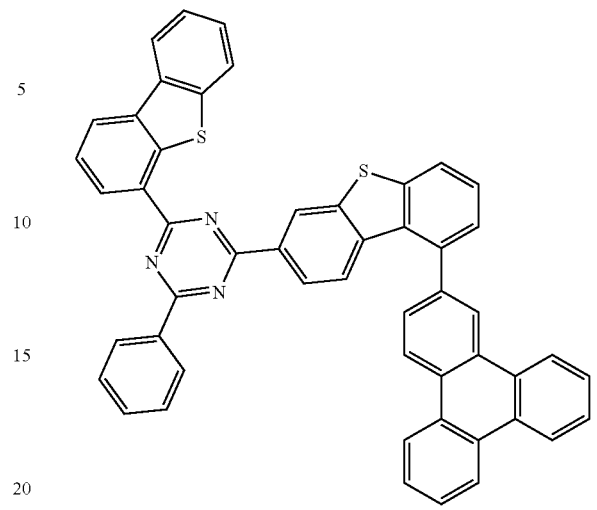
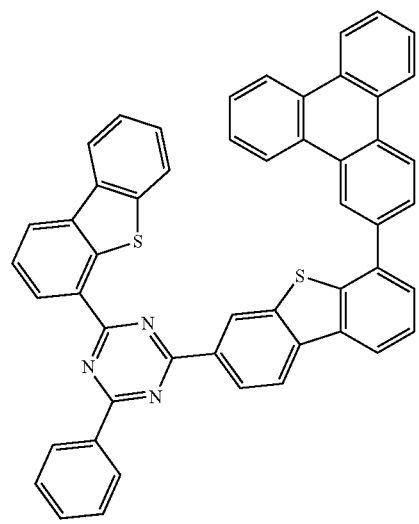
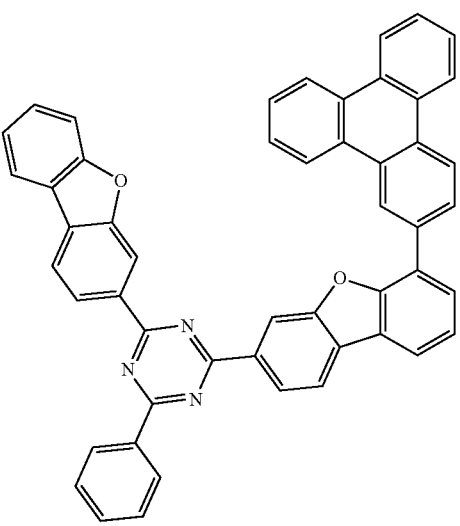
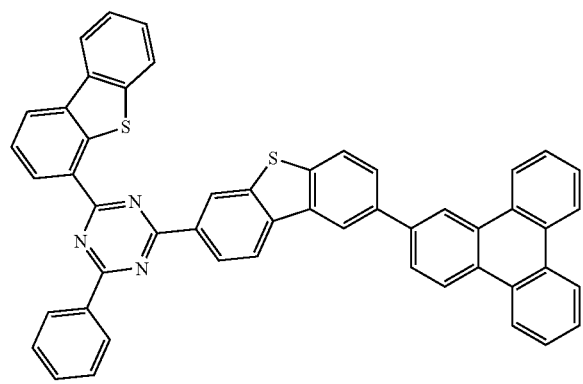
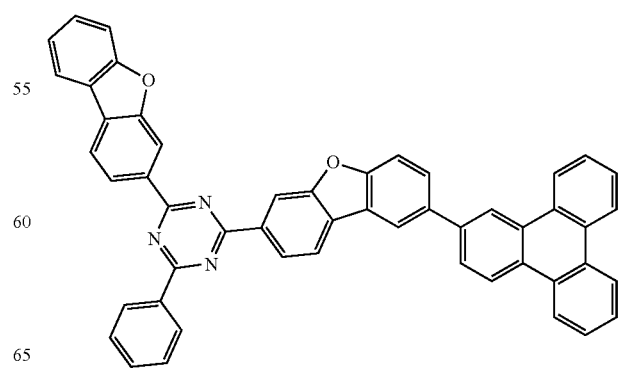

93
-continued
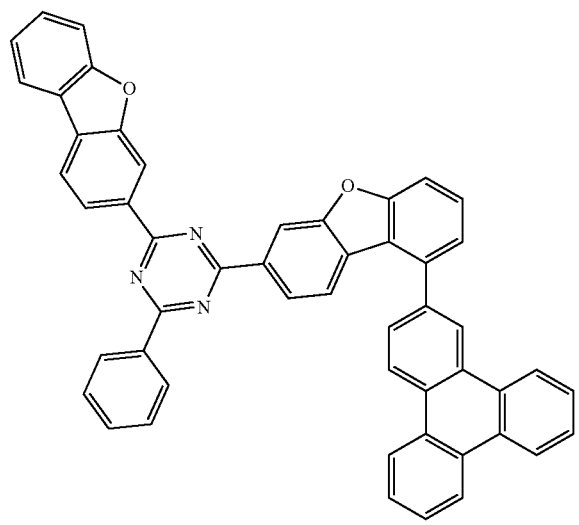
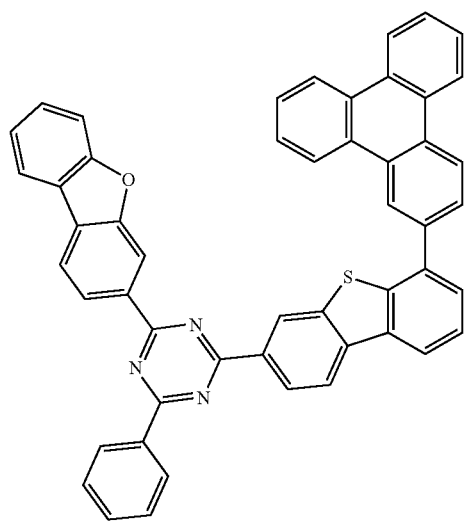
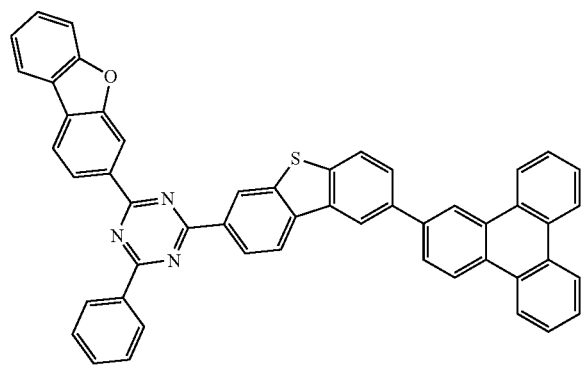
94
-continued
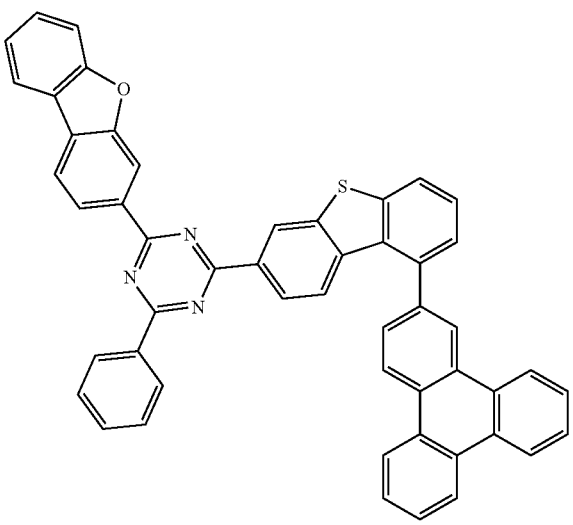
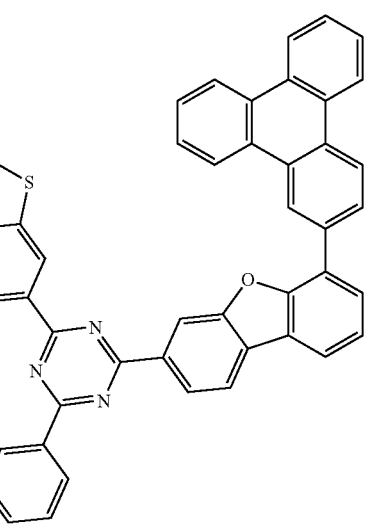
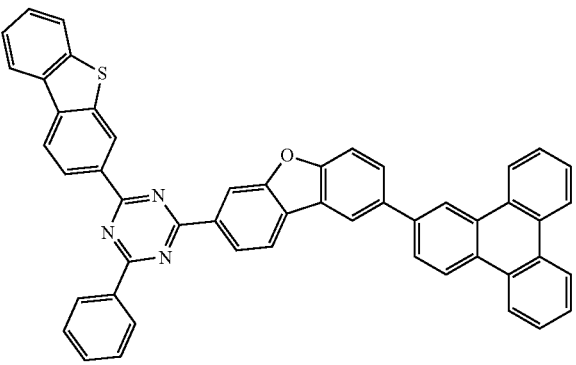

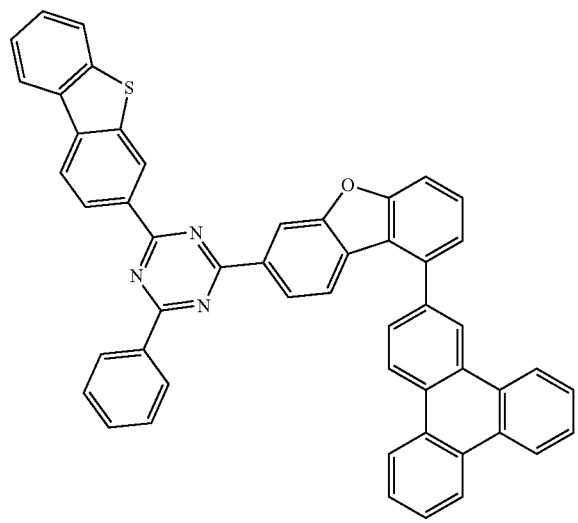
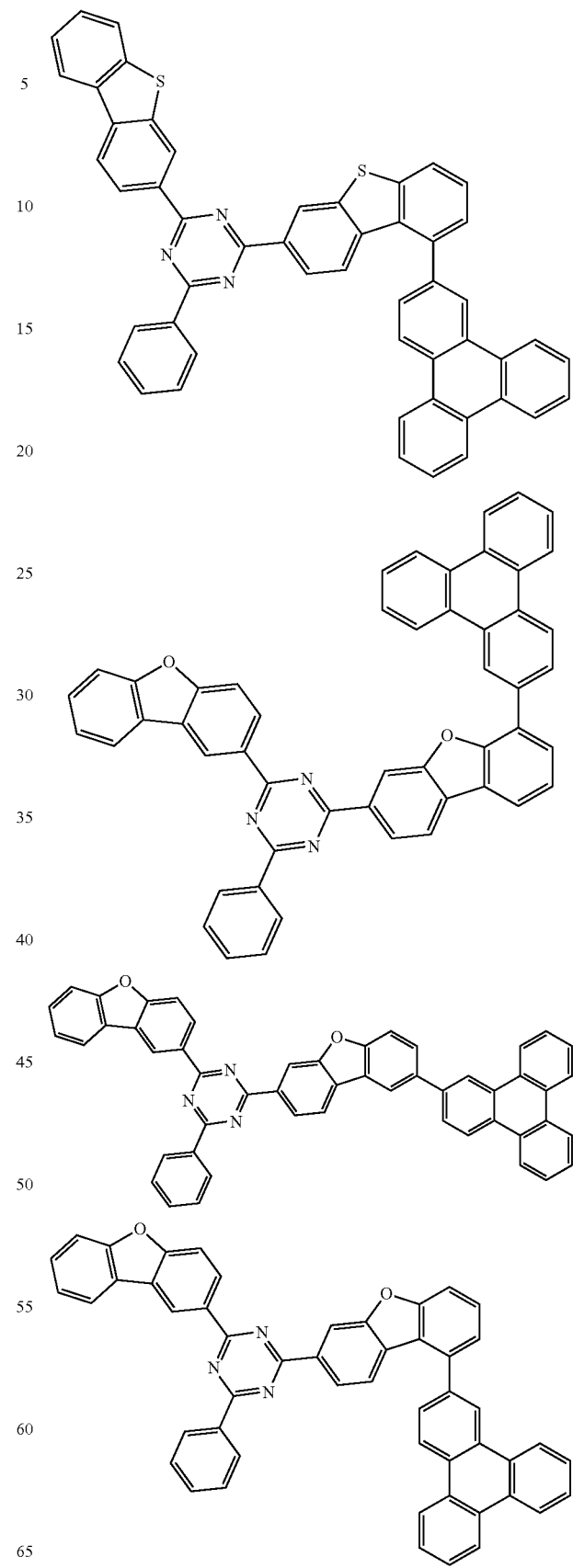

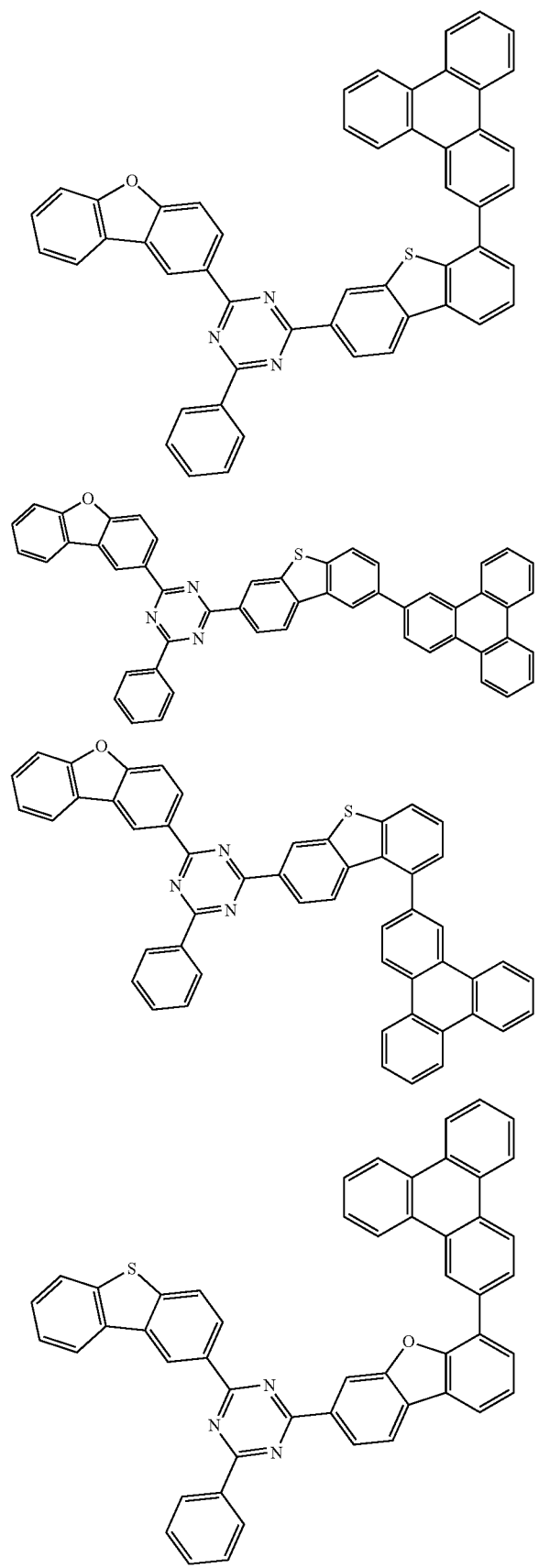
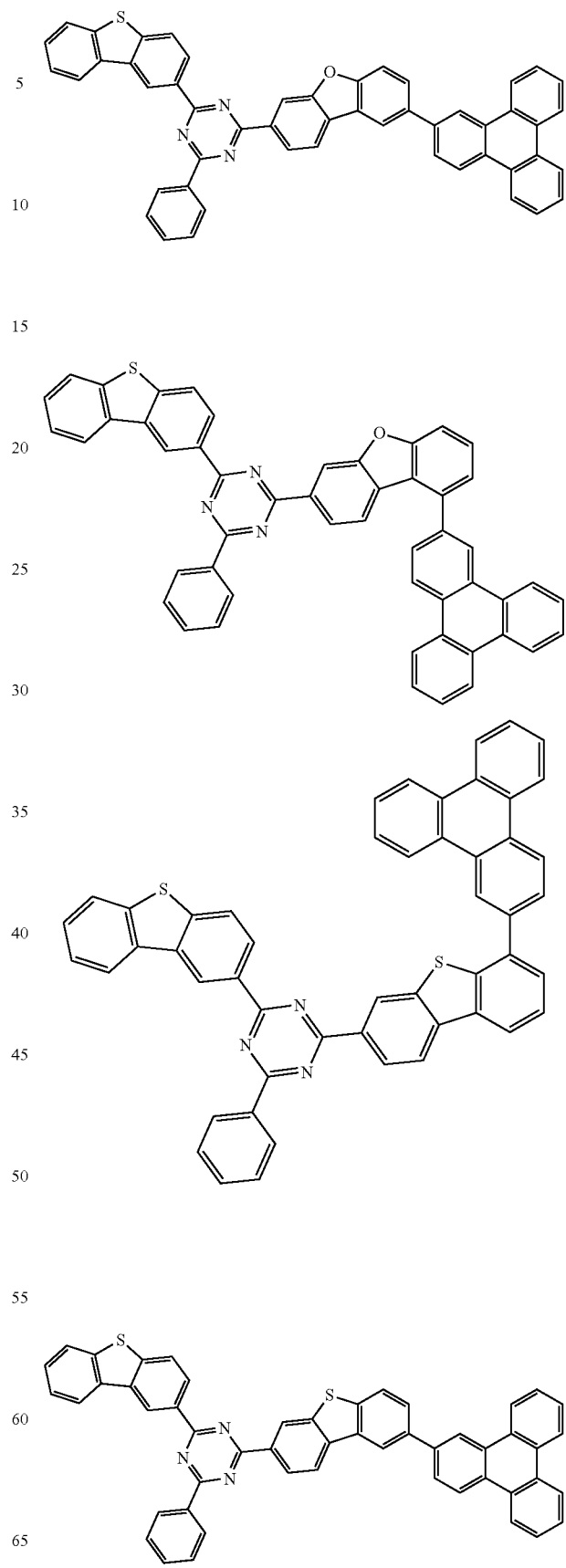

99
-continued
100
-continued
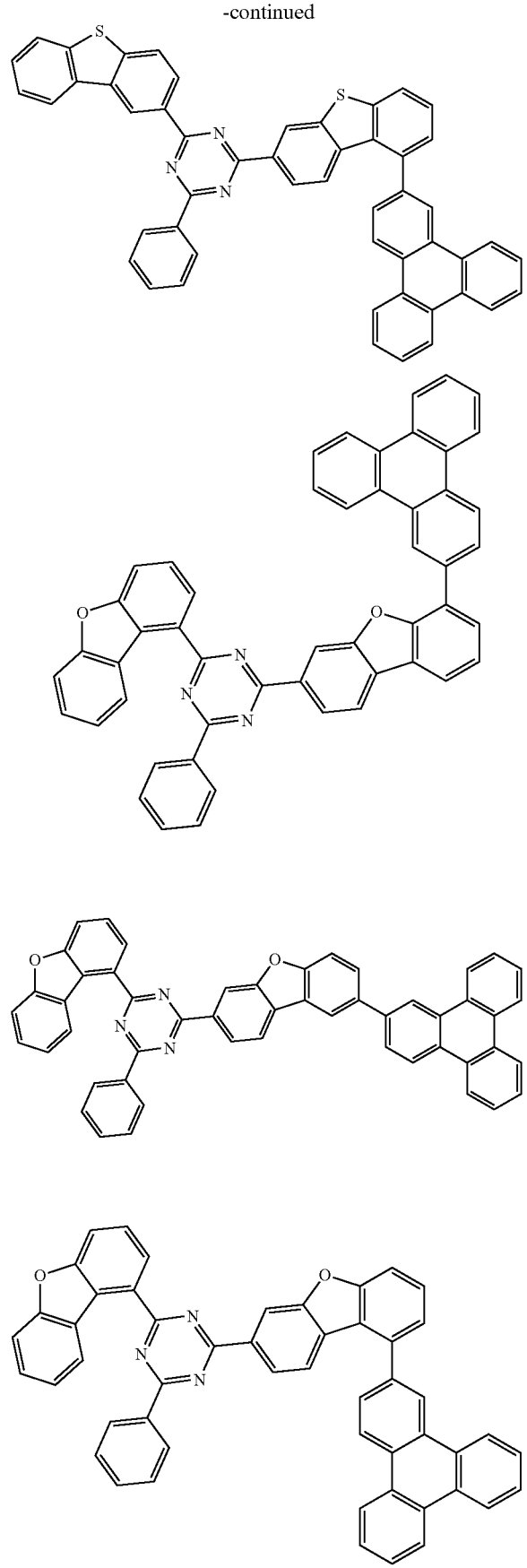

101
-continued

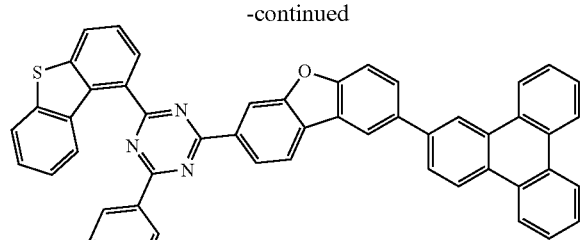

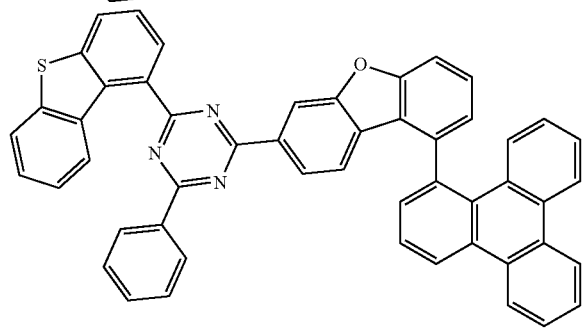

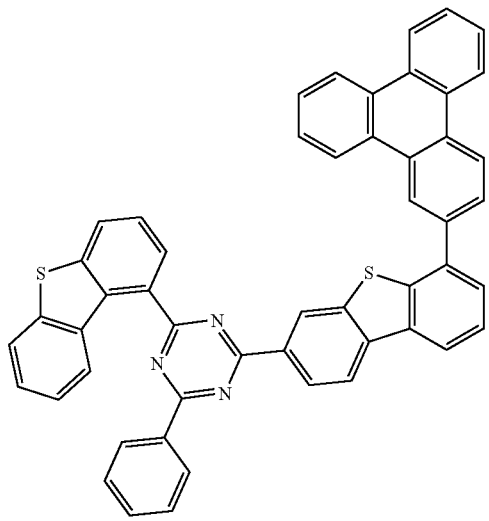

102
-continued

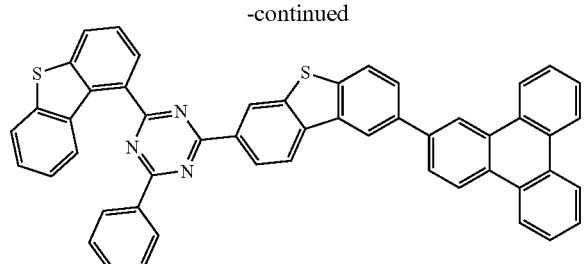

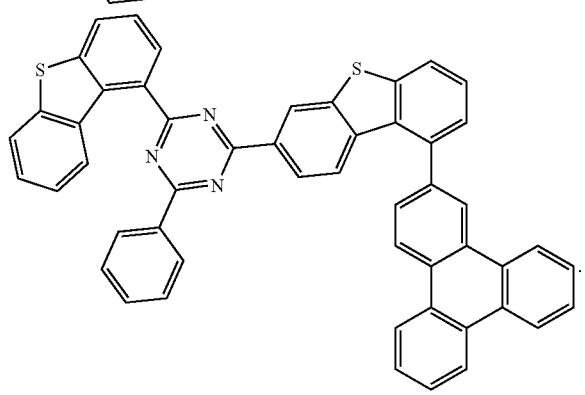

10. An organic light emitting device comprising: a first electrode; a second electrode provided to face the first electrode; and one or more organic material layers provided between the first electrode and the second electrode, wherein one or more layers of the organic material layers comprise the compound according to claim 1.

11. The organic light emitting device according to claim 10, wherein the organic material layer comprising the compound is a light emitting layer, wherein the light emitting layer includes two or more kinds of hosts, and wherein one of the hosts is the compound.

* * * * *